United States Patent
Caldwell et al.

(10) Patent No.: US 7,601,754 B2
(45) Date of Patent: Oct. 13, 2009

(54) FLAVONOID COMPOUNDS AS THERAPEUTIC ANTIOXIDANTS

(75) Inventors: Stuart Thomas Caldwell, Renfrewshire (GB); Christopher James Bennett, Dartford (GB); Richard Charles Hartley, Glasgow (GB); Donald Barton McPhail, Aberdeen (GB); Garry Graeme Duthie, Aberdeen (GB)

(73) Assignee: Antoxis Limited, Aberdeen (GB)

( * ) Notice: Subject to any disclaimer, the term of this patent is extended or adjusted under 35 U.S.C. 154(b) by 568 days.

(21) Appl. No.: 10/521,232

(22) PCT Filed: Jul. 14, 2003

(86) PCT No.: PCT/GB03/03054

§ 371 (c)(1),
(2), (4) Date: Aug. 8, 2005

(87) PCT Pub. No.: WO2004/007475

PCT Pub. Date: Jan. 22, 2004

(65) Prior Publication Data

US 2006/0137207 A1    Jun. 29, 2006

(30) Foreign Application Priority Data

Jul. 13, 2002   (GB) ................. 0216371.5

(51) Int. Cl.
*A61K 31/35*   (2006.01)
*C07D 311/00*   (2006.01)

(52) U.S. Cl. ............... 514/455; 514/453; 514/456; 549/400; 549/401; 549/403

(58) Field of Classification Search ............ 549/400, 549/401, 403; 514/455, 456, 457
See application file for complete search history.

(56) References Cited

U.S. PATENT DOCUMENTS

| 5,280,024 A | | 1/1994 | Bolland et al. | |
| 5,702,691 A | * | 12/1997 | Ichinose et al. | 424/70.1 |
| 6,080,780 A | * | 6/2000 | Paladini et al. | 514/456 |

OTHER PUBLICATIONS

De Meyer, N. et al., J. Med. Chem., 34:736-746, (1991).
Miranda, C.L. et al., J. Agric. Food Chem., 48:3876-3884, (2000).
Sutthivaiyakit, S. et al., Tetrahedron, 58:3619-3622, (2002).
Rice-Evans, C.A. et al., Free Radical Biology & Medicine, 20(7):933-956 (1996). "Structure-Antioxidant Activity Relationships of Flavonoids and Phenolic Acids."

* cited by examiner

*Primary Examiner*—Janet L. Andres
*Assistant Examiner*—Raymond Covington
(74) *Attorney, Agent, or Firm*—Nixon Peabody LLP

(57) ABSTRACT

Novel flavonoid compounds having anti-oxidant activity are described. Formula 1. The compounds have been shown to exhibit anti-oxidative properties in biological systems and their utility in a sunscreen or skincare composition or to treat conditions involving oxidative damage, especially curative or prophylactic treatment of Alzheimer's disease or ischaemia-reperfusion injury, is described.

34 Claims, 5 Drawing Sheets

TBARS production: chain variants of headgroup 9 and myricetin

Fig. 2a

FLAVONOID COMPOUNDS AS THERAPEUTIC ANTIOXIDANTS

CROSS-REFERENCE TO RELATED APPLICATIONS

This application is a 371 National Phase Entry Application of co-pending International Application PCT/GB2003/003054, filed Jul. 14, 2003, which designated the U.S. and which claims the benefit under 35 U.S.C. § 119 of GB Application 0216371.5, filed Jul. 13, 2002.

The present invention relates to new analogues of phytochemicals, to compositions comprising these analogues and to the use of these analogues as therapeutic agents.

Particularly but not exclusively the present invention relates to new analogues of flavonoids having improved lipid solubility and the ability to orientate themselves within lipid membranes.

Oxidative damage to cells is implicated in the development of many clinical conditions including ischaemia-reperfusion injury, cancers, heart disease, arthritis, neurological disorders and auto-immune diseases. To date preventative therapy with antioxidants has not been very successful, partly because targeting and orientating the compounds at the correct site within the cell for optimum effect is difficult. Evidence is now emerging that effective antioxidant intervention during the acute phase of ischaemic events may increase survival rate and minimise irreversible organ damage.

Combinational therapies for treatment of diseases currently incorporate natural and synthetic antioxidants with limited success. There is a need to produce antioxidant agents that possess low toxicity and high therapeutic benefit for use in pharmaceutical preparations. Current natural flavonoid antioxidants are relatively ineffective, being inefficient at protecting cell membranes from free radical oxidative damage.

The low bioavailability and uptake by the human body of dietary antioxidants is a limiting factor in their therapeutic action. Dietary antioxidants have poor performance in the treatment of diseases such as Parkinson's and Alzheimer's and in ameliorating ischaemia-reperfusion injury.

Vitamin E (d-α-tocopherol) is a widely used and naturally occurring antioxidant. It is known to protect cell membranes from free radical mediated oxidative damage. The chemical structure of vitamin E (d-(2R,4'R,8'R)-α-Tocopherol), is shown below;

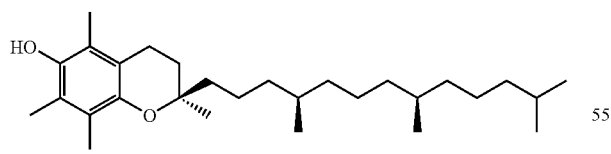

The recognised essential dietary antioxidants are vitamin E and vitamin C. There are also a range of metals, including selenium, iron, copper, zinc and manganese, required from the diet to allow the enzymes to function with antioxidant activity. Carotenoids from the diet may also have antioxidant properties in-vivo in the scavenging of singlet oxygen and in tissues of low partial oxygen pressure.

Alternative natural antioxidants include flavonoids which have the following general structure:

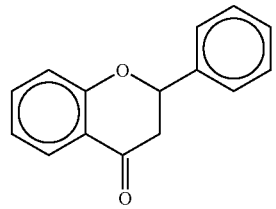

Flavonoids are polyhydroxyphenolic products of the phenylpropanoid biosynthetic pathway in plants, and there are more than 4000 naturally-occurring flavonoids. They are present in a wide range of fruits, vegetables, nuts, and beverages including wine and tea. Flavonoids fall into two distinct groups depending on whether the central heterocyclic ring is saturated or unsaturated. If the central heterocyclic ring is unsaturated (as in anthocyanidin, flavones, flavonols), the molecule is achiral. If the central heterocyclic ring is saturated, as shown above, (as in flavanones and flavans), one or more chiral centres are present, and thus such flavonoids exhibit optical activity. A number of flavonoid structures are shown below;

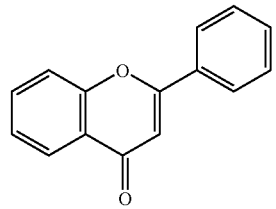

Flavone

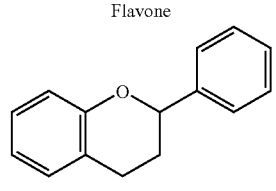

Flavan

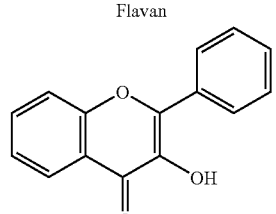

Flavonol

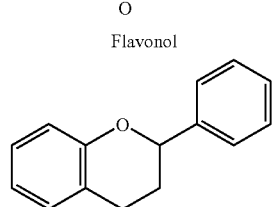

Flavanone

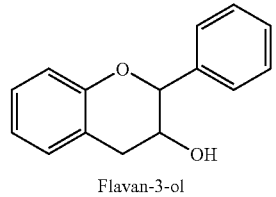

Flavan-3-ol

Selected flavonoids, such as myricetin, exhibit potent antioxidant properties and are more effective as antioxidants than vitamin E both in terms of the number of radicals which one molecule can reduce and in terms of the rate of the radical annihilation reaction. However, flavonoids are poor membrane protectants due to their limited lipid solubility. Consequently flavonoids have had limited application as antioxidants in vivo.

Our kinetic and stoichiometric studies comparing the reducing capabilities of flavonoids to d-α-tocopherol indicate that the antioxidant activity is markedly influenced by the number and position of the hydroxyl groups on the B and C rings as well as the extent of conjugation between the B and C rings. Moreover, within a biological system where a number of polyphenols may be present at similar concentrations, antioxidant efficacy may be predominantly governed by reaction kinetics rather than stoichiometry.

The present invention provides novel compounds having both potent antioxidant activity together with high lipid solubility, thus facilitating their sequestration into the cell membrane.

According to one aspect of the present invention there is provided a compound of the following Formula 1:

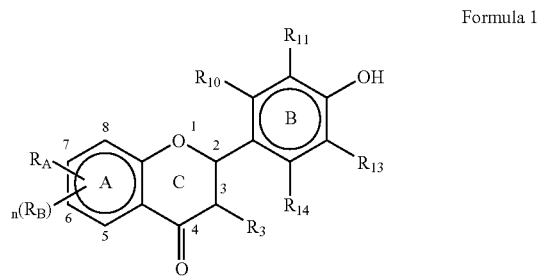

Formula 1 wherein
- $R_A$ is a $C_2$ to $C_{30}$ saturated or unsaturated hydrocarbon chain;
- $R_{10}$, $R_{11}$, $R_{13}$, $R_{14}$ and $R_3$ each independently represent H, OH, a $C_{1-6}$ ether, or a saturated or unsaturated hydrocarbon chain which may be substituted with one or more of nitro, halogen, amino, hydroxyl, ketone or aldehyde group;
- optionally there is a double bond between $C_2$ and $C_3$ of the C ring;
- n represents 0 or 1; and
- $R_B$ is a $C_2$ to $C_{15}$ saturated or unsaturated hydrocarbon chain, and where $R_B$ is present, $R_A$ and $R_B$ are both $C_2$ to $C_{12}$ aliphatic alkyl chains.

Preferably at least one of $R_{10}$, $R_{11}$ and $R_{13}$ represents OH. More preferably at least three of $R_{10}$, $R_{11}$, $R_{13}$, $R_{14}$ and $R_3$ represent OH.

Preferably $R_{10}$ and/or $R_{11}$ represent OH.

In one embodiment both $R_{11}$ and $R_{13}$ represent OH, and more preferably $R_3$, $R_{11}$ and $R_{13}$ all represent OH.

Alternatively $R_3$ and $R_{10}$ both represent OH, more preferably $R_3$, $R_{10}$ and $R_{13}$ all represent OH.

Optionally one or more of $R_{10}$, $R_{11}$, $R_{13}$, $R_{14}$ and $R_3$ represents an ether, preferably a $C_{1-4}$ ether.

Advantageously the flavonoid group is an extended conjugated π-electron system.

Preferably there is a double bond between $C_2$ and $C_3$ of the C ring.

Preferably the B and C rings of the flavonoid have the structure of the B and C rings of myricetin, morin, quercetin, kaempferol, luteolin, or apigenin. More preferably the B and C rings of the flavonoid group have the structure of the B and C rings of myricetin.

Alternatively the B and C rings of the flavonoid group may have the structure of the B and C rings of taxifolin or catechin.

The backbone of $R_A$ may have from two to twenty carbon atoms, preferably from six to fifteen carbon atoms. Suitably the $R_A$ backbone has two, three, four, five, six, seven, eight, nine, ten, eleven, twelve, thirteen, fourteen, fifteen, sixteen, seventeen or eighteen carbon atoms. More preferably the $R_A$ backbone has eight, nine or ten carbon atoms. Optionally the $R_A$ backbone comprises nine, ten, eleven or twelve carbon atoms in total (ie. backbone plus any side chains).

Preferably the backbone of $R_A$ has eight, nine or ten carbon atoms, and $R_3$, $R_{11}$ and $R_{13}$ each represent OH.

The backbone of $R_A$ and/or $R_B$ may be saturated or unsaturated. Preferably the backbone is saturated, but this is not always essential.

Suitably $R_A$ is attached to position 5, 6, 7 or 8 of the A ring of the flavonoid group. Preferably $R_A$ is attached to position 7 of the A ring of the flavonoid group.

Suitably $R_B$ is attached to position 5, 6, 7 or 8 of the A ring (but $R_B$ may not be attached to the same position of the A ring as $R_A$). Generally $R_B$ is a saturated alkyl chain of $C_1$ to $C_6$, for example $C_1$ to $C_4$, typically $C_2$ or $C_3$. Usually $R_B$ is a straight-chained alkyl group.

In a preferred embodiment $R_A$ has the following structure:

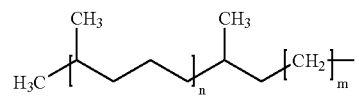

wherein
- n is an integer from 1 to 7, preferably 2 or 3; and
- m is an integer from 1 to 7, preferably 1 or 2.

More preferably $R_A$ has the following structure:

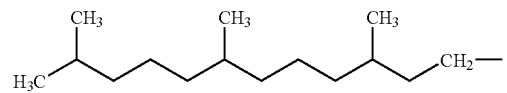

Alternatively $R_A$ has the following structure:

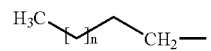

wherein n is an integer from 2 to 27, preferably n is 4 to 12, more preferably n is 5 to 7 (ie. giving a total chain length of 8 to 10).

In another embodiment $R_A$ has the following structure:

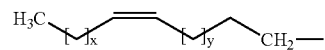

wherein
- x is an integer from 1 to 25, preferably 1 to 15, more preferably x is 1, 2, 3, 4, or 5;

y is an integer from 1 to 25, preferably 1 to 15, more preferably y is 1, 2, 3, 4, or 5;
and wherein x+y=25 or less, preferably x+y=2, 3, 4 or 5.

In another embodiment $R_A$ has the following structure:

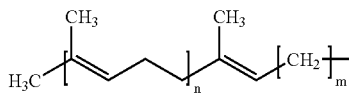

wherein
n is an integer from 1 to 7, preferably n is 1, 2, or 3, most preferably n is 1; and
m is an integer from 1 to 7, preferably m is 1, 2 or 3, most preferably m is 1.

In one embodiment, the flavonoid group of the compound of the present invention preferably has the following structure:

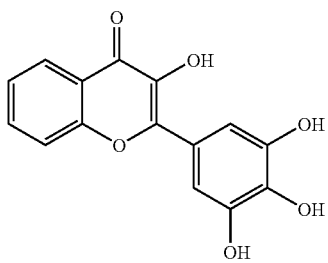

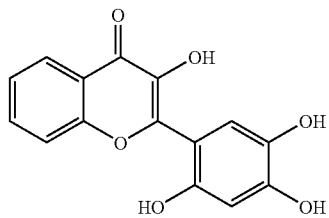

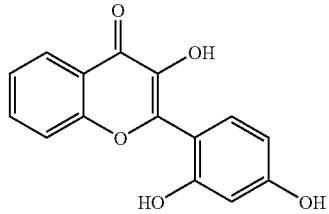

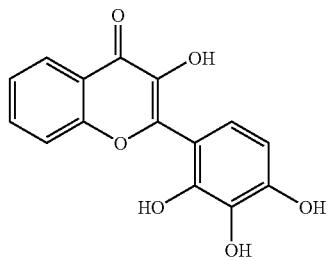

In one embodiment, the compound of the present invention has the following structure:

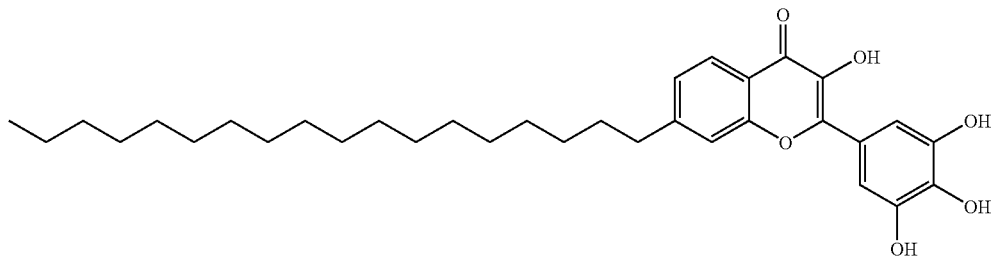

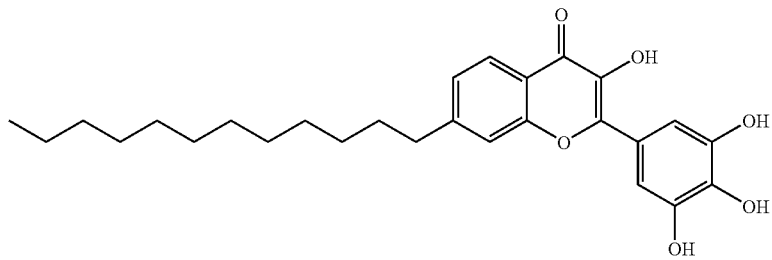

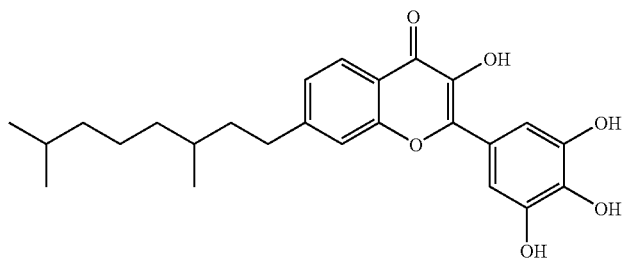

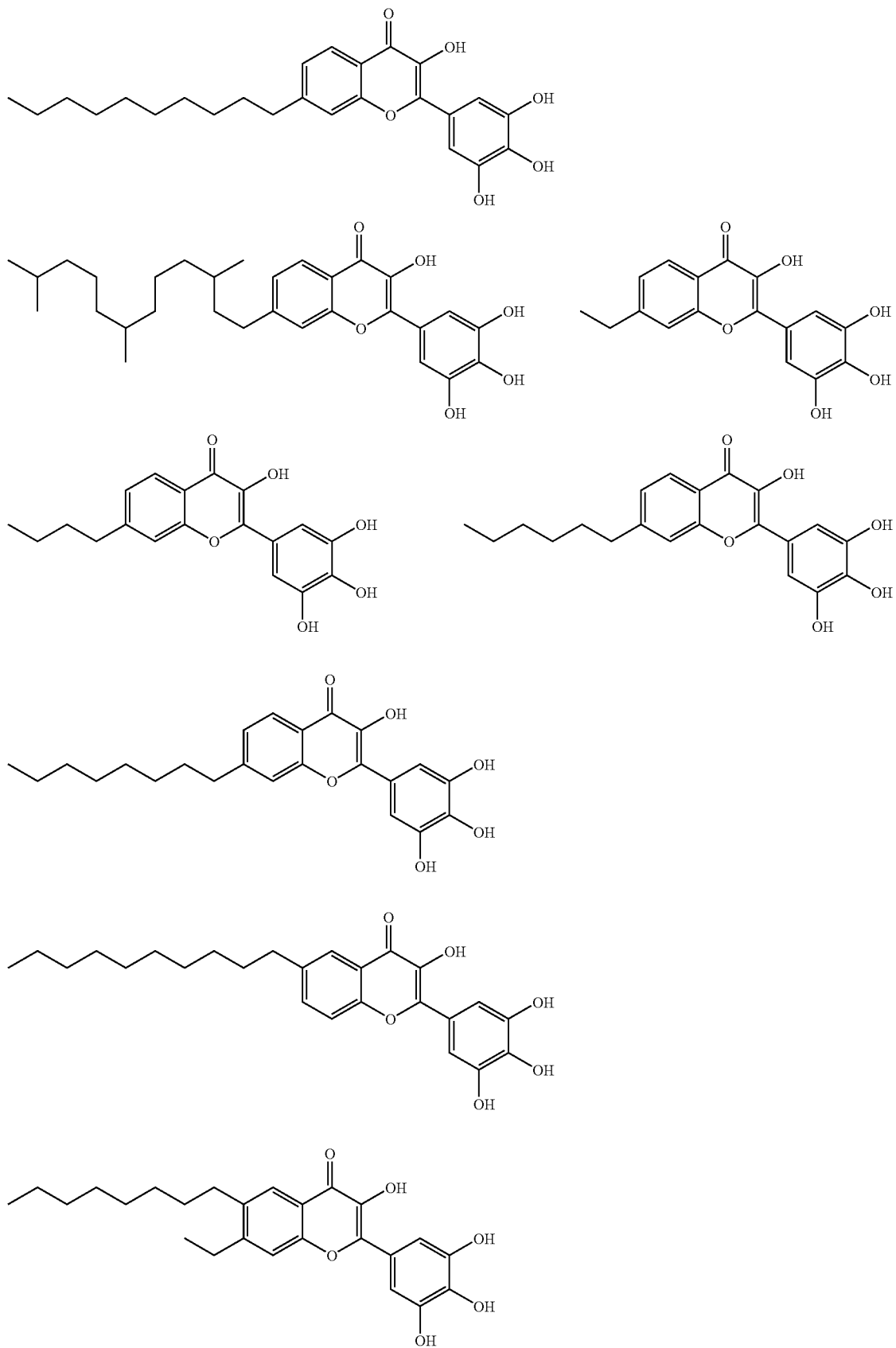

-continued

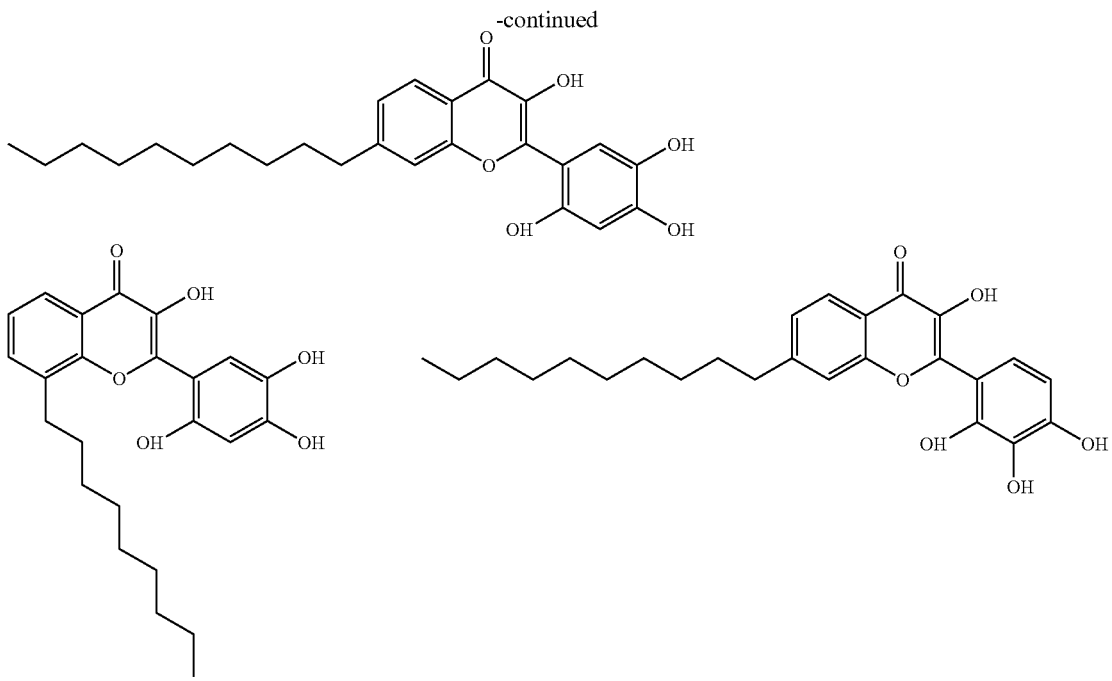

Whilst the Applicant does not wish to be bound by theoretical considerations, it is believed that addition of $R_A$ and optionally $R_B$ to the A-ring increases membrane partitioning and also adds the important spatial distribution factor observed with vitamin E. It is anticipated that crossing of the blood/brain barrier will also be enhanced.

According to a further aspect of the present invention there is provided a composition comprising a compound as described above and at least one pharmaceutically acceptable excipient or carrier. The composition may be a sunscreen composition.

According to a further aspect of the present invention there is provided a method of preventing UV damage to the skin (for example sunburn or skin cancers such as melanoma) of a mammalian animal, said method comprising the step of administering a therapeutically effective amount of the sunscreen composition as described above to a patient's skin prior to UV exposure. The method is of most interest for human patients.

The composition will usually be applied topically to the patient's skin.

The composition may alternatively be formulated as a skincare composition and may, for example, include emollients and moisturisers. The skincare composition may be of particular utility in preventing or reversing the effects of ageing, of reducing apparent wrinkling, and/or treating or preventing dry skin.

According to a further aspect of the present invention there is provided a foodstuff stabiliser composition comprising a compound as described above.

It is believed that the ability to combat free radicals will be of utility in preventing or delaying the deterioration in food quality during storage. It is envisaged that the composition will be particularly effective where the foodstuff stabiliser composition is in the form of an emulsion, especially an emulsion having a low fat/high water content. The foodstuff stabiliser composition will be particularly suitable for low fat spreads, salad dressings etc.

According to a further aspect of the present invention there is provided a method of treating a patient having a disease or disorder involving oxidative damage, said method comprising the step of administering a therapeutically effective amount of the composition described above to said patient. Generally said patient will be a human, but treatment of other mammalian animals is also possible. The method of the present invention may also be used prophylactically to prevent a patient developing a disease or disorder involving oxidative damage.

The disease or disorder involving oxidative damage may be selected from the group consisting of cancer (for example colon, liver or bladder cancer), heart disease, especially to prevent subsequent heart attacks, neurological disorders, (particular mention may be made of Alzheimer's or Parkinson's disease), auto-immune disorders (particularly arthritis), ischaemia-reperfusion injury (particularly stroke, or risk of stroke), diabetic complications, septic shock, hepatitis, atherosclerosis and complications arising from HIV or Hepatitis B.

If the disease or disorder is stroke or risk of stroke, the composition described above is preferably administered before the stroke occurs as a prophylatic to reduce the risk of stroke occurrence, or within twelve hours (preferably within four hours) of stroke occurrence.

Most suitably the disease or disorder to be treated is an ischaemia-reperfusion injury.

According to a further aspect of the present invention there is provided the use of a compound of Formula 1 as described above for the manufacture of a medicament for the treatment or prevention of a disease or disorder involving oxidative damage. The disease or disorder may be cancer (for example colon, liver or bladder cancer), heart disease, especially to prevent subsequent heart attacks, neurological disorders, (particular mention may be made of Alzheimer's or Parkinson's disease), auto-immune disorders (particularly arthritis), ischaemia-reperfusion injury (particularly stroke or risk of stroke), diabetic complications, septic shock, hepatitis, atherosclerosis, and complications arising from an immune response to HIV or Hepatitis B. Most suitably the disease or disorder is ischaemia-reperfusion injury or Alzheimer's disease.

The composition described above may be used prophylactically or curatively.

According to a further aspect of the present invention there is provided a method of manufacturing a compound of Formula 1 as described above, said method comprising providing an intermediate compound A and an intermediate compound B, wherein intermediate compound A has the structure $R_4M$ wherein M is a metal or metalloid group (such as $ZnCl_2$, $B(OH)_2$, 9-boracyclo[3.3.1]nonyl, $SnBu_3$ or MgBr) where the metal is directly attached to $R_4$, and $R_4$ is a $C_2$ to $C_{30}$ saturated or unsaturated alkyl chain which may optionally be substituted with small alkyl groups such as $CH_3$ and $C_2H_5$; and $R_4M$ is capable of participating in transition metal catalysed cross-coupling reactions;

and intermediate compound B has the following structure:

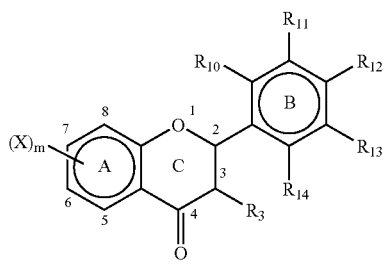

wherein $R_{12}$ represents OH or an O-protecting group $R_3$, $R_{10}$, $R_{11}$, $R_{13}$, and $R_{14}$ each independently represent H, OH, $C_1$ to $C_4$ aliphatic alkyl group or an O-protecting group where required, and optionally there is a double bond between $C_2$ and $C_3$ of the C ring;

X is a halogen, O-trifluoromethane sulphonate or any other group used in cross-coupling reactions; and m=1 or 2 (ie 1 or 2 groups may be attached to the A Ring), and reacting intermediate compound A with intermediate compound B by transition metal catalysed cross-coupling reactions and subsequently deprotecting at least one OH group.

Preferably $R_4M$ is an organomagnesium, organozinc, organoboron or organotin compound. Alternatively M may be a silyl group.

The transition metal catalyst may be any suitable transition metal catalyst used in cross-coupling reactions and particular mention may be made of palladium, nickel or iron complexes.

The protecting group may suitably be methoxymethyl, benzyl (with an optionally substituted aromatic ring), tetrahydropyranyl (THP), or a small alkyl group such as methyl.

Usually all of the OH groups will be protected but it may be possible that certain groups need not be protected under certain reaction conditions. In particular $R_3$ can be OH.

According to an alternative embodiment, there is provided a method of manufacturing a compound of Formula 1 as described above, said method comprising providing an intermediate compound C and an intermediate, wherein said intermediate compound C has the structure $R_4CHCHR$ wherein $R_4$ is as defined above for Formula 1, and wherein intermediate compound D has the following structure:

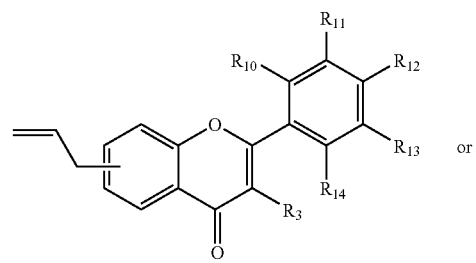

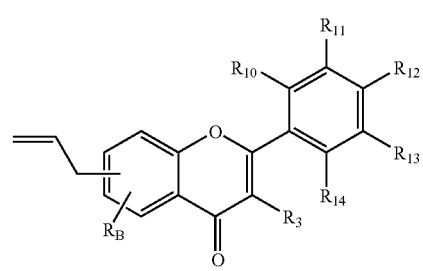

wherein $R_{12}$ represents OH or an O-protecting group; $R_3$, $R_{10}$, $R_{11}$, $R_{13}$ and $R_{14}$ each independently represent H, OH, $C_{1-4}$ aliphatic alkyl or an O-protecting group where required; and $R_B$ is as defined for Formula 1 or is an allyl group capable of cross-metathesis, and reacting intermediate compound C with intermediate compound D by cross-metathesis in the presence of an alkene cross-metathesis catalyst and subsequently deprotecting at least one OH group.

Suitable exemplary alkene cross-metathesis catalysts are set out below:

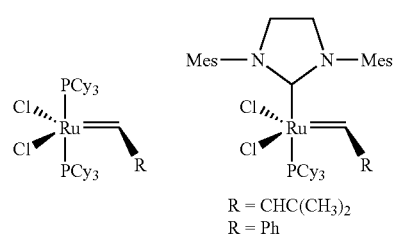

R = CHC(CH$_3$)$_2$
R = Ph

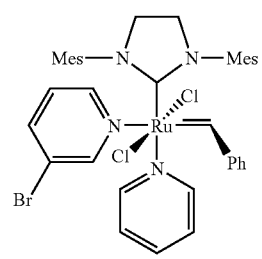

A reaction scheme for cross-metathesis on the flavonoid as described above is presented for clarity (all definitions are as given above).

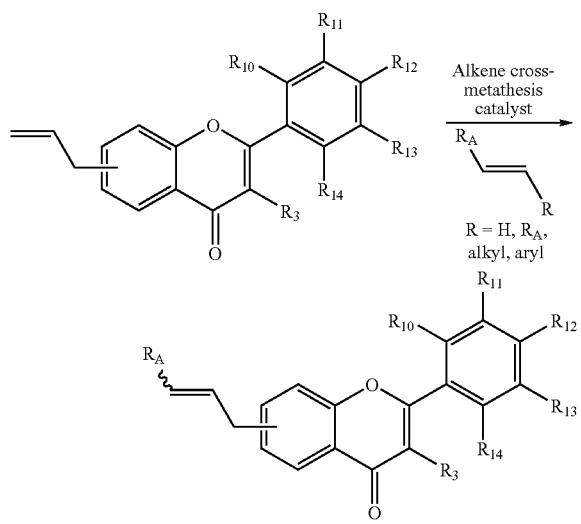

Alternative methods of manufacturing a compound according to Formula 1 are also possible.

Thus, the present invention provides a method wherein the side-chain is attached to the A-ring by a cross-coupling or cross-metathesis reaction to provide a substituted phenyl which is subsequently used as a reactant to construct the flavonol core according to known methodology, for example Algar-Flynn-Oyamada (AFO) oxidation or Baker-Venkataraman rearrangement/cyclisation (see Wagner in "The Flavanoids", Chapman and Hall; London 1975; pages 144 to 146).

A cross-coupling reaction scheme suitable to manufacture an intermediate for production of a compound of Formula 1 is represented below:

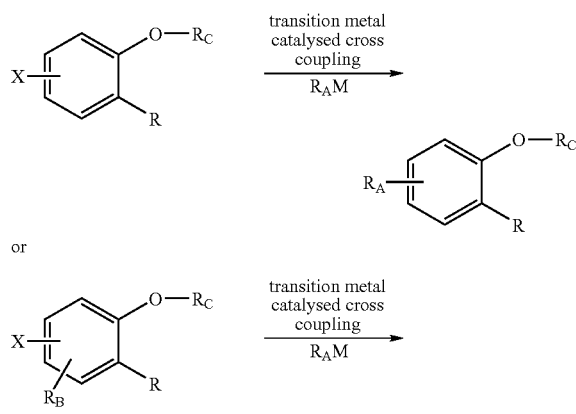

wherein
R represents H, COCH$_3$, COCH$_2$OCH$_3$, COCH$_2$OPG (where "PG" is any suitable protecting group as discussed above) or COCH=CHAr (where "Ar" is any aromatic group);
R$_C$ is H or a protecing group.

X is a halogen, O-trifluoromethane sulphonate or any other group used in cross-coupling reactions;
R$_B$ is as defined in Formula 1 or an allyl group capable of cross-metathesis; and
R$_A$M is as defined above for intermediate compound A.

Alternatively the intermediate group can be obtained by cross-metathesis. A cross-metathesis reaction scheme suitable to manufacture an intermediate for production of a compound of Formula 1 is represented below:

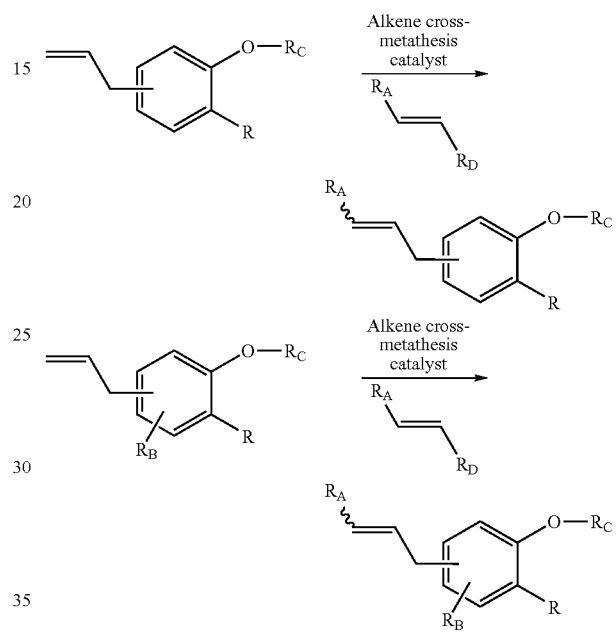

wherein
R represents H, COCH$_3$, COCH$_2$COCH$_3$, COCH$_2$OPG (where "PG" is any suitable protecting group as discussed above or COCH2=CHAr (where "Ar" is any aromatic group);
R$_D$ represents H, a C$_{1-6}$ alkyl or aryl group or a group R$_A$;
R$_A$ is as defined above for Formula 1;
R$_C$ is H or a protecting group; and
R$_B$ is as defined in Formula 1 or is an allyl group capable of cross-metathesis.

A typical reaction scheme (Reaction Scheme A) can be represented as:

Reaction Scheme A

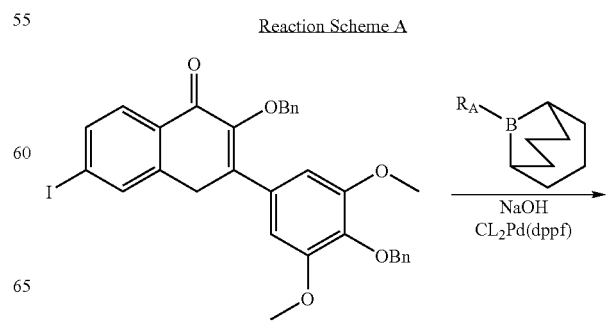

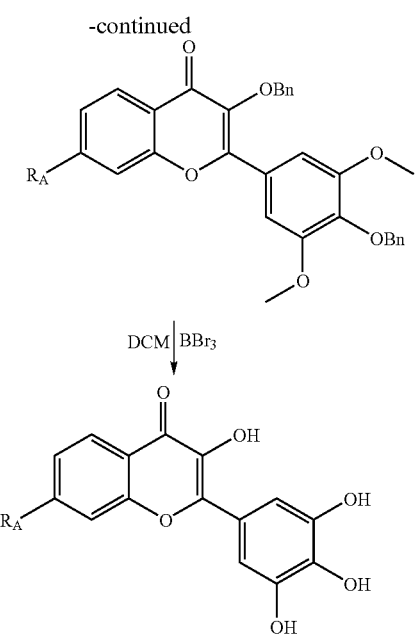
$R_A$ of Reaction Scheme A is as defined above for Formula 1. Exemplary $R_A$ sidechains are:
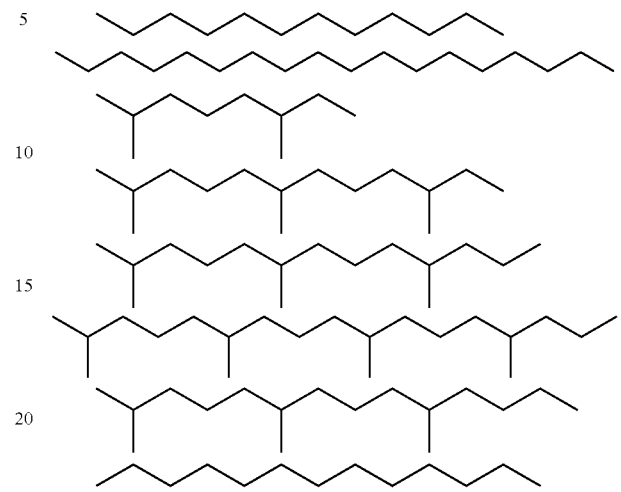
An alternative generic reaction scheme (Reaction Scheme B) is:
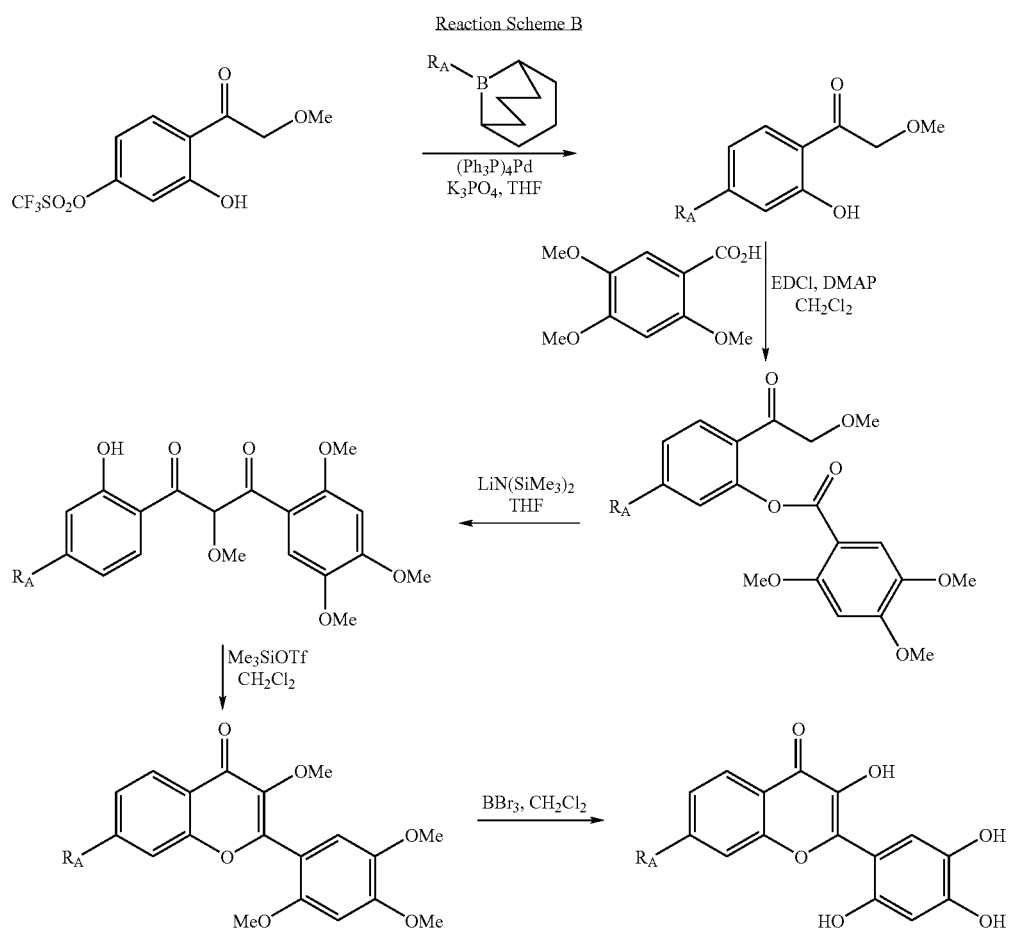

$R_4$ typically represents any alkyl chain as defined above for Formula 1.
A further alternative reaction scheme (Reaction Scheme C) is:
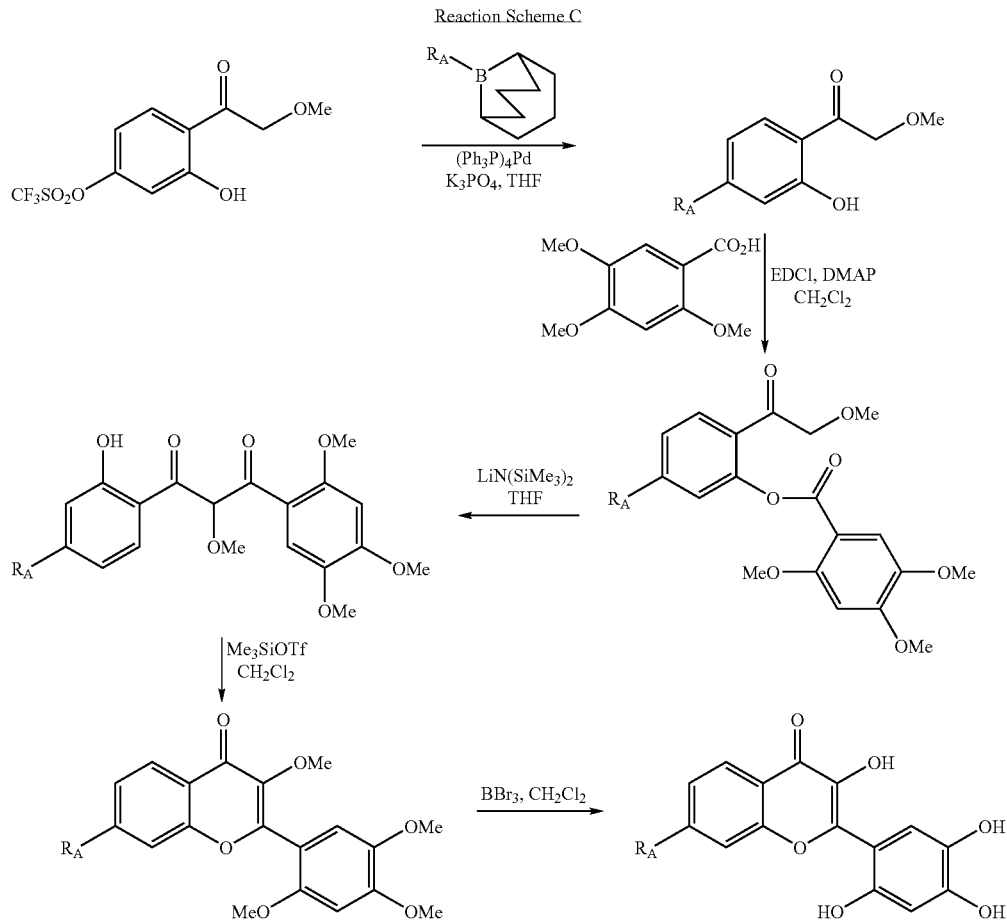
Again, $R_A$ is as defined above in Formula 1.
A yet further alternative reaction scheme (Reaction Scheme D) is:
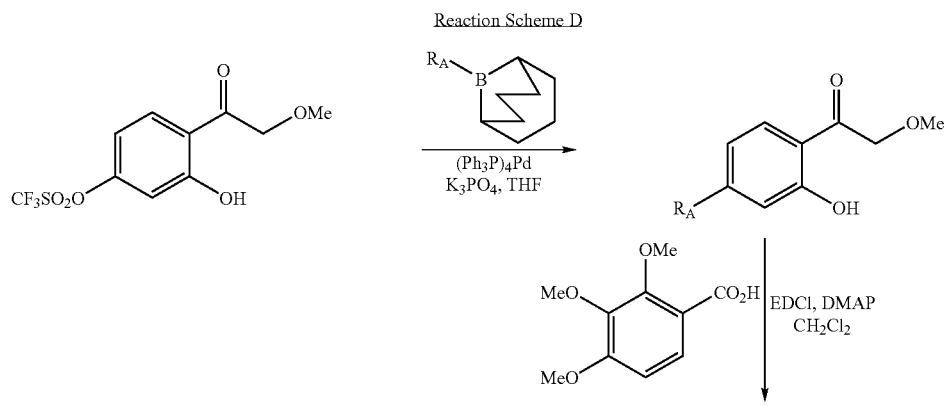

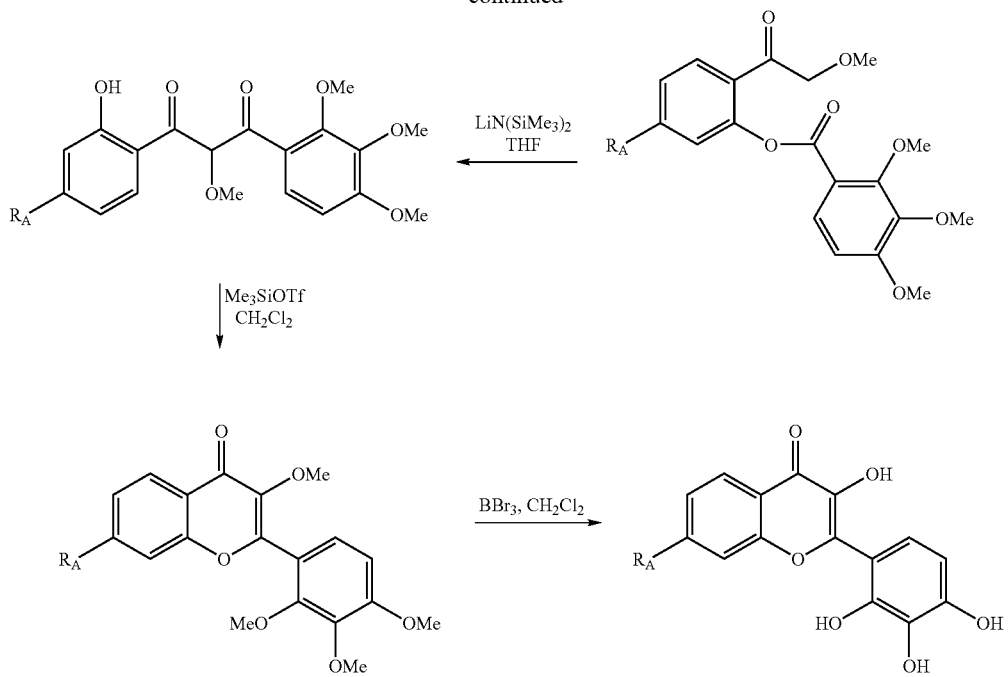
$R_A$ is as defined above in Formula 1.
A yet further alternative reaction scheme (Reaction Scheme E) is:
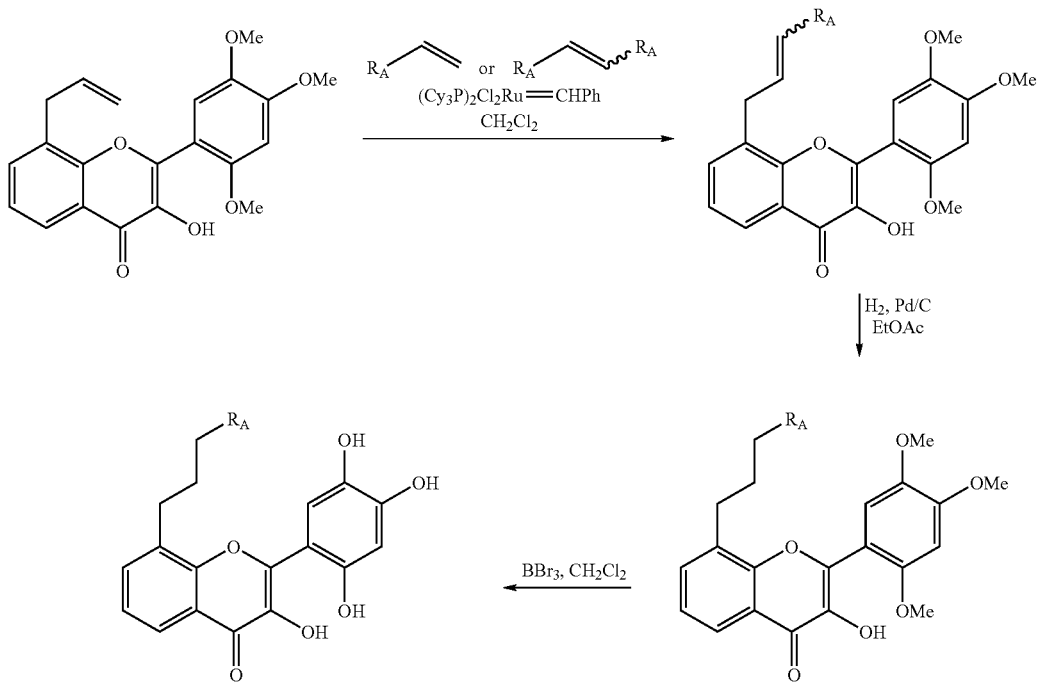
$R_A$ is again as previously defined.
Reaction Scheme F shows a suitable purification procedure.

Reaction Scheme F

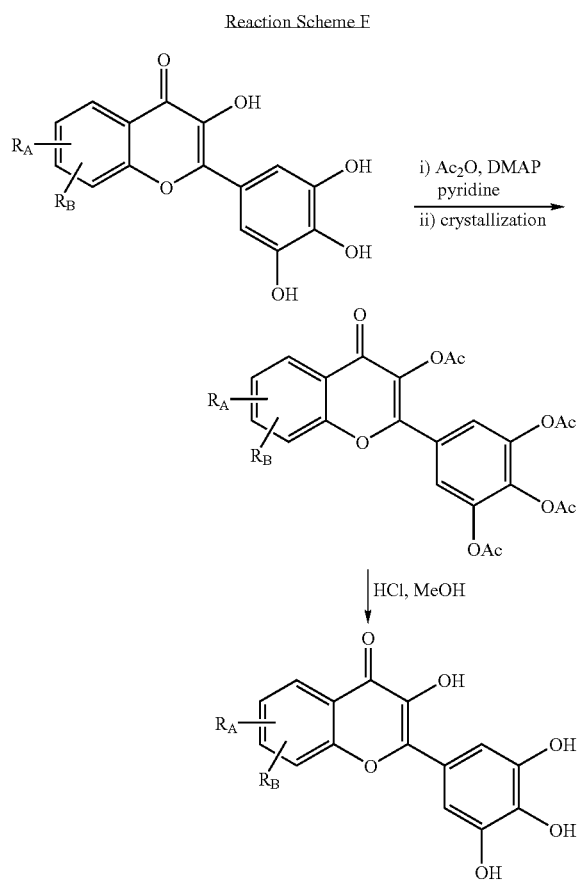

$R_A$ is again as previously designed.
$R_B$ is as $R_A$ but can also be M.

The present invention will now be further described by reference to the non-limiting examples and figures in which:

FIG. 2a shows the efficacy of target compounds of varying chain length at inhibiting lipid peroxidation by measuring their inhibition of TBARS production.

FIG. 3a is a scatter plot of the data shown in FIG. 2a.

EXAMPLE 1

Figure 1:
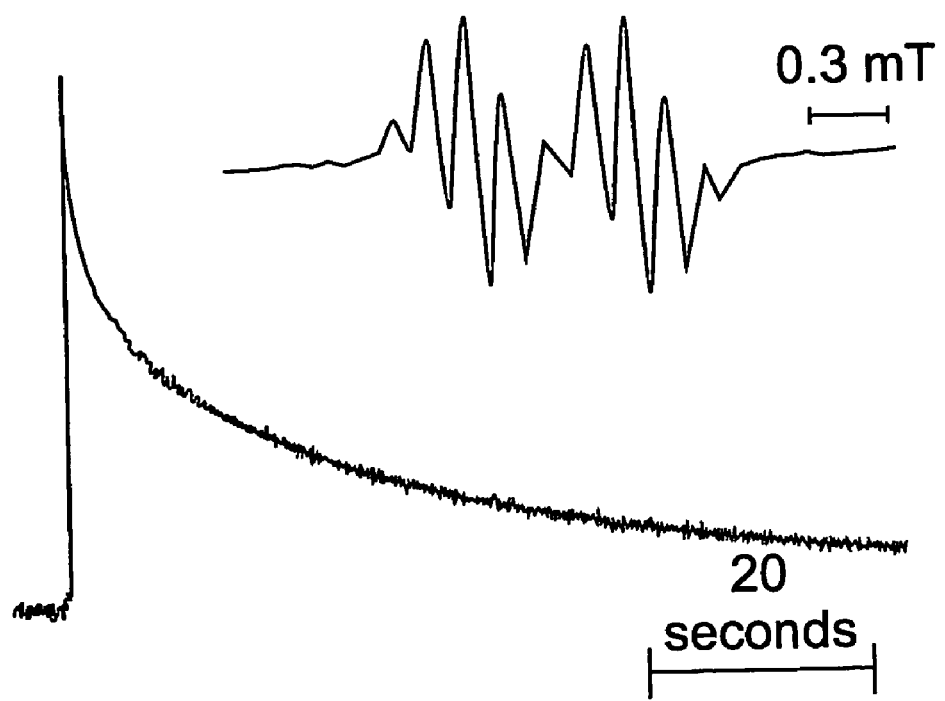
FIG. 1 shows the decay curve of the galvinoxyl resonance obtained in ESR timesweep mode (static field) during in situ reduction of the radical by quercetin. Inset is the fieldsweep spectrum of galvinoxyl.

7-Ethyl-3-hydoxy-2-(3,4,5-trihydoxy-phenyl)-chromen-4-one (compound 9c) was prepared by synthesis from the corresponding acetophenone by aldol condensation to give a chalcone, then Algar-Flynn-Oyamada (AFO) Oxidation to give a flavonol and followed by deprotection as follows:

1-(4-Ethyl-2-hydroxy-phenyl)-ethanone (18)

To aluminium chloride (23 g, 172 mmol, 1.9 equ) was added 3-ethyl-phenyl-acetate (14.82 g, 90 mmol) dropwise. The mixture was heated to 130° C. for 150 minutes then cooled. 2M HCl (50 ml) was added slowly and the mixture stirred for 45 minutes, then poured into 2M HCl (85 ml) and extracted into diethyl ether (2×). The combined organic layers were washed with water, 1% sodium carbonate, water then dried (MgSO$_4$) and concentrated in vacuo to give 18 (10.8 g, 97%) as a brown oil.

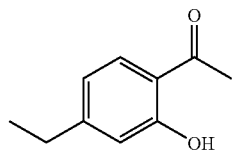

$^1$H nmr (400 MHz, CDCl$_3$) 1.81 (t, 3H, 7.6 Hz) 2.60-2.63 (m, 5H) 6.74 (dd, 1H, 1.5+8 Hz) 6.79 (s, 1H) 7.63 (d, 1H, 8 Hz) 12.28 (s, 1H). $^{13}$C nmr (100 MHz, CDCl$_3$) 15.12 (CH$_3$) 26.87 (CH$_3$) 29.53 (CH$_2$) 117.55 (CH) 118.12 (Q) 119.46 (CH) 131.09 (CH) 154.62 (Q) 163.01 (Q) 204.28 (Q). EI+ 164.1 (30%, M$^+$) 149.1 (100%, [M–Me]$^+$) C$_{10}$H$_{12}$O$_2$ Calc. 164.0837 Found 164.0836.

1-(4-Ethyl-2-hydroxy-phenyl)-3-(3,4,5-trimethoxy-phenyl)-propenone (22)

To a stirring suspension of 18 (5.00 g, 30 mmol) and 3,4,5-trimethoxy benzaldehyde (7.20 g, 37 mmol, 1.2 eq) in ethanol (145 ml) was added potassium hydroxide (4.21 g, 7.5 mmol, 2.5 eq). The reaction mixture was stirred for 200 hours then acidified (1 N HCl) and extracted with DCM (3×). The combined organic layers were then washed with saturated aqueous sodium bicarbonate, 10% sodium bisulfite solution and then saturated aqueous sodium bicarbonate again. The organic layer was then dried (MgSO$_4$) and concentrated in vacuo to give 22 (9.62 g, 92%) as a brown tar.

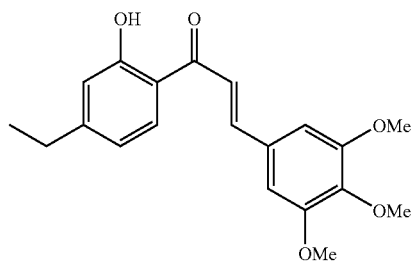

EI+ 342.2 (100%, M$^+$) C$_{20}$H$_{22}$O$_5$ Calc. 342.1467 Found 342.1467.

7-Ethyl-3-hydroxy-2-(3,4,5-trimethoxy-phenyl)-chromen-4-one (26)

To a stirring solution of 22 (1.60 g, 4.7 mmol) in methanol (45 ml) and 16% aqueous sodium hydroxide solution (6.5 ml, 26 mmol, 5.6 equ) at 0° C. was added 15% aqueous hydrogen peroxide (6.5 ml, 29 mmol, 6.1 equ) dropwise. The solution was stirred at 0° C. for ten minutes then sealed and placed in a refrigerator for 26 hours. The reaction was then acidified (2N HCl) and extracted with dichloromethane (3×). The organic layer was then dried (MgSO$_4$) and concentrated to give a brown oil. This was taken up in dichloromethane, washed with 10% sodium bisulfite solution, dried (MgSO$_4$) and concentrated to give 26 (0.777 g, 47%) as a yellow solid. This was used without further purification.

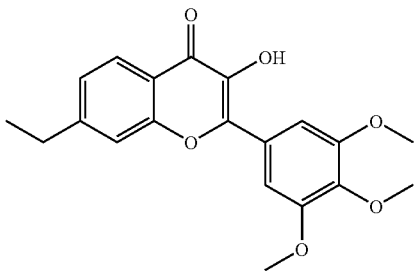

7-Ethyl-3-hydroxy-2-(3,4,5-trihydroxy-phenyl)-chromen-4-one (9c)

To a stirring solution of 26 (0.504 g, 1.4.mmol) in dichloromethane (50 ml) under Ar at 0° C. was added boron tribromide in dichloromethane (1.0M, 10 ml, 10 mmol, 7 equ). The mixture was warmed to room temperature and then stirred for 21 hours. The reaction was then cooled to 10° C. and methanol (10 ml) added. The reaction was heated to reflux for 3 hours, then concentrated in vacuo to give an orange solid. Water (50 ml) was added and stirred for two hours then left to stand overnight then 9c (0.313 g, 70%) was collected as a black solid.

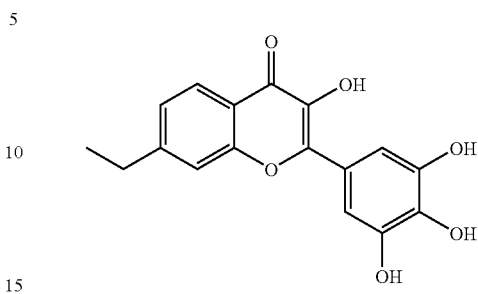

$^1$H nmr (400 MHz, D$_3$CCOCD$_3$) 1.32 (t, 3H, 7.5 Hz), 2.81-2.89 (m, 2H), 7.33 (d, 1H, 8.0 Hz), 7.48 (s, 2H), 7.53 (s, 1H), 8.04 (d, 1H, 8.0 Hz). $^{13}$C nmr (100 MHz, D$_3$CSOCD$_3$) 15.23 (CH$_3$) 28.53 (CH$_2$) 107.56 (CH) 116.64 (CH) 119.58 (Q) 121.58 (Q) 124.97 (CH) 125.15 (CH) 135.99 (Q) 138.19 (Q) 146.07 (Q) 146.13 (Q) 150.59 (Q) 154.89 (Q) 172.61 (Q) .FAB+ 315.1 (8%, [M+H]$^+$), 314.1 (5%, M$^+$) C$_{17}$H$_{15}$O$_6$ calc. 315.0869, found 315.0869.

The reaction may be summarised by the following Scheme.

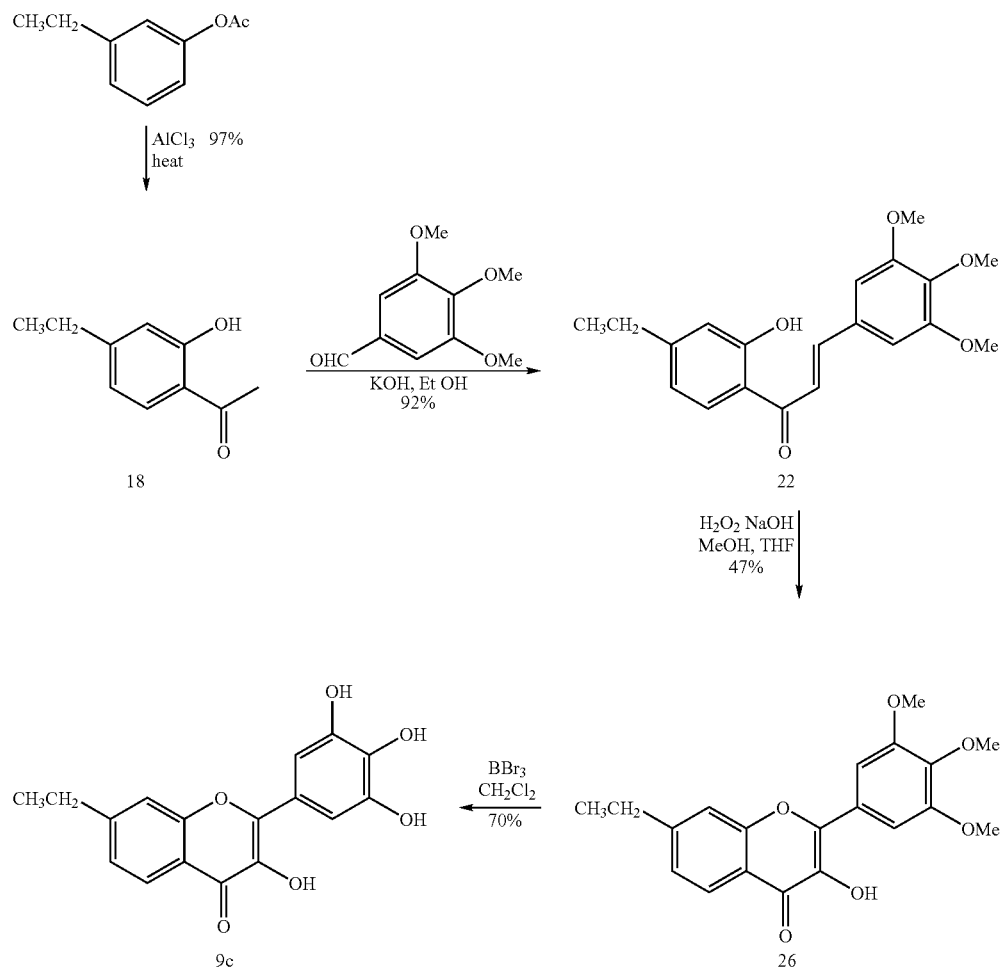

EXAMPLE 2

7-Butyl-3-hydroxy-2-(3,4,5-trihydroxyphenyl)-chromen-4-one (9d) was synthesised from 3-iodophenol (see summary in Scheme 2). The acetophenone (29) was prepared by acetylation of 3-iodophenol and Fries rearrangement as described by Chen et al. (J Chem Soc (1958) pages 146-150). Details are as follows:

2-Hydroxy-4-iodo acetophenone (29)

To a stirring solution of 3-iodo phenyl acetate (32.20 g, 123 mmol) in chlorobenzene (250 ml) under nitrogen was added aluminium chloride (31.00 g, 232 mmol, 1.9 equ). The reaction mixture was heated to 140° C. for 90 hours then allowed to cool. The reaction mixture was poured onto ice/water and then filtered, and the residue washed with dichloromethane. The filtrate was then extracted with dichloromethane and the combined organic layers extracted with 10% potassium hydroxide solution (3×100 ml). The combined aqueous layers were then acidified with 6N hydrochloric acid and extracted with dichloromethane (3×75 ml). This organic layer was then dried (MgSO$_4$) and concentrated in vacuo to give 29 (22.3 g, 69 ) as a brown solid.

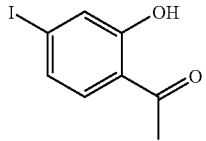

$^1$H nmr (400 MHz, CDCl$_3$). 2.60 (s, 3H) 7.26-7.28 (m, 2H) 7.42 (s, 1H) 12.26 (s, 1H). $^{13}$C nmr (100 MHz, CDCl$_3$) 26.596 (CH$_3$), 103.768 (Q), 118.997 (Q), 127.833 (CH), 128.325 (CH), 131.251 (CH), 162.191 (Q), 204.214 (Q). CI+ 263.0 (98%, M+H$^+$) 262 (100%, M$^+$). Acc.Mass. (M+H) C$_8$H$_8$O$_2$I, calc. 262.9569, found 262.9568. ir (GG) 2360 g 1699 g 1558 g 1205. mp. 51.5-52° C. (lit. 52-540° C.*).

2'-Hydroxy-4'-iodo-3,4,5-trimethoxy-chalcone (32)

To a stirring suspension of 29 (0.55 g, 2.1 mmol) and 3,4,5-trimethoxy-benzaldehyde (0.66 g, 3.4 mmol, 1.6 equ) in ethanol (10 ml) was added potassium hydroxide (0.25 g, 4.5 mmol, 2.1 equ). The reaction mixture was stirred for 119 hours then diluted with water, acidified (1N HCl) and extracted with ethyl acetate (3×70 ml). The combined organic layers were then washed with saturated aqueous sodium bicarbonate (50 ml), saturated brine (50 ml), 10% sodium bisulfite solution (3×50 ml) and then saturated brine (50 ml) again. The organic layer was then dried (MgSO$_4$) and concentrated in vacuo to give a yellow solid (1.17 g). This solid was heated in methanol, and the undissolved solid collected. The filtrate was concentrated and then heated in methanol again. More undissolved solid was collected. Undissolved solid is 32 (0.50 g, 54%).

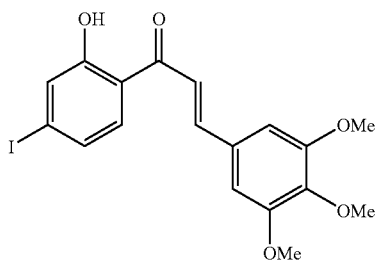

$^1$H nmr (400 MHz, CDCl$_3$) 3.92 (s, 3H) 3.94 (s, 6H) 6.88 (s; 2H) 7.30 (dd, 1.6+8 Hz, 1H) 7.42-7.47 (m, 2H) 7.59 (d, 8 Hz, 1H) 7.86 (d, 15 Hz, 1H) 12.89 (s, 1H). $^{13}$C nmr (100 MHz, CDCl$_3$) 56.268 (CH$_3$), 61.021 (CH$_3$), 103.699 (CH), 103.699 (Q), 106.054 (CH), 118.683 (CH), 119.317 (Q), 128.010 (CH), 128.128 (CH) 129.802 (Q), 130.126 (CH), 146.271 (CH), 153.519 (Q), 163.378 (Q), 193.146 (Q). EI+ 439.9 (100%, M$^+$). Acc.Mass. C$_{18}$H$_{17}$O$_5$I, calc. 440.0121, found 440.0118. ir (GG) 2360, 1716, 1684. mp 140.5-140.9° C.

3-Hydroxy-7-iodo-2-(3,4,5-trimethoxyphenyl)-chromen-4-one

To a stirring solution of 32 (0.165 g, 0.4 mmol) in methanol (4.4 ml) and 16% aqueous sodium hydroxide solution (0.6 ml, 2.4 mmol, 6.4 egu) at 0° C. was added 15% aqueous hydrogen peroxide (0.6 ml, 2.6 mmol, 7.1 equ) dropwise. The solution was stirred at 0° C. for ten minutes then sealed and placed in a refrigerator for 24 hours. The reaction was then filtered and then collected solid separated between 1N HCl and dichloromethane. The organic layer was then dried (MgSO$_4$) and concentrated to give 3-hydroxy-7-iodo-2-(3,4,5-trimethoxyphenyl)-chromen-4-one as a yellow solid. Meanwhile filtrate was acidified (1N HCl) and the precipitated solid, 3-hydroxy-7-iodo-2-(3,4,5-trimethoxyphenyl)-chromen-4-one, collected. (Total yield 0.130 g, 76%).

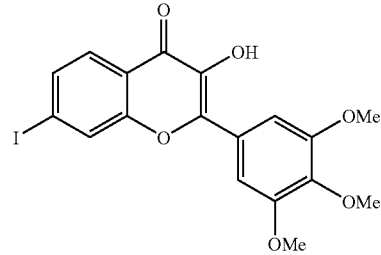

$^1$H nmr (400 MHz, CDCl$_3$) 3.95 (s, 3H) 3.97 (s, 6H) 7.03 (br s, 1H) 7.51 (s, 2H) 7.72 (dd, 1.4+8 Hz, 1H) 7.93 (d, 8 Hz, 1H) 8.05 (d, 1.4 Hz, 1H). $^{13}$C nmr (100 MHz, CDCl$_3$) 56.302 (CH$_3$), 61.011 (CH$_3$), 100.113 (Q), 105.370 (CH), 119.947 (Q), 125.788 (Q), 126.518 (CH), 127.348 (CH), 133.869 (CH) 138.331 (Q), 140.160 (Q), 144.704 (Q), 153.227 (Q), 154.780 (Q), 172.825 (Q). EI+ 453.9 (100%, M$^+$) 438.9 (25%, M–CH$_3^+$) . Acc.Mass. C$_{18}$H$_{15}$O$_6$I, calc. 453.9913, found 453.9916. ir (GG) 3749, 2360, 1734, 1265, 740. mp 151-153° C.

3-Benzyloxy-7-iodo-2-(3,4,5-trimethoxy-phenyl) chromen-4-one (34)

A stirring suspension of 3-hydroxy-7-iodo-2-(3,4,5-trimethoxyphenyl)-chromen-4-one (0.257 g, 0.6mmol), potassium carbonate (1.48 g, 11 mmol, 19 equ), potassium iodide (0.06 g, 0.3 mmol, 0.6 equ) and benzyl chloride (0.16 ml, 1.3 mmol, 2.3 equ) in acetone (12 ml) under nitrogen was heated to reflux for one hour. The reaction was filtered and the filtrate concentrated in vacuo to give an orange solid. This solid was recrystallised from isopropanol to give 34 (0.270 g, 88%) as a white solid.

The substituted flavonol 9d was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried (MgSO$_4$)

and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 9d as a fine yellow precipitate that was collected by filtration or extraction into ethyl acetate.

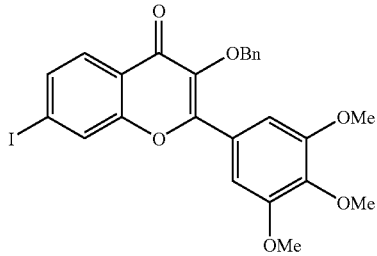

$^1$H nmr (400 MHz, CDCl$_3$) 3.79 (s, 6H) 3.95 (s, 3H) 5.15 (s, 2H) 7.28-7.30 (m, 5H) 7.35-7.37 (m, 2H) 7.76 (d, 8 Hz, 1H) 7.99-8.01 (m, 2H). $^{13}$C nmr (100 MHz, CDCl$_3$) 56.110 (CH$_3$), 60.9670 (CH$_3$), 74.493 (CH$_2$) 99.720 (Q), 106.333 (CH), 123.518 (Q), 125.565 (Q), 126.992 (CH), 127.095 (CH), 128.278 (CH) 128.830 (CH), 134.025 (CH), 136.538 (Q), 152.862 (Q), 154.796 (Q), 155.731 (Q), 174.559 (Q). EI+ 543.9 (30%, M$^+$) 452.9 (47%, M-Bn$^+$). Acc.Mass. C$_{25}$H$_{21}$O$_6$I, calc. 544.0383, found 544.0385. mp. 142° C. ir (GG) 2360, 1734, 1558, 1265, 744.

3-Benzyloxy-7-butyl-2-(3,4,5-trimethoxy-phenyl)-chromen-4-one (39d)

To a stirring solution of n-butane boronic acid (0.133 g, 1.3 mmol, 1.4 equ) and dichloropalladium (dppf) (0.050 g, 0.06 mmol, 0.07 eq) in tetrahydrofuran (7 ml) and 3M NaOH solution (1.1 ml) was added 34 (0.500 g, 0.9 mmol) added and the reaction heated to reflux for 21 hours. The reaction was then quenched with water and diethyl ether. The organic layer was collected and the aqueous layer extracted with diethyl ether (2×). The combined organic layers were washed with 1M HCl and brine then dried (MgSO$_4$) and concentrated in vacuo to give a yellow oil. A silica plug (dichloromethane) yielded 39d (0.099 g, 23%) as an orange oil.

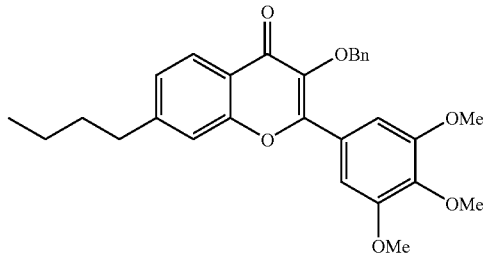

EI+ 474.2 (15%, M$^+$) C$_{29}$H$_{30}$O$_6$ Calc. 474.2042 Found 474.2041.

7-Butyl-3-hydroxy-2-(3,4,5-trihydroxy-phenyl)-chromen-4-one (9d)

To a stirring solution of 39d (0.389 g, 1 mmol) in dichloromethane (15 ml) under Ar was added boron tribromide in dichloromethane (1.0M, 5.0 ml, 5 mmol, 4.9 equ). The mixture was then stirred for 18 hours. Methanol (5 ml) was then added. The reaction was heated to reflux for 2 hours, then concentrated in vacuo to give a brown solid. Water (25 ml) was added and the mixture sonicated then extracted into ethyl acetate (3×). The organic layer was washed with brine then dried (MgSO$_4$) and concentrated in vacuo to give 9d (0.302 g, 77%) as a brown solid.

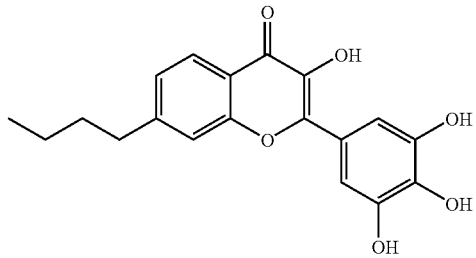

$^1$H nmr (400 MHz, CD$_3$SOCD$_3$) 0.92 (t, 3H, 7.3 Hz) 1.34 (m, 2H) 1.65 (m, 2H) 2.76 (t, 2H, 7.3 Hz) 7.30 (m, 3H) 7.48 (s, 1H) 8.00 (d, 1H, 8.1Hz). $^{13}$C nmr (100 MHz, CDCl$_3$). FAB+ 343.3 (10%, [M+H]$^+$) C$_{19}$H$_{19}$O$_6$ calc. 343.1182 found 343.1184.CHN C$_{19}$H$_{16}$O$_6$ calc. 66.66%; C, 5.30%; H, found 65.31%; C, 4.62%; H.

The reaction can be summarised as follows:

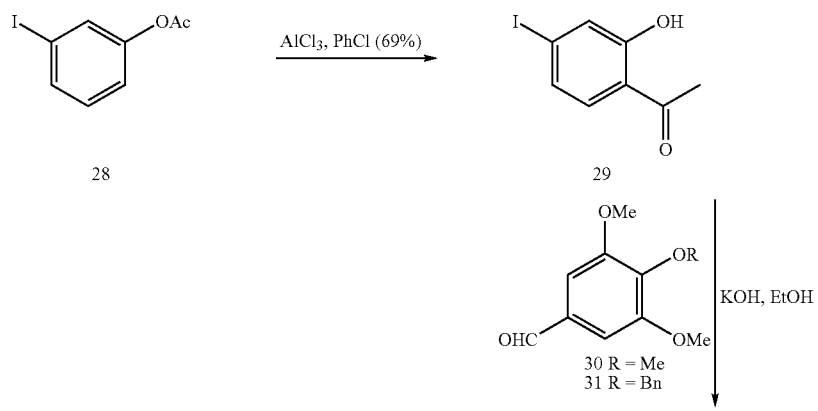

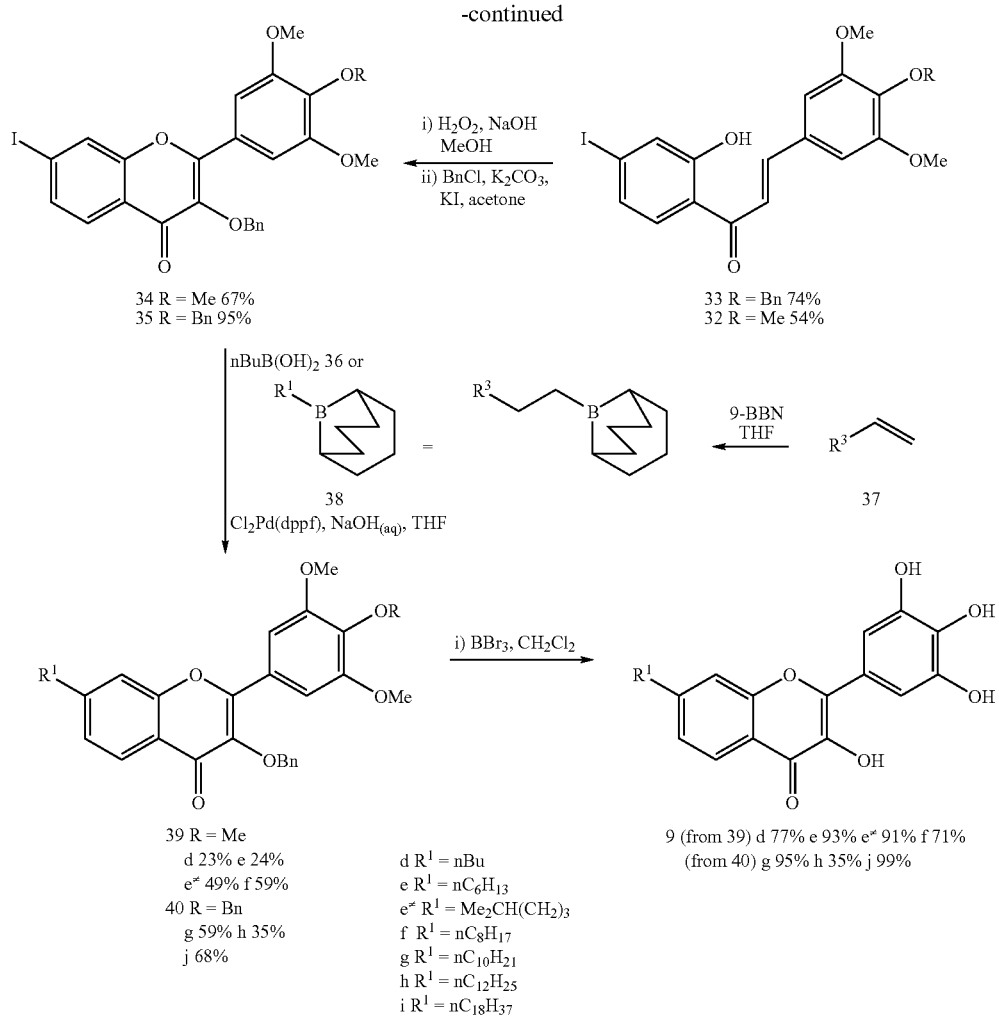

EXAMPLE 3

7-Hexyl-3-hydroxy-2-(3,4,5-trihydroxy-phenyl)-chromen-4-one (9e) was synthesised in a similar manner to that described in Example 2.

3-Benzyloxy-7-hexyl-2-(3,4,5-trimethoxy-phenyl)-chromen-4-one (39e)

To a stirring solution of 1-hexene (0.109 g, 1.3 mmol, 1.4 eq) in tetrahydrofuran (2 ml) under argon at 0° C. was added 9-BBN in tetrahydrofuran (0.5M, 2.7 ml, 1.4 mmol, 1.5 eq). The reaction was allowed to warm to room temperature and stirred for 8 hours then 34 (0.505 g, 0.9 mmol) (produced as described in Example 2) in tetrahydrofuran (5 ml), 3M NaOH solution (1.1 ml) and dichloropalladium (dppf) (0.032 g, 0.04 mmol, 0.04 eq) were added and the reaction heated to reflux for 15 hours. The reaction was then quenched with water and diethyl ether. The organic layer was collected and the aqueous layer extracted with dichloromethane. The combined organic layers were dried (MgSO$_4$) and concentrated in vacuo to give a brown oil. Column chromatography (silica gel, DCM) yielded 39e (0.112 g, 24%) as a colourless oil.

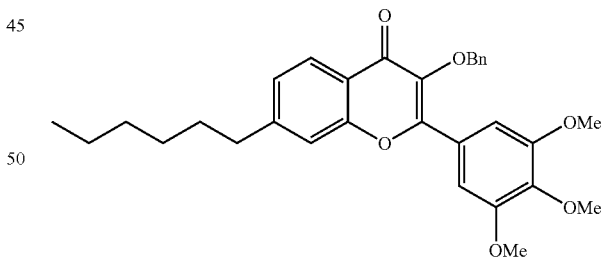

$^1$H nmr (400 MHz, CDCl$_3$) 0.89 (t, 3H, 6.5 Hz) 1.30-1.42 (m, 6H) 1.66-1.73 (m, 2H) 2.76 (t, 2H, 7.5 Hz) 3.78 (s, 6H) 3.93 (s, 3H) 5.13 (s, 2H) 7.23-7.37 (m, 9H) 8.19 (d, 1H, 8.1 Hz). $^{13}$C nmr (100 MHz, CDCl$_3$) 14.45 (CH$_3$) 22.94 (CH$_2$) 29.30 (CH$_2$) 31.35 (CH$_2$) 32.03 (CH$_2$) 32.44 (CH$_2$) 36.50 (CH$_2$) 56.52 (CH$_3$) 61.35 (CH$_3$) 74.87 (CH$_2$) 106.76 (CH) 117.38 (CH) 122.48 (Q) 125.98 (CH) 126.11 (CH) 126.58 (Q) 128.55 (CH) 128.64 (CH) 12.9.25 (CH) 137.23 (Q) 140.30 (Q) 140.48 (Q) 150.22 (Q) 153.23 (Q) 155.75 (Q) 155.92 (Q) 175.38 (Q) . EI+ 502.6 (35%, M$^+$) 411.5 (43%, [M−Bn]$^+$) C$_{31}$H$_{34}$O$_6$ Calc. 502.2355 Found 502.2354.

7-Hexyl-3-hydroxy-2-(3,4,5-trihydroxy-phenyl)-chromen-4-one (9e)

To a stirring solution of 39e (0.096 g, 0.2 mmol) in dichloromethane (10 ml) under Ar at 0° C. was added boron tribromide in dichloromethane (1.0M, 1.0 ml, 1.0 mmol, 5.2 equ). The mixture was warmed to room temperature and then stirred for 15 hours. Methanol (5 ml) was then added. The reaction was heated to reflux for 100 minutes, then concentrated in vacuo to give a red solid. Water (20 ml) was added and the mixture sonicated then left to stand overnight then 9e (0.066 g, 93%) was collected as a yellow solid.

The substituted flavonol 9e was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried ($MgSO_4$) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 9e as a fine yellow precipitate that was collected by filtration or extraction into ethyl acetate.

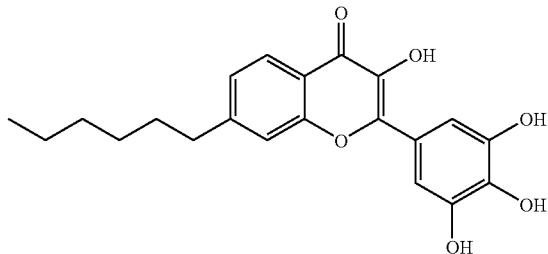

$^1$H nmr (400 MHz, $CD_3SOCD_3$) 0.86 (t, 3H, 6.0 Hz) 1.27-1.33 (m, 6H) 1.61-1.68 (m, 2H) 2.75 (t, 2H, 7.5 Hz) 7.28-7.33 (m, 3H) 7.48 (s, 1H) 7.99 (d, 1H, 8.1 Hz) 8.79 (s, 1H) 9.21 (m, 3H). $^{13}$C nmr (100 MHz, $D_3CSOCD_3$) 14.29 ($CH_3$) 22.35 ($CH_2$) 28.60 ($CH_2$) 30.64 ($CH_2$) 31.39 ($CH_2$) 35.42 ($CH_2$) 107.56 (CH) 117.24 (CH) 119.57 (Q) 121.56 (Q) 124.91 (CH) 125.56 (CH) 135.98 (Q) 138.18 (Q) 146.06 (Q) 146.06 (Q) 149.298 (Q) 154.81 (Q) 172.62 (Q). EI+ 370.1 (100%, M$^+$) $C_{21}H_{22}O_6$ calc. 370.1416 found 370.1414.

EXAMPLE 4

7-Octyl-3-hydroxy-2-(3,4,5-trihydroxy-phenyl)-chromen-4-one (Compound 9f) was prepared analogously to Examples 2 and 3.

3-Benzyloxy-7-octyl-2-(3,4,5-trimethoxy-phenyl)-chromen-4-one (39f)

To a stirring solution of 1-octene (0.148 g, 1.3 mmol, 1.4 eq) in tetrahydrofuran (2 ml) under argon at 0° C. was added 9-BBN in tetrahydrofuran (0.5M, 2.7 ml, 1.4 mmol, 1.5 eq). The reaction was allowed to warm to room temperature and stirred for 9 hours then 34 (0.504 g, 0.9 mmol) (produced as described in Example 2) in tetrahydrofuran (5 ml), 3M NaOH solution (1.1 ml) and dichloropalladium (dppf) (0.031 g, 0.04 mmol, 0.04 eq) were added and the reaction heated to reflux for 15 hours. The reaction was then quenched with water and diethyl ether. The organic layer was collected and the aqueous layer extracted with dichloromethane. The combined organic layers were washed with brine dried ($MgSO_4$) and concentrated in vacuo to give a orange oil. Column chromatography (silica gel, DCM) yielded 39f (0.290 g, 59%) as a colourless oil.

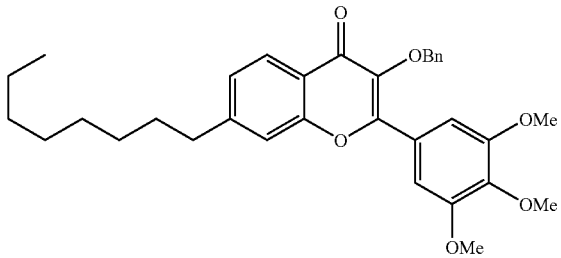

$^1$H nmr (400 MHz, $CDCl_3$) 0.88 (t, 3H, 7.0 Hz) 1.25-1.41 (m, 10H) 1.62-1.74 (m, 2H) 2.76 (t, 2H, 7.5 Hz) 3.78 (s, 6H) 3.89 (s, 3H) 5.13 (s, 2H) 7.21-7.37 (m, 9H) 8.19 (d, 1H, 8.2 Hz). $^{13}$C nmr (100 MHz, $CDCl_3$) 14.48 ($CH_3$) 23.03 ($CH_2$) 29.59 ($CH_2$) 29.65 ($CH_2$) 29.80 ($CH_2$) 31.40 ($CH_2$) 32.30 ($CH_2$) 36.51 ($CH_2$) 56.52 ($CH_3$) 61.35 ($CH_3$) 74.87 ($CH_2$) 106.76 (CH) 117.38 (CH) 122.48 (Q) 125.98 (CH) 126.11 (CH) 126.58 (Q) 128.55 (CH) 128.64 (CH) 129.25 (CH) 137.23 (Q) 140.30 (Q) 140.49 (Q) 150.22 (Q) 153.23 (Q) 155.75 (Q) 155.91 (Q) 175.37 (Q). CI+ 531.3 (22%, [M+H]$^+$) $C_{33}H_{39}O_6$ Calc. 531.2747 Found 531.2744.

7-Octyl-3-hydroxy-2-(3,4,5-trihydroxy-phenyl)-chromen-4-one (9f)

To a stirring solution of 39f (0.290 g, 0.5 mmol) in dichloromethane (10 ml) under Ar at 0° C. was added boron tribromide in dichloromethane (1.0M, 2.7 ml, 2.7 mmol, 4.9 equ). The mixture was warmed to room temperature and then stirred for 16 hours. Methanol (5 ml) was then added. The reaction was heated to reflux for 2 hours, then concentrated in vacuo to give a red solid. Water (25 ml) was added and the mixture sonicated then left to stand overnight. 9f (0.155 g, 71%) was collected as a yellow solid.

The substituted flavonol 9f was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried ($MgSO_4$) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 9f as a fine yellow precipitate that was collected by filtration or extraction into ethyl acetate.

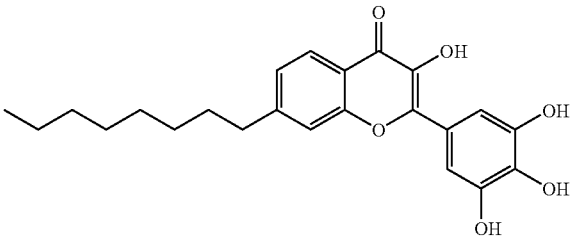

$^1$H nmr (400 MHz, $CD_3SOCD_3$) 0.85 (t, 3H, 6.5 Hz) 1.24-1.30 (m, 10H) 1.63-1.87 (m, 2H) 2.75 (t, 2H, 7.6 Hz) 7.28-7.34 (m, 3H) 7.48 (s, 1H) 7.99 (d, 1H, 8.2 Hz) 8.79 (8, 1H) 9.20 (s, 3H). $^{13}$C nmr (100 MHz, $D_3CSOCD_3$) 14.29 ($CH_3$)

22.41 ($CH_2$) 28.95 ($CH_2$) 29.13 ($CH_2$) 29.13 ($CH_2$) 30.66 ($CH_2$) 31.60 ($CH_2$) 35.42 ($CH_2$) 107.56 (CH) 117.24 (CH) 119.58 (Q) 121.57 (Q) 124.91 (CH) 125.53 (CH) 135.98 (Q) 138.19 (Q) 146.06 (Q) 146.06 (Q) 149.27 (Q) 154.80 (Q) 172.61 (Q). EI+ 398 (16%, $M^+$) $C_{23}H_{26}O_6$ calc. 398.1729 found 398.1733.

EXAMPLE 5

7-(4-Methyl-pentyl)-3-hydroxy-2-(3,4,5-trihydroxyphenyl)-chromen-4-one (compound 9e*) has a short branched chain and was prepared using a similar methodology to Example 2.

3-Benzyloxy-7-(4-methyl-pentyl)-2-(3,4,5-trimethoxy-phenyl)-chromen-4-one (39e*)

To a stirring solution of 4-methyl pent-1-ene (0.110 g, 1.3 mmol, 1.4 eq) in tetrahydrofuran (2 ml) under argon at 0° C. was added 9-BBN in tetrahydrofuran (0.5M, 2.7 ml, 1.4 mmol, 1.5 eq). The reaction was allowed to warm to room temperature then stirred for 6 hours then 34 (0.499 g, 0.9 mmol) (prepared as described in Example 2) in tetrahydrofuran (5 ml), 3M NaOH solution (1.1 ml) and dichloropalladium (dppf) (0.028 g, 0.03 mmol, 0.04 eq) were added and the reaction heated to reflux for 14 hours. The reaction was then quenched with water and diethyl ether. The organic layer was collected and the aqueous layer extracted with diethyl ether (2×). The combined organic layers were washed with 1M HCl and brine then dried ($MgSO_4$) and concentrated in vacuo to give a yellow oil. A silica plug (dichloromethane) yielded 39e* (0.197 g, 49%) as a yellow oil.

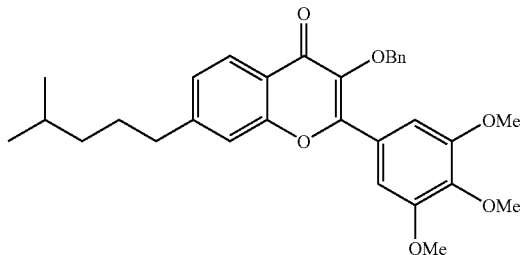

EI+ 502.3 (6%, $M^+$) $C_{31}H_{34}O_6$ Calc. 502.2355 Found 502.2358.

7-(4-Methyl-pentyl)-3-hydroxy-2-(3,4,5-trihydroxyphenyl)-chromen-4-one (9e*)

To a stirring solution of 39e* (0.184 g, 0.4 mmol) in dichloromethane (20 ml) under Ar at 0° C. was added boron tribromide in dichloromethane (1.0M, 1.8 ml, 1.8 mmol, 5 equ). The mixture was warmed to room temperature and then stirred for 15 hours. Methanol (10 ml) was then added. The reaction was heated to reflux for 2 hours, then concentrated in vacuo to give a brown solid. Water (20 ml) was added and the mixture sonicated then left to stand overnight. 9e* (0.124 g, 91%) was then collected as a yellow solid.

The substituted flavonol 9e* was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried ($MgSO_4$) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 9e* as a fine yellow precipitate that was collected by filtration or extraction into ethyl acetate.

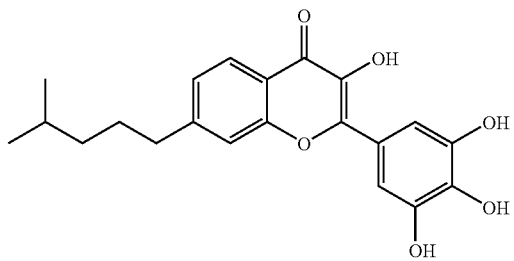

$^1$H nmr (400 MHz, $CD_3SOCD_3$) 0.86 (d, 6H, 6.6 Hz) 1.18-1.24 (m, 2H) 1.51-1.67 (m, 3H) 2.74 (t, 2H, 7.5 Hz) 7.30-7.33 (m, 3H) 7.48 (s, 1H) 7.99 (d, 1H, 8.0 Hz) 8.80 (s, 1H) 9.22 (s, 3H). $^{13}$C nmr (100 MHz, $D_3CSOCD_3$) 22.82 ($CH_3$) 27.64 (CH) 28.26 ($CH_2$) 35.66 ($CH_2$) 38.29 ($CH_2$) 107.56 (CH) 117.24 (CH) 119.59 (Q) 121.56 (Q) 124.92 (CH) 125.54 (CH) 135.98 (Q) 138.20 (Q) 146.07 (Q) 146.07 (Q) 149.29 (Q) 154.81 (Q) 172.61 (Q). EI+ 370.1 (100%, $^{M+}$) $C_{21}H_{22}O_6$ calc. 370.1416 found 370.1411.

EXAMPLE 6

7-Decyl-3-hydroxy-2-(3,4,5-trihydroxy-phenyl)-chromen-4-one (compound 9g) was prepared as follows:

2-hydoxy-4-iodo acetophenone (29) was prepared as described in Example 2.

4-Benzyloxy-3,5-dimethoxy-benzaldehyde (31)

To a stirring suspension of syringaldehyde (25.19 g, 138 mmol) and potassium carbonate (38.14 g, 276 mmol, 2 equ) in N,N-dimethyl formamide (500 ml) was added benzyl bromide (20 ml, 168 mmol, 1.2 equ). The reaction was stirred for 25 hours, then poured into dichloromethane. The organic solvent was washed with water (5×) then dried ($MgSO_4$) and concentrated in vacuo to give a pink oil. This was recrystallised from hexane to give 31 (32.9 g, 87 %).

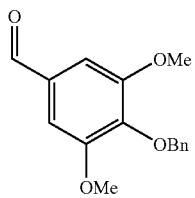

$^1$H nmr (400 MHz, $CDCl_3$) 3.92 (s, 6H) 5.15 (s, 2H) 7.13 (a, 2H) 7.28-7.38 (m, 3H) 7.48 (d, 2H, 7.4 Hz) 9.91 (s, 1H). $^{13}$C nmr (100 MHz, $CDCl_3$) 56.638 ($CH_3$) 75.428 ($CH_2$) 105.085 (CH) 128.479 (CH) 128.615 (CH) 128.803 (CH) 132.286 (Q) 137.591 (Q) 142.790 (Q) 154.384 (Q) 191.491 (CH). EI+ 272.0 (15%) M, 91.1 (100%) Bn. $C_{16}H_{16}O_4$ calc. 272.1049, obs. 272.1053. mp 56-57° C.

2'-Hydroxy-4'-iodo-4-benzyloxy-3,5-dimethoxy chalcone (33)

To a stirring suspension of 29 (0.73 g, 2.8 mmol) and 31 (0.911 g, 3.3 mmol, 1.2 equ) in ethanol (10 ml) was added potassium hydroxide (0.42 g, 7.5 mmol, 2.7 equ). The reaction mixture was stirred for 46 hours then diluted with water, acidified (2N HCl) and extracted with ethyl acetate (3×). The organic layer was then dried ($MgSO_4$) and concentrated in vacuo to give a brown oil. This solid was recrystallised from methanol to give 33 (1.06 g, 74%) as yellow crystals.

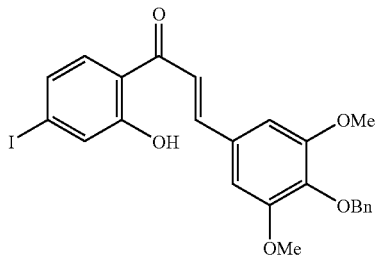

¹H nmr (400 MHz, CDCl₃) 3.89 (s, 6H) 5.09 (s, 2H) 6.85 (s, 2H) 7.25-7.49 (m, 7H) 7.57 (d, 1H, 8.5 Hz) 7.83 (d, 1H, 15 Hz) 12.91 (s, 1H). ¹³C nmr (100 MHz, CDCl₃) 56.668 (CH₃) 75.534 (CH₂) 104.096 (Q) 106.543 (CH) 119.064 (CH) 119.757 (Q) 128.424 (CH) 128.547 (CH) 128.607 (CH) 128.843 (CH) 130.360 (Q) 130.549 (CH) 137.792 (Q) 140.340 (Q) 146.746 (CH) 154.256 (Q) 163.807 (Q) 193.575 (Q). EI+ 516.0 (42 %, M⁺), 425.0 (74%, [M−Bn]⁺) 91.0 (100%, B⁺). C₂₄H₂₁IO₅ cald. 516.0434, obs. 516.0433. mp 123.6-124.6° C. (MeOH).

3-Hydroxy-7-iodo-(4-benzyloxy-3,5-dimethoxyphenyl)-chromen-4-one

To a stirring solution of 33 (0.85 g, 1.6 mmol) in methanol (17 ml) and 16% aqueous sodium hydroxide solution (2.2 ml, 8.8 mmol, 5.3 equ) at 0° C. was added 15% aqueous hydrogen peroxide (2.2 ml, 9.7 mmol, 5.9 equ) dropwise. The solution was stirred at 0° C. for ten minutes then sealed and placed in a refrigerator for 24 hours. The reaction was then acidified (1N HCl) and extracted with dichloromethane (2×). The organic layer was then dried (MgSO₄) and concentrated to give a dark yellow foam. This was triturated with ethanol to give 3-hydroxy-7-iodo-(4-benzyloxy-3,5-dimethoxyphenyl)-chromen-4-one (0.84 g, 96%) as a yellow solid.

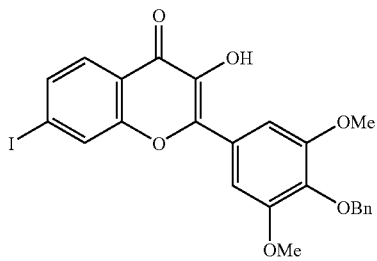

¹H nmr (400 MHz, CDCl₃) 3.93 (s, 6H) 5.12 (s, 2H) 7.04 (brs, 1H) 7.28-7.38 (m, 3H) 7.49-7.52 (m, 4H) 7.72 (dd, 1H, 1.4+8.4 Hz) 7.92 (d, 1H, 8.4 Hz) 8.03 (d, 1H 1.4 Hz). EI+ 530.0 (22%) M, 425.0 (100%) M−Bn, 91.1 (35%) Bn. C₂₄H₁₉IO₆ calc. 530.0226, obs. 530.0234. mp 169-171° C. (EtOH).

3-Benzyloxy-7-iodo-2-(4-benzyloxy-3,5-dimethoxyphenyl)chromen-4-one (35)

A stirring suspension of 3-hydroxy-7-iodo-(4-benzyloxy-3,5-dimethoxyphenyl)-chromen-4-one (5 g, 9 mmol), potassium carbonate (6.2 g, 45 mmol, 4.8 equ), potassium iodide (0.64 A, 4 mmol, 0.4 equ) and benzyl chloride (1.7 ml, 15 mmol, 1.6 equ) in acetone (150 ml) under nitrogen was heated to reflux for 19 hours. The reaction was filtered and the filtrate concentrated in vacuo to give an cream solid. This solid was recrystallised from isopropanol to give 35 (5.77 g, 99%) as a white solid.

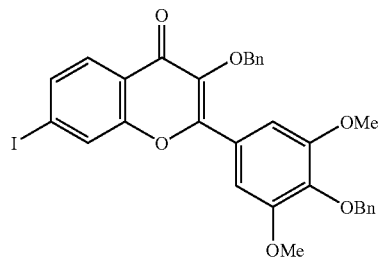

¹H nmr (400 MHz, CDCl₃) 3.73 (s, 6H) 5.11 (s, 2H) 7.21 (s, 2H) 7.26-7.37 (m, 8H) 7.49 (d, 2H, 7 Hz) 7.73 (d, 1H, 8 Hz) 7.97 (m, 2H). ¹³C nmr (100 MHz, CDCl₃) 56.514 (CH₃) 74.869 (CH₂) 75.438 (CH₂) 100.103 (Q) 106.777 (CH) 123.930 (Q) 126.104 (Q) 127.400 (CH) 127.507 (CH) 128.597 (CH) 128.675 (CH) 128.693 (CH) 128.875 (CH) 129.272 (CH) 134.421 (CH) 136.926 (Q) 137.831 (Q) 139.591 (Q) 140.456 (Q) 153.595 (Q) 155.209 (Q) 156.219 (Q) 174.973 (Q).

EI+ 620.0 (20%) M, 528.9 (20%), 91.1 (100%) Bn. C₃₁H₂₅IO₆ calc. 620.0696, obs. 620.0695. mp 131-133° C.

3-Benzyloxy-2-(4-benzyloxy-3,5-dimethoxy-phenyl)-7-decyl-chromen-4-one (40g)

To a stirring solution of 1-decene (0.176 g, 1.3 mmol, 1.4 eq) in tetrahydrofuran (2 ml) under argon was added 9-BBN in tetrahydrofuran (0.5M, 2.7 ml, 1.4 mmol, 1.5 eq). The reaction was stirred for 6 hours then 35 (0.560 g, 0.9 mmol) in tetrahydrofuran (5 ml), 3M NaOH solution (1.1 ml) and dichloropalladium (dppf) (0.027 g, 0.03 mmol, 0.04 eq) were added and the reaction heated to reflux for 15 hours. The reaction was then quenched with water and diethyl ether. The organic layer was collected and the aqueous layer extracted with dichloromethane. The combined organic layers were dried (MgSO₄) and concentrated in vacuo to give a brown oil. Column chromatography (silica gel, DCM) yielded 40 g (0.339 g, 59%) as a pale yellow oil.

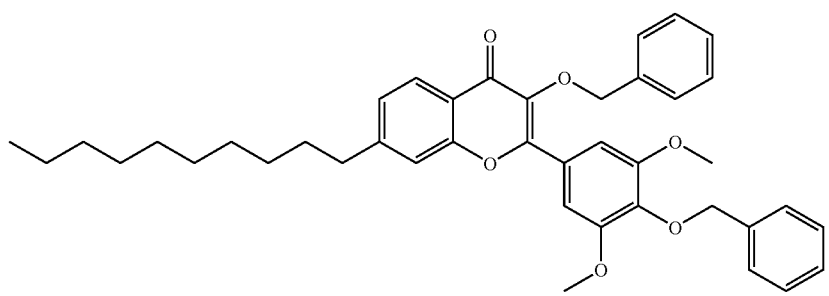

¹H nmr (400 MHz, CDCl₃) 0.88 (t, 3H, 7 Hz) 1.26-1.42 (m, 14H) 1.65-1.74 (m, 2H) 2.75 (t, 2H, 7 Hz) 3.74 (s, 6H) 5.10 (s, 2H) 5.11 (s, 2H) 7.20-7.38 (m, 12H) 7.49-7.51 (m, 2H) 8.18 (d, 1H, 8 Hz). ¹³C nmr (100 MHz, CDCl₃) 14.11 (CH₃) 22.68 (CH₂) 29.27 (CH₂) 29.31 (CH₂) 29.46 (CH₂) 29.55 (CH₂) 29.60 (CH₂) 31.01 (CH₂) 31.89 (CH₂) 36.13 (CH₂) 56.14 (CH₃) 74.46 (CH₂) 75.06 (CH₂) 106.41 (CH) 117.00 (CH) 122.09 (Q) 125.60 (CH) 125.72 (CH) 126.31 (Q) 128.00 (Q) 128.17 (CH) 128.21 (CH) 128.26 (CH) 128.51 (CH) 128.90 (CH) 136.82 (Q) 137.52 (Q) 138.24 (Q) 139.99 (Q) 149.82 (Q) 153.16 (Q) 155.37 (Q) 155.60 (Q) 175.01 (Q). FAB+ 635.2 (25%, [M+H]⁺) 91.5 (100%, Bn⁺) $C_{41}H_{47}O_6$ Calc. 635.3373 Found 635.3370.

7-Decyl-3-hydroxy-2-(3,4,5-trihydroxy-phenyl)-chromen-4-one (9g)

To a stirring solution of 40 g (0.335 g, 0.5 mmol) in dichloromethane (25 ml) under Ar at 0° C. was added boron tribromide in dichloromethane (1.0M, 5 ml, 5 mmol, 9.5 equ). The mixture was warmed to room temperature and then stirred for 20 hours. The reaction was then cooled to 0° C. and methanol (15 ml) added. The reaction was heated to reflux for 3 hours, then concentrated in vacuo to give an orange solid. Water (75 ml) was added and sonicated then left to stand overnight then 9 g (0.213 g, 95%) was collected as a yellow solid.

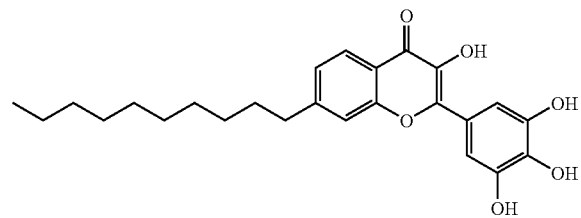

¹H nmr (400 MHz, CD₃COCD₃) 0.88 (m, 3H) 1.26-1.47 (m, 14H) 1.75 (m, 2H) 2.78 (m, 2H) 7.34 (d, 1H, 8.0 Hz) 7.49 (s, 2H) 7.54 (s, 1H) 7.87 (brs, 1H) 7.93 (brs, 1H) 8.05 (d, 1H, 8.0 Hz) 8.19 (s, 2H). ¹³C nmr (100 MHz, D₃CSOCD₃) 14.28 (CH₃) 22.43 (CH₂) 28.90 (CH₂) 29.02 (CH₂) 29.14 (CH₂) 29.28 (CH₂) 29.30 (CH₂) 30.64 (CH₂) 31.62 (CH₂) 35.42 (CH₂) 107.56 (CH) 117.23 (CH) 119.59 (Q) 121.58 (Q) 124.90 (CH) 125.52 (CH) 135.98 (Q) 138.20 (Q) 146.06 (Q) 146.11 (Q) 149.25 (Q) 154.81 (Q) 172.60 (Q). FAB+ 427.2 (100%, [M+H]⁺) $C_{25}H_{31}O_6$ calc. 427.2121 found 427.2122. CHN $C_{25}H_{30}O_6$ calc. 70.18%; C, 7.31%; H, found 71.96%; C, 7.42%; H.

EXAMPLE 7

3-Hydroxy-2-(3,4,5-trihydroxy-phenyl)-7-dodecyl-chromen-4-one (compound 9h) was prepared analogously to Example 6.

3-Benzyloxy-7-dodecyl-2-(4-benzyloxy-3,5-dimethoxy-phenyl)-chromen-4-one (40h)

To a stirring solution of 1-dodecene (0.214 g, 1.27 mmol, 1.4 eq) in tetrahydrofuran (2 ml) under argon was added 9-BBN in tetrahydrofuran (0.5M, 2.7 ml, 1.35 mmol, 1.5 eq). The reaction was stirred for 6 hours then 31 (prepared as in Example 6) (0.565 g, 0.9 mmol) in tetrahydrofuran (5 ml), 3M NaOH solution (1.1 ml) and dichloropalladium (dppf) (0.024 g, 0.03 mmol, 0.03 eq) were added and the reaction heated to reflux for 15 hours. The reaction was then quenched with 3 N HCl (B ml), diluted with water and extracted into ethyl acetate (3×). The combined aqueous layers were dried (MgSO₄) and concentrated in vacuo to give a yellow oil. Column chromatography (silica gel, DCM>DCM:MeOH 99:1) yielded 40h (0.210 g, 35%) as a pale yellow oil.

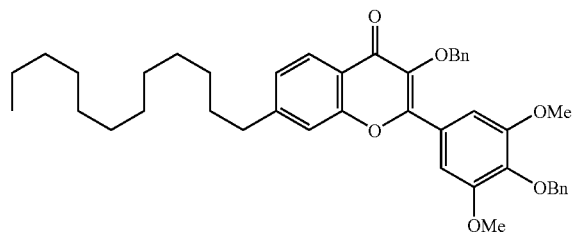

¹H nmr (400 MHz, CDCl₃) 0.85-0.89 (m, 3H) 1.20-1.37 (m, 16H) 1.51-1.56 (m, 2H) 1.62-1.71 (m, 2H) 2.75 (t, 2H, 7.4 Hz) 3.74 (s, 6H) 5.11 (s, 2H) 5.11 (s, 2H) 7.23-7.38 (m, 13H) 7.50 (dd, 1H, 1.5+6.7 Hz) 8.19 (d, 1H, 8.2 Hz). ¹³C nmr (100 MHz, CDCl₃) 14.12 (CH₃) 22.69 (CH₂) 25.75 (CH₂) 27.43 (CH₂) 29.28 (CH₂) 29.35 (CH₂) 29.47 (CH₂) 29.56 (CH₂) 29.64 (CH₂) 31.02 (CH₂) 31.92 (CH₂) 36.14 (CH₂) 56.15 (CH₃) 74.46 (CH₂) 75.06 (CH₂) 106.42 (CH) 118.00 (CH) 122.10 (Q) 125.60 (CH) 125.73 (CH) 126.32 (Q) 128.01 (CH) 128.16 (CH) 128.21 (CH) 128.27 (CH) 128.51 (CH) 128.90 (CH) 136.83 (Q) 137.53 (Q) 138.94 (Q) 139.88 (Q) 149.82 (Q) 153.17 (Q) 155.37 (Q) 155.61 (Q) 175.00 (Q). EI+ 662.3 (9%, M⁺) 571.2 (12%, [M−3n]⁺) 91.1 (100%, Bn⁺) $C_{43}H_{50}O_6$ Calc. 662.3607 Found 662.3600. $C_{42}{}^{13}CH_{50}O_6$ Calc. 663.3641 Found 663.3636.

3-Hydroxy-2-(3,4,5-trihydroxy-phenyl)-7-dodecyl-chromen-4-one (9h)

To a stirring solution of 40 h (0.058 g, 0.09 mmol) in dichloromethane (2.5 ml) under nitrogen at 0° C. was added boron tribromide (1.0M in DCM, 2.25 ml, 24 eq). The reaction was then warmed to room temperature and stirred for 19 hours. The mixture was then cooled to 0° C., methanol (2 ml) added heated to reflux for 2 hours. The reaction was then cooled and concentrated in vacuo to give a solid that was chromatographed (silica gel, dichloromethane:methanol, 9:1) to give 9 h (0.030 g, 69%) as a waxy solid.

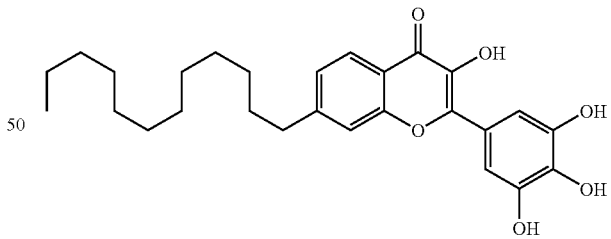

¹H nmr 400 MHz, CD₃SOCD₃) 0.84 (t, 3H, 6.4 Hz) 1.18-1.34 (m, 18H) 1.62-1.71 (m, 2H) 2.75 (t, 2H, 7.4 Hz) 7.27-7.30 (m, 3H) 7.47 (s, 1H) 7.99 (d, 1H, 8.1 Hz). ¹³C nmr (100 MHz, D₃CSOCD₃) 14.28 (CH₃) 22.42 (CH₂) 28.87 (CH₂) 29.02 (CH₂) 29.11 (CH₂) 29.24 (CH₂) 29.33 (CH₂) 30.63 (CH₂) 31.61 (CH₂) 35.41 (CH₂) 107.56 (CH) 117.24 (CH) 119.58 (Q) 121.57 (Q) 124.90 (CH) 125.53 (CH) 135.99 (Q) 138.20 (Q) 146.06 (Q) 149.27 (Q) 154.81 (Q) 172.62 (Q). EI+ 454.2 (29%, M⁺) $C_{27}H_{34}O_6$ calc. 454.2355 found 454.2353. FAB+ 455.2 (51%, [M+H]⁺) $C_{27}H_{35}O_6$ calc. 455.2434 found 455.2438.

EXAMPLE 8

3-Hydroxy-7-octadecyl-2-(3,4,5-trihydroxy-phenyl)-chromen-4-one (compound 9j) was prepared analogously to Example 6.

3-Benzyloxy-2-(4-benzyloxy-3,5-dimethoxy-phenyl)-7-octadecyl-chromen-4-one (40j)

To a stirring solution of 1-octadecene (0.322 g, 1.3 mmol, 1.4 eq) in tetrahydrofuran (2 ml) under argon was added 9-BBN in tetrahydrofuran (0.5M, 2.7 ml, 1.4 mmol, 1.5 eq). The reaction was stirred for 6 hours then 35 (prepared as described in Example 6) (0.558 g, 0.9 mmol) in tetrahydrofuran (5 ml), 3M NaOH solution (1.1 ml) and dichloropalladium (dppf) (0.025 g, 0.03 mmol, 0.04 eq) were added and the reaction heated to reflux for 18 hours. The reaction was then quenched with water and diethyl ether. The organic layer was collected and the aqueous layer extracted with dichloromethane. The combined organic layers were washed with brine, dried (MgSO$_4$) and concentrated in vacuo to give a brown oil that crystallised on standing. Column chromatography (silica gel, DCM) yielded 40j (0.455 g, 68%) as a white solid.

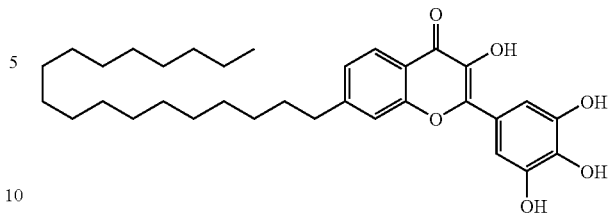

$^1$H nmr (400 MHz, CD$_3$SOCD$_3$) 0.84 (t, 3H, 6.2 Hz) 1.18-1.33 (m, 30H) 1.62-1.70 (m, 2H) 2.73 (d, 2H, 6.9 Hz) 7.23-7.30 (m, 3H) 7.46 (s, 1H) 7.99 (d, 1H, 8.1 Hz) 9.18 (s, 3H). $^{13}$C nmr (100 MHz, D$_3$CSOCD$_3$) 14.28 (CH$_3$) 22.43 (CH$_2$) 28.92 (CH$_2$) 29.04 (CH$_2$) 29.14 (CH$_2$) 29.26 (CH$_2$) 29.33 (CH$_2$) 30.67 (CH$_2$) 31.63 (CH$_2$) 35.43 (CH$_2$) 107.56 (CH) 117.22 (CH) 119.59 (Q) 121.58 (Q) 124.90 (CH) 125.48 (CH) 135.97 (Q) 138.20 (Q) 146.06 (Q) 146.10 (Q) 149.22 (Q) 154.81 (Q) 172.59 (Q). FAB+ 539.0 (100%, [M+H]$^+$)

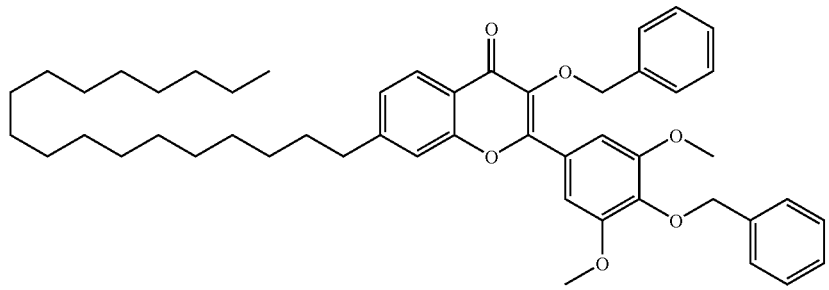

$^1$H nmr (400 MHz, CDCl$_3$) 0.88 (t, 3H, 7 Hz) 1.25-1.39 (m, 30H) 1.69-1.70 (m, 2H) 2.75 (t, 2H, 7.3 Hz) 3.74 (s, 6H) 5.10 (s, 2H) 5.11 (s, 2H) 7.21-7.38 (m, 12H) 7.50 (d, 2H, 6.7 Hz) 8.18 (d, 1H, 8 Hz). $^{13}$C nmr (100 MHz, CDCl$_3$) 14.12 (CH$_3$) 22.70 (CH$_2$) 29.30 (CH$_2$) 29.37 (CH$_2$) 29.48 (CH$_2$) 29.57 (CH$_2$) 29.67 (CH$_2$) 29.70 (CH$_2$) 31.03 (CH$_2$) 31.93 (CH$_2$) 36.14 (CH$_2$) 56.14 (CH$_3$) 74.46 (CH$_2$) 75.06 (CH$_2$) 106.40 (CH) 117.00 (CH) 122.20 (Q) 125.60 (CH) 125.81 (CH) 126.33 (Q) 128.01 (CH) 128.17 (CH) 128.21 (CH) 128.26 (CH) 128.51 (CH) 128.90 (CH) 140.00 (Q) 149.96 (Q) 153.16 (Q) 155.74 (Q) 174.93 (Q). FAB+ 747.3 (226, [M+H]$^+$) 91.5 (100%, Bn$^+$) C$_{49}$H$_{63}$O$_6$ Calc. 747.4625 Found 747.4622.

3-Hydroxy-7-octadecyl-2-(3,4,5-trihydroxy-phenyl)-chromen-4-one (9j)

To a stirring solution of 40j (0.455 g, 0.6 mmol) in dichloromethane (25 ml) under Ar at 0° C. was added boron tribromide in dichloromethane (1.0M, 6 ml, 6 mmol, 9.8 equ). The mixture was warmed to room temperature and then stirred for 22 hours. The reaction was then cooled to 0° C. and methanol (25 ml) added. The reaction was heated to reflux for 2 hours, then concentrated in vacuo to give a yellow solid. Water (50 ml) was added and sonicated then left to stand overnight then 9j (0.325 g, 99%) was collected as a yellow solid.

C$_{33}$H$_{47}$O$_6$ calc. 539.3373 found 539.3367. CHN C$_{33}$H$_{46}$O$_6$ calc. 73.57%; C, 8.61%; H, found 73.05%; C, 9.04%; H.

EXAMPLE 9

The branched chain flavonoid 7-(3,7-dimethyl-octyl-3-hydroxy-2-(3,4,5-trihydroxy-phenyl)-chromen-4-one (compound 9g*) was synthesised as follows:

3,7-Dimethyl-octan-1-ol (43)

A flask containing a stirring suspension of geraniol (10 ml, 58 mmol) and palladium on carbon (10% Pd, 0.494 g, 0.08 eq) in ethanol (70 ml) was evacuated, and then filled with hydrogen. The reaction mixture was then stirred under an atmosphere of hydrogen for 21 hours. After this time the reaction was filtered and the filtrate concentrated in vacuo to give 43 (5 g, 55%) as a colourless oil.

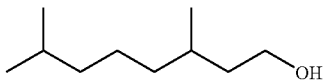

$^1$H nmr (400 MHz, CDCl$_3$) 0.86-0.90 (m, 10H) 1.11-1.42 (m, 6H) 1.49-1.68 (m, 3H) 3.63-3.73 (m, 2H).
$^{13}$C nmr (100 MHz, CDCl$_3$) 20.010 (CH$_3$), 22.958 (CH$_3$), 23.062 (CH$_3$), 25.051 (CH$_2$), 28.337 (CH), 29.885 (CH), 37.746 (CH$_2$), 39.629 (CH$_2$), 40.364 (CH$_2$), 61.603 (CH$_2$).

1-Iodo-3,7-dimethyl-octane (45)

To a stirring solution of 43 (5 g, 32 mmol), imidazole (2.59 g, 38 mmol, 1.2 eq) and triphenylphosphine (9.11 g, 35 mmol, 1.1 eq) in toluene (100 ml) under nitrogen was added iodine (10.44 g, 41 mmol, 1.3 eq). The reaction mixture was stirred for 18 hours then filtered. The filtrate was washed with 5% sodium thiosulfate solution (3×100 ml) then dried ($Na_2SO_4$) and concentrated in vacuo to give a white solid. This solid was taken up in hexane (20 ml), cooled and filtered. The filtrate was then concentrated in vacuo to give 45 (6 g, 71%) as a colourless oil.

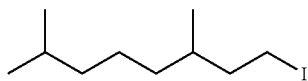

$^1$H nmr (400 MHz, $CDCl_3$) 0.86-0.90 (m, 9H) 1.10-1.32 (m, 6H) 1.49-1.69 (m, 3H) 1.84-1.90 (m, 1H) 3.14-3.28 (m, 2H). $^{13}$C nmr (100 MHz, $CDCl_3$) 5.765 ($CH_3$), 19.121 ($CH_3$), 22.970 ($CH_2$), 24.908 ($CH_2$), 28.326 (CH), 34.267 ($CH_2$), 36.858 ($CH_3$), 39.562 ($CH_2$), 41.371 ($CH_2$).

3-Benzyloxy-2-(4-benzyloxy-3,5-dimethoxy-phenyl)-7-(3,7-dimethyl-octyl)-chromen-4-one (47)

To a stirring suspension of zinc chloride (0.302 g, 2.2 mmol, 3 eq) and magnesium (0.086, 3.5 mmol, 4.7 eq) in tetrahydrofuran (2 ml) under argon was added 45 (0.879 g, 3.3 mmol, 4.4 eq) in tetrahydrofuran (2 ml). The reaction was heated to 50° C. for 20 hours then cooled. 35 (prepared as described in Example 6) (0.465 g, 0.8 mmol) in tetrahydrofuran (6 ml) and dichlorobis-[tri-(o-tolyl)-phosphinyl]palladium (0.033 g, 0.04 mmol, 0.06 eq) were added and the reaction stirred for 25 hours. The reaction was then quenched with 3 N HCl (10 ml), diluted with water and extracted into dichloromethane, washed with brine (2×), dried ($MgSO_4$) and concentrated in vacuo to give a brown oil. Column chromatography (silica gel, DCM:MeOH 1:0>19:1) yielded 47 (0.143 g, 30%) as a yellow oil.

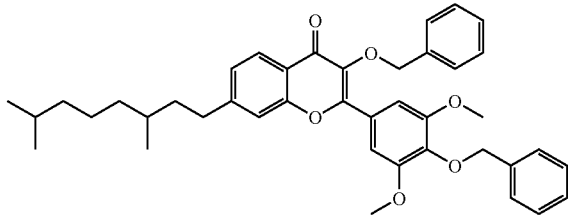

FAB+ 635.2 (27%, [M+H]$^+$) 545.2 (75%, [M−Bn]$^+$) 91.5 (100%, Bn$^+$) $C_{41}H_{47}O_6$ Calc. 635.3373 found 635.3374.

7-(3,7-Dimethyl-octyl)-3-hydroxy-2-(3,4,5-trihydroxy-phenyl)-chromen-4-one (9g*)

To a stirring solution of 47 (0.028 g, 0.05 mmol) in dichloromethane (1 ml) under argon at 0° C. was added boron tribromide (1.0M in DCM, 0.7 ml, 14 eq). The reaction was then warmed to room temperature and stirred for 23 hours. The mixture was then cooled to 0° C., methanol (1 ml) added heated to reflux for 2 hours. The reaction was then cooled and concentrated in vacuo to give a solid that was chromatographed (silica gel, DCM:methanol, 19:1) to give 9g* (0.008g, 37%) as a yellow solid.

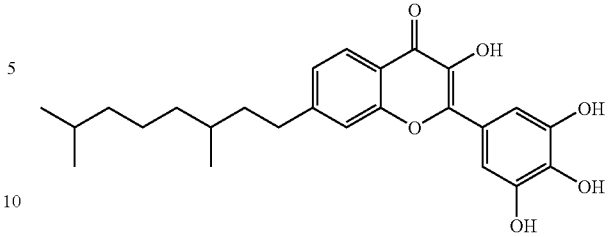

$^1$H nmr (400 MHz, $CD_3COCD_3$) 0.72-0.74 (m, 6H) 0.85-0.87 (m, 3H) 1.00-1.11 (m, 4H) 1.15-1.30 (m, 4H) 1.36-1.47 (m, 2H) 2.61-2.82 (m, 2H) 7.19 (dd, 1H, 1.1+7.0 Hz) 7.35 (s, 2H) 7.39 (s, 1H) 7.90 (d, 1H, 8.0 Hz). $^{13}$C nmr (100 MHz, $D_3CCOCD_3$) 20.26 ($CH_3$) 23.28 ($CH_3$) 23.36 ($CH_3$) 25.78 ($CH_2$) 29.03 (CH) 33.58 (CH) 34.54 ($CH_2$) 38.17 ($CH_2$) 39.52 ($CH_2$) 40.40 ($CH_2$) 108.63 (CH) 118.41 (CH) 120.19 (Q) 123.60 (Q) 125.98 (CH) 126.55 (CH) 136.38 (Q) 138.99 (Q) 146.13 (Q) 146.66 (Q) 151.20 (Q) 156.60 (Q) 173.66 (Q). EI+ 426 (100%, M$^+$) $C_{25}H_{30}O_6$ calc. 426.2042 found 426.2043. CHN $C_{25}H_{30}O_6$ calc. 70.18%; C, 7.31%; H, found 71.37%; C, 7.69%; H.

EXAMPLE 10

The branched chain flavonoid 3-hydroxy-2(3,4,5-trihydroxyphenyl)-7-(3,7,11-trimethyl-dodecyl)-chromen-4-one (compound 9i*) was prepared using similar methodology to Example 9.

Hexahydrofarnesol (44)

A flask containing a stirring suspension of farnesol (5.7 ml, 22.5 mmol) and palladium on carbon (10% Pd, 1 g, 0.04 equ) in ethanol (15 ml) was evacuated, and then filled with hydrogen. The reaction mixture was then stirred under an atmosphere of hydrogen for 36 hours. After this time the reaction was filtered and the filtrate concentrated in vacuo to give hexahydrofarnesol (44) (4.81 g, 93%) as a colourless oil.

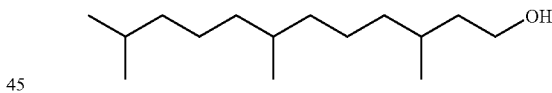

$^1$H nmr (400 MHz, $CDCl_3$) Mixture of diastereoisomers. 0.84-0.90 (m, 12H) 1.05-1.38 (m, 13H) 1.49-1.62 (m, 4H) 3.63-3.73 (m, 2H). $^{13}$C nmr (100 MHz, $CDCl_3$) 11.781 ($CH_3$), 11.799 ($CH_3$), 19.585 ($CH_3$), 19.643 ($CH_3$), 20.066 ($CH_3$), 20.125 ($CH_3$), 23.001 ($CH_3$), 23.092 ($CH_3$), 24.753 ($CH_2$), 24.880 ($CH_2$) 25.181 ($CH_2$), 58.359 ($CH_3$), 29.854 ($CH_2$), 29.950 ($CH_2$), 33.159 (CH), 33.183 (CH), 34.804 (CH) 37.329 ($CH_2$), 37.370 ($CH_2$), 37.679 ($CH_2$), 37.755 ($CH_2$) 37.794 ($CH_2$), 37.841 ($CH_2$) 39.752 ($CH_2$), 40.363 ($CH_2$), 61.654 ($CH_2$). CI+ 246.28 (50%, M+NH$_4^+$) EI+ 210 (12%, M−H$_2$O$^+$). Acc.Mass. $C_{15}H_{32}O$, (M−H$_2$O), calc. 210.2348, found 210.2346. ir (thin film) 2925, 2360, 2340, 1715, 1459.

3,7,11-Trimethyl-1-dodecyl iodide (46)

To a stirring solution of 44 (1.5 g, 6.6 mmol), imidazole (1.13 g, 16.6 mmol, 2.5 equ) and triphenylphosphine (4.40 g, 16.8 mmol, 2.5 equ) in toluene (250 ml) under nitrogen was added iodine (3.26 g, 12.8 mmol, 1.9 equ). The reaction mixture was stirred for one hour then filtered. The filtrate was washed with 8% sodium thiosulphate solution (250 ml) and brine (100 ml) then dried (Na$_2$SO$_4$) and concentrated in vacuo to give a white solid. This solid was taken up in hexane, cooled and filtered. The filtrate was then concentrated in vacuo to give 46 (1.1 g, 61%) as a colourless oil.

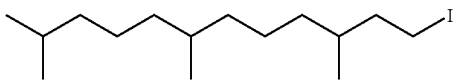

$^1$H nmr (400 MHz, CDCl$_3$) 0.84-0.87 (t, 7 Hz, 12H), 0.95-1.38 (m, 11H), 1.53 (sept, 6.6 Hz, 4H), 1.61-1.67 (m, 1H) 1.86-1.89 (m, 1H) 3.13-3.28 (m, 2H).

$^{13}$C nmr (100 MHz, CDCl$_3$) 5.733 (CH$_3$), 11.799 (CH$_2$), 11.818 (CH$_2$), 19.170 (CH$_2$), 19.602 (CH$_2$), 20.087 (CH$_2$), 20.087 (CH$_2$), 23.015 (CH), 23.111 (CH$_2$), 24.602 (CH) 25.204 (CH), 28.375 (CH$_2$). EI+ 338.1 (2%, M$^+$) 211.2 (25%, M−I$^+$). Acc.Mass. C$_{15}$H$_{31}$I, calc. 338.1471, found 338.1472. ir 2955 2360 2340.

3-Benzyloxy-2-(3,4,5-trimethoxy-phenyl)-7-(3,7,11-trimethyl-dodecyl)-chromen-4-one (48)

To a stirring suspension of zinc chloride (0.367 g, 2.7 mmol, 3 eq) and magnesium (0.100 g, 4.1 mmol, 4.7 eq) in tetrahydrofuran (2.5 ml) under argon was added 7 (1.268 g, 3.8 mmol, 4.2 eq) in tetrahydrofuran (2.5 ml). The reaction was heated to 50° C. for 19 hours then cooled. 34 (0.481 g, 0.8 mmol) in tetrahydrofuran (7 ml) and dichlorobis-[tri-(o-tolyl)-phosphinyl]palladium (0.063 g, 0.08 mmol, 0.09 eq) added and the reaction stirred for 25 hours. The reaction was then quenched with 3 N HCl (10 ml), diluted with water and extracted into ethyl acetate (3×). The combined aqueous layers were dried (MgSO$_4$) and concentrated in vacuo to give a purple oil. Column chromatography (silica gel, petrol:EtOAc 9:1>2:1) yielded 48 (0.082 g, 15%) as a pale yellow oil.

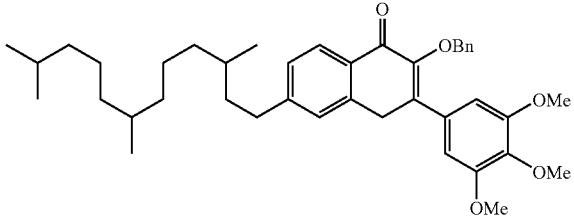

$^1$H nmr (400 MHz, CDCl$_3$) 0.84-0.92 (m, 7H), 0.96 (d, 6 Hz, 2H), 1.05-1.42 (m, 8H), 1.48-1.70 (m, 12H) 2.68-2.83 (m, 2H) 3.78 (s, 6H) 3.93 (s, 3H) 5.13 (s, 2H) 7.21-7.37 (m, 9H) 8.19 (d, 8Hz, 1H). $^{13}$C nmr (100 MHz, CDCl$_3$) 19.559 (CH$_3$), 19.625 (CH$_3$), 19.684 (CH$_3$), 19.750 (CH$_3$), 22.629 (CH$_3$), 22.721 (CH$_3$), 24.382 (CH$_2$), 24.799 (CH$_2$), 27.983 (CH), 32.603, (CH) 32.783 (CH), 33.743 (CH$_2$) 37.218 (CH$_2$), 37.281 (CH$_2$), 37.372 (CH$_2$), 38.454 (CH$_3$), 38.552 (CH$_2$), 39.363 (CH$_2$), 56.153 (CH$_3$), 60.990 (CH$_3$), 74.507 (CH$_2$), 106.391 (CH$_3$) 116.941 (CH$_3$), 122.079 (Q), 125.654 (CH), 126.202 (Q) 128.182 (CH), 128.270 (CH) 128.880 (CH), 136.843 (Q) 139.921 (Q), 150.178 (Q), 152.857 (Q), 155.406 (Q), 175.015 (Q). EI+ 628.0 (21%, M$^+$) 537.1 (27%, M−Bn$^+$). Acc.Mass. C$_{40}$H$_{52}$O$_6$, calc. 628.3764, found 628.3768. ir (Thin film) 2928, 2360, 2252, 1828, 1457, 908, 734.

3-Hydroxy-2-(3,4,5-trihydroxy-phenyl)-7-(3,7,11-trimethyl-dodecyl)-chromen-4-one (9i*)

To a stirring solution of 48 (0.048 g, 0.08 mmol) in dichloromethane (2.5 ml) under argon at 0° C. was added boron tribromide (1.0M in DCM, 2.5 ml, 26 eq). The reaction was then warmed to room temperature and stirred for 19 hours. The mixture was then cooled to 0° C., methanol (2 ml) added heated to reflux for 2 hours. The reaction was then cooled and concentrated in vacuo to give a solid that was chromatographed (silica gel, chloroform:methanol, 9:1) to give 9i* (0.033g, 87%) as a waxy solid.

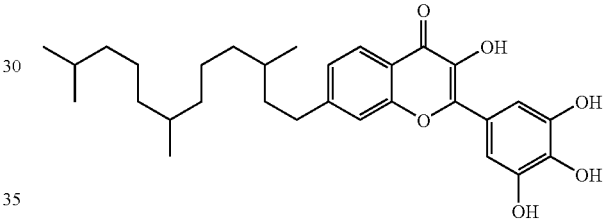

$^1$H nmr (400 MHz, CD$_3$COCD$_3$) 7.91 (d, 1H, 8 Hz) 7.36 (d, 1H, 8 Hz) 7.18 (d, 1H, 8 Hz) 6.91-6.98 (m, 1H) 2.52-2.75 (m, 2H) 1.61-0.67 (m, 29H). $^{13}$C nmr (100 MHz, CD$_3$COCD$_3$) 14.940 (CH$_3$) 20.292 (CH$_3$) 20.358 (CH$_3$) 23.325 (CH$_3$) 23.413 (CH$_3$) 25.431 (CH$_2$) 25.890 (CH$_2$) 29.046 (CH$_2$) 29.731 (CH$_2$) 29.923 (CH$_2$) 30.116 (CH$_2$) 30.309 (CH$_2$) 30.502 (CH) 30.694 (CH) 30.887 (CH) 31.060 (CH$_2$) 33.557 (CH) 33.863 (CH) 34.582 (CH$_2$) 38.395 (CH$_2$) 38.453 (CH$_2$) 38.472 (CH$_2$) 40.472 (CH$_2$) 60.979 (CH$_2$) 108.737 (CH) 118.395 (CH) 120.129 (Q) 123.543 (Q) 126.017 (CH) 126.636 (CH) 128.927 (CH) 129.468 (CH) 146.672 (CH) 151.261 (CH) 156.579 (CH) 172.040 (Q). EI+496.2 (100%, M$^+$) 313.1 (60%, [M−C$_{13}$H$_{27}$]$^+$). C$_{30}$H$_{40}$O$_6$ calc. 496.2825, obs. 496.2823.

The following scheme summarises the production of branched chain compounds in Examples 9 and 10.

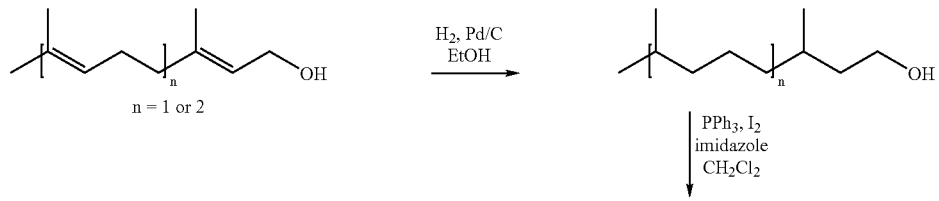

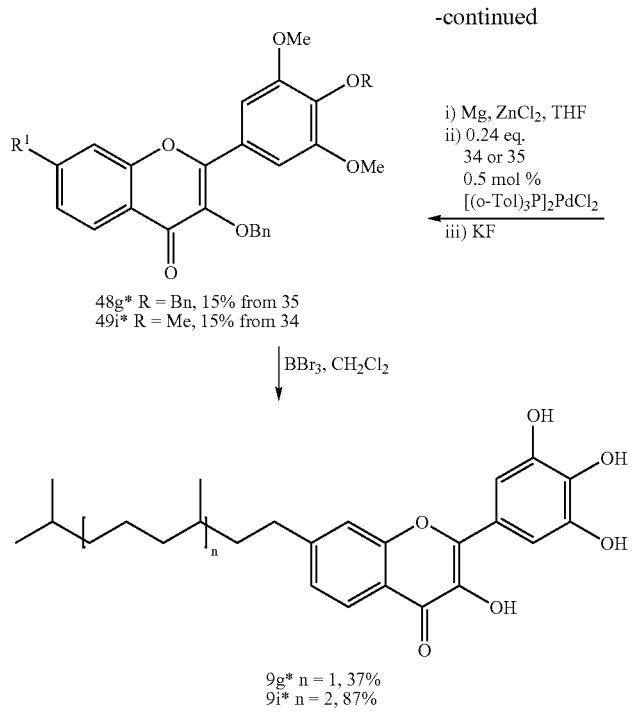
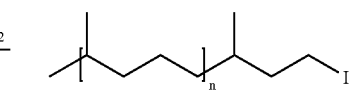

48g* R = Bn, 15% from 35
49i* R = Me, 15% from 34

9g* n = 1, 37%
9i* n = 2, 87%

EXAMPLE 11

6-decyl-flavonoid (compound 11g) was prepared by the following synthetic route:

N-(4-Methoxy-phenyl)-acetamide (51)

To a stirring suspension of p-anisidine (6.036 g, 49 mmol) in dichloromethane (20 ml) was added acetic anhydride (5 ml, 53 mmol, 1.1 equ) over one hour. The reaction was stirred for a further hour then poured onto hexane (60 ml) and stirred for another hour. The solid was collected and washed with hexane to give N-(4-methoxy-phenyl)-acetamide 51 (7.717 g, 95%) as a pale grey solid.

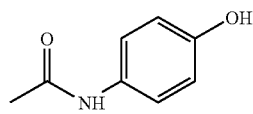

$^1$H nmr (400 MHz, CDCl$_3$) 2.13 (s, 3H) 3.78 (s, 3H) 6.83 (d, 2H, 9 Hz) 7.38 (d, 2H, 9 Hz). $^{13}$C nMr (100 MHz, CDCl$_3$) 24.66 (CH$_3$) 55.85 (CH$_3$) 114.49 (CH) 122.37 (CH) 131.41 (Q) 156.82 (Q) 168.79 (Q). EI+ 165.1 (71%, M$^+$) 123.1 (70%, [M−Ac]$^+$) 108.1 (100%, [NH$_2$PhO]$^+$) C$_9$H$_{11}$NO$_2$ Calc. 165.0790 Found 165.0789.

N-(3-Acetyl-4-hydroxy-phenyl)-acetamide

To a stirring suspension of N-(4-methoxy-phenyl)-acetamide (5.253 g, 32 mmol) and acetyl chloride (6.6 ml, 93 mmol, 2.9 equ) in dichloromethane (55 ml) was added aluminium trichloride (14.55 g, 109 mmol, 3.4 equ) in portions over 90 minutes. The reaction was then heated to reflux for 4.5 hours and cooled overnight. The mixture was poured onto ice then extracted into dichloromethane (5×), dried (MgSO$_4$) and concentrated in vacuo to give N-(3-acetyl-4-hydroxy-phenyl)-acetamide (5.336 g, 87%) as a pale green solid.

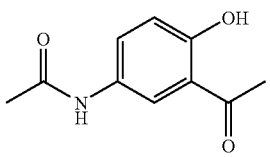

$^1$H nmr (400 MHz, CDCl$_3$) 2.19 (s, 3H) 2.63 (s, 3H) 6.94 (d, 1H, 9 Hz) 7.12 (brs, 1H, NH) 7.33 (dd, 1H, 2.6+9 Hz) 8.17 (d, 1H, 2.6 Hz) 12.12 (s, 1H). $^{13}$C nmr (100 MHz, CDCl$_3$) 24.71 (CH$_3$) 27.16 (CH$_3$) 119.08 (CH) 119.60 (Q) 122.94 (CH) 129.58 (CH) 159.62 (Q) 168.86 (Q) 204.84 (Q). EI+193.1 (100%, M$^+$) 151.1 (91%, [M−Ac]$^+$) C$_{10}$H$_{11}$NO$_3$ Calc. 193.0739 Found 193.0740.

1-(5-Amino-2-hydroxy-phenyl)-ethanone

A suspension of N-(3-acetyl-4-hydroxy-phenyl)-acetamide (1.029 g, 5.3 mmol) in 15% HCl (1.5 ml, 6.2 mmol, 1.2 equ) was heated to reflux for 40 minutes, then cooled and neutralised with 10% aqueous ammonia. The precipitated solid was collected by filtration as 1-(5-amino-2-hydroxy-phenyl)-ethanone (0.677 g, 84%) a green solid.

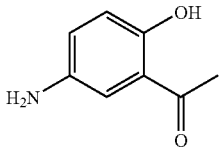

$^1$H nmr (400 MHz, CDCl$_3$) 2.58 (s, 3H) 3.47 (brs, 2H) 6.83 (d, 1H, 8.8 Hz) 6.91 (dd, 1H, 2.8+8.8 Hz) 7.02 (d, 1H, 2.8 Hz). $^{13}$C nmr (100 MHz, CDCl$_3$) 27.12 (CH$_3$) 115.71 (CH) 119.40

(CH) 119.87 (Q) 125.737 (CH) 138.40 (Q) 156.03 (Q) 204.48 (Q). EI+ 151.1 (100%, M+) C$_8$H$_9$NO$_2$ Calc. 151.0633 Found 151.0632.

1-(5-Iodo-2-hydroxy-phenyl)-ethanone (52)

To a stirring solution of 1-(5-amino-2-hydroxy-phenyl)-ethanone (6.856 g, 46 mmol) in 98% sulfuric acid (24 ml) and water (19 ml) was added sodium nitrite (3.30 g, 48 mmol, 1.05 equ) in water (5.5 ml). The reaction was stirred for 35 minutes, then sulfuric acid (4 ml), copper powder (0.17 g, 0.3 mmol, 0.06 equ) and potassium iodide (8.80 g, 53 mmol, 1.16 equ) in water (5.5 ml) added. The mixture was then heated slowly to 65° C. and maintained at 65° C. for 2 hours. The reaction was then cooled, water (25 ml) and sodium hydrogen carbonate added. More water was added, then extracted into a mixture of ethyl acetate and dichloromethane, then ethyl acetate (2×). The combined organic layers were washed with brine then concentrated in vacuo. This mixture was then taken up in ethyl acetate and 2 M HCl, filtered and the organic layer dried (MgSO$_4$) and concentrated in vacuo to give 1-(5-iodo-2-hydroxy-phenyl)-ethanone 52 (1.339 g, 39%) as a purple oil. This was then used in the next reaction.

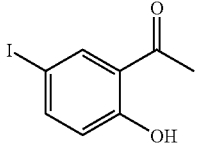

1-(2-Hydroxy-5-iodo-phenyl)-3-(4-benzyloxy-3,5-7 dimethoxy-phenyl)-propenone (54)

To a stirring solution of 1-(5-iodo-2-hydroxy-phenyl)-ethanone 52 (4.243 g, 16 mmal) and 4-benzyloxy-3,5-dimethoxy benzaldehyde (4.51 g, 17 mmol, 1.02 equ) in ethanol (100 ml) was added potassium hydroxide (1.839 g, 33 mmol, 2.03 equ). The reaction mixture was stirred for 191 hours then acidified with 6 M HCl and diluted with water and brine. The mixture was extracted into ethyl acetate (3×). The combined organic layers were then washed with brine, dried (MgSO$_4$) and concentrated in vacuo to give a black oil. This was taken up in ethanol (50 ml), potassium hydroxide (1.97 g) added and stirred for 169 hours. The reaction was then acidified with 6 M HCl and diluted with water then extracted into ethyl acetate (3×) washed with brine, dried (MgSO$_4$) and concentrated in vacuo to give a black foam. Recrystallisation (ethanol) yielded 1-(2-hydroxy-5-iodo-phenyl)-3-(4-benzyloxy-3,5-dimethoxy-phenyl)-propenone 54 (4.122 g, 49%).

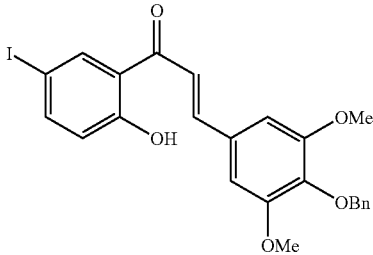

EI+ 516 (31%, M+) 425 (32%, [M−Bn]+) 91 (100%, Bn+) C$_{24}$H$_{21}$IO$_5$ Calc. 516.0434 Found 516.0435.

3-Hydroxy-6-iodo-2-(4-benzyloxy-3,5-dimethoxy-phenyl)-chromen-4-one (56)

To a stirring solution of 1-(2-hydroxy-5-iodo-phenyl)-3-(4-benzyloxy-3,5-dimethoxy-phenyl)-propenone 54 (4.155 g, 8 mmol) in methanol (80 ml) and 16% aqueous sodium hydroxide solution (10 ml, 40 mmol, 5 equ) at 0° C. was added 15% aqueous hydrogen peroxide (10 ml, 44 mmol, 5.5 equ) dropwise. The solution was stirred at 0° C. for ten minutes then sealed and placed in a refrigerator for 16 hours. The reaction was then acidified (6 M HCl), diluted with water and extracted into dichloromethane (3×). The organic layer was then washed with sodium hydrogen carbonate solution and brine, dried (MgSO$_4$) and concentrated to give a brown solid. Recrystallisation (ethanol) yielded 3-hydroxy-6-iodo-2-(4-benzyloxy-3,5-dimethoxy-phenyl)-chromen-4-one 56 (2.106 g, 49%) as a grey solid.

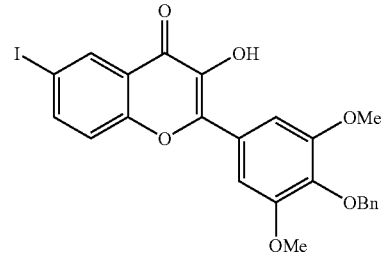

$^1$H nmr (400 MHz, CDCl$_3$) 3.93 (s, 6H) 5.12 (s, 2H) 7.00 (brs, 1H) 7.25-7.38 (m, 5H) 7.49-7.51 (m, 3H) 7.95 (dd, 1H, 2.2+8.9 Hz) 8.58 (s, 1H). $^{13}$C nmr (100 MHz, CDCl$_3$) 56.73 (CH$_3$) 75.71 (CH$_2$) 105.92 (CH) 120.94 (Q) 123.00 (Q) 128.39 (CH) 128.65 (CH) 128.86 (CH) 134.89 (Q) 138.10 (Q) 142.43 (Q) 154.10 (Q) 155.02 (Q). EI+ 530.4 (31%, M+) 439.3 (91%, [M−Bn]+) 91.1 (100%, Bn+) C$_{24}$H$_{19}$IO$_6$ Calc. 530.0226 Found 530.0226.

3-Hydroxy-6-decyl-2-(4-benzyloxy-3,5-dimethoxy-phenyl)-chromen-4-one (58)

To a stirring solution of 1-decene (0.189 g, 1.3 mmol, 1.4 eq) in tetrahydrofuran (2 ml) under argon was added 9-BBN in tetrahydrofuran (0.5M, 2.8 ml, 1.4 mmol, 1.5 eq). The reaction was stirred for 8 hours then 3-hydroxy-6-iodo-2-(4-benzyloxy-3,5-dimethoxy-phenyl)-chromen-4-one 56 (0.501 g, 0.9 mmol) in tetrahydrofuran (5 ml), 3M NaOH solution (1.26 ml) and dichloropalladium(dppf) (0.021 g, 0.03 mmol, 0.03 eq) were added and the reaction heated to reflux for 15 hours. The reaction was then quenched with water and diethyl ether and acidified (6 M HCl). The organic layer was collected and the aqueous layer extracted with diethyl ether (2×). The combined organic layers were washed with brine, dried (MgSO$_4$) and concentrated in vacuo to give a red oil. This was passed through a short plug of silica, eluting with ethyl acetate to give 3-hydroxy-6-decyl-2-(4-benzyloxy-3,5-dimethoxy-phenyl)-chromen-4-one 58 (0.369 g, 72%) as a red oil.

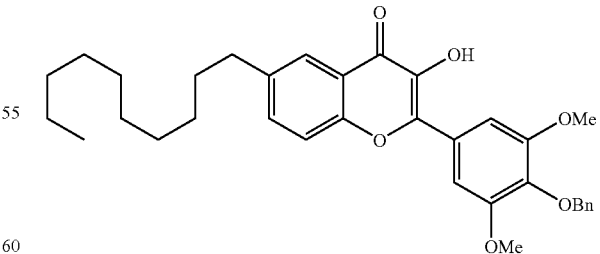

6-Decyl-3-hydroxy-2-(3,4,5-trihydroxy-phenyl)-chromen-4-one (11g)

To a stirring solution of 3-hydroxy-6-decyl-2-(4-benzyloxy-3,5-dimethoxy-phenyl)-chromen-4-one (0.369 g, 0.7 mmol) in dichloromethane (20 ml) under Ar at 0° C. was added boron tribromide in dichloromethane (1.0M, 3.4 ml, 3.4 mmol, 5 equ). The mixture was warmed to room temperature and then stirred for 15 hours. Methanol (10 ml) was then added. The reaction was heated to reflux for 1 hour, then concentrated in vacuo to give a brown solid. Water (25 ml) was added and then extracted into ethyl acetate (3×). The organic layer was washed with brine then dried (MgSO$_4$) and concentrated in vacuo to give 11g (0.318 g, 110%) as a brown oil.

The substituted flavonol 9d was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried (MgSO$_4$) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol no. 11g as a fine yellow precipitate that was collected by filtration or extraction into ethyl acetate.

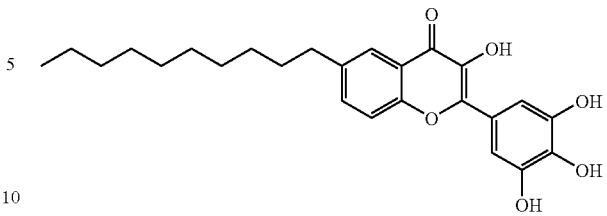

$^1$H nmr (400 MHz, CD$_3$SOCD$_3$) 1.25 (t, 3H, 6.4 Hz) 1.62-1.72 (m, 14H) 1.99-2.04 (m, 2H) 3.13 (t, 2H, 7.5 Hz) 7.72 (s, 2H) 7.98-8.04 (m, 2H) 8.28 (s, 1H) 9.21 (s, 1H) 9.61 (s, 3H). $^{13}$C nmr (100 MHz, D$_3$CSOCD$_3$) 14.28 (CH$_3$) 22.43 (CH$_2$) 28.86 (CH$_2$) 29.01 (CH$_2$) 29.15 (CH$_2$) 29.15 (CH$_2$) 29.30 (CH$_2$) 31.20 (CH$_2$) 31.62 (CH$_2$) 34.75 (CH$_2$) 107.59 (CH) 118.27 (CH) 121.31 (Q) 121.54 (Q) 123.50 (CH) 134.30 (CH) 136.04 (Q) 138.30 (Q) 138.97 (Q) 146.06 (Q) 146.34 (Q) 153.14 (Q) 172.69 (Q). FAB+ 427.4 (100%, [M+H]$^+$) C$_{25}$H$_{31}$O$_6$ calc. 427.2122 found 427.2123.

The reaction is summarised in the following scheme:

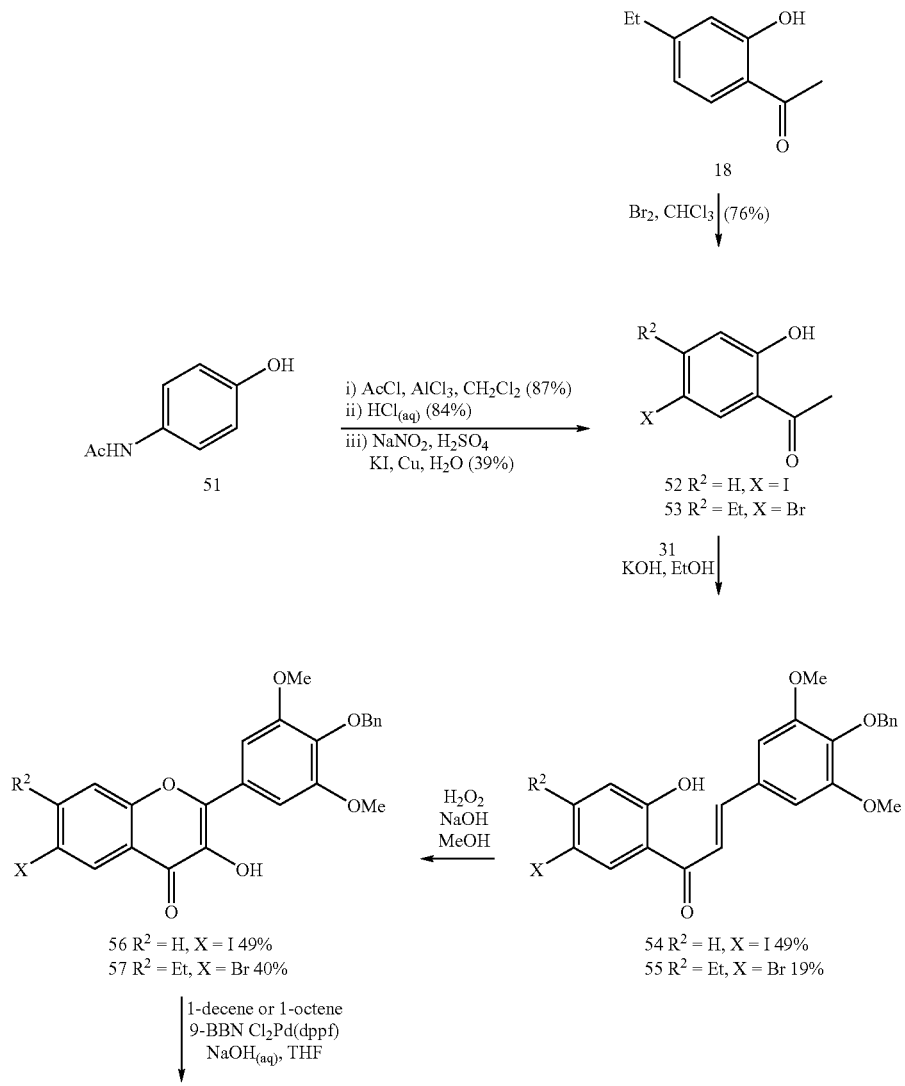

-continued

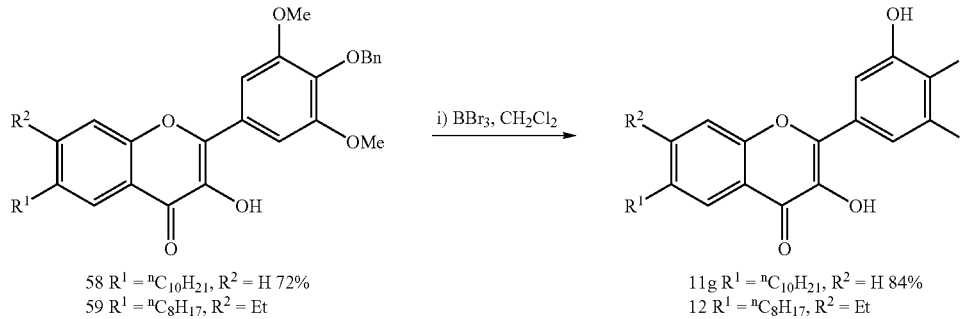

58 R¹ = ⁿC₁₀H₂₁, R² = H 72%
59 R¹ = ⁿC₈H₁₇, R² = Et

11g R¹ = ⁿC₁₀H₂₁, R² = H 84%
12 R¹ = ⁿC₈H₁₇, R² = Et
100% over next two steps

EXAMPLE 12

A dual chain flavonoid was prepared as described below:

1-(5-Bromo-4-ethyl-2-hydroxy-phenyl)-ethanone (53)

To a stirring solution of 18 (prepared as described in Example 1) (1.002 g, 6.1 mmol) in chloroform (10 ml) under argon at −12° C. was added bromine (0.32 ml, 6.2 mmol, 1.02 equ) in chloroform (5 ml) over 20 minutes. The reaction was stirred at −12° C. for 50 minutes, then poured into water (20 ml). The organic layer was washed with water (10 ml), 10% sodium thiosulfate (2×10 ml), and water (10 ml), dried (MgSO₄) then concentrated in vacuo to give 1-(5-bromo-4-ethyl-2-hydroxy-phenyl)-ethanone 53 (1.132 g, 76%) as a brown solid.

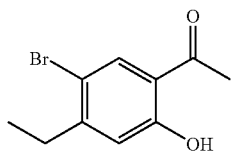

¹H nmr (400 MHz, CDCl₃). ¹³C nmr (100 MHz, CDCl₃) EI+ 242(+244) (16%, M⁺) 227(+229) (40%, [M−Me]⁺) C₁₀H₁₁BrO₂ calc. 241.9942+243.9923 found 241.9941+243.9916.

1-(5-Bromo-4-ethyl-2-hydroxy-phenyl)-3-(4-benzyloxy-3,5-dimethoxy-phenyl)-propenone (55)

To a stirring solution of 1-(5-bromo-4-ethyl-2-hydroxy-phenyl)-ethanone 53 (1.132 g, 4.7 mmol) and 4-benzyloxy-3,5-dimethoxy benzaldehyde 31 (0.918 g, 4.7 mmol, 1.0 equ) in ethanol (30 ml) was added potassium hydroxide (0.545 g, 9.7 mmol, 2.1 equ). The reaction mixture was stirred for 26 hours then acidified with 10% HCl and diluted with water. The mixture was extracted into ethyl acetate (4×). The combined organic layers were then washed with brine, 10% sodium bisulfite solution, saturated aqueous sodium bicarbonate and brine again. The organic layer was then dried (MgSO₄) and concentrated in vacuo to give a brown oil. Recrystallisation (ethanol) yielded 1-(5-bromo-4-ethyl-2-hydroxy-phenyl)-3-(4-benzyloxy-3,5-dimethoxy-phenyl)-propenone 55 (0.368 g, 19%).

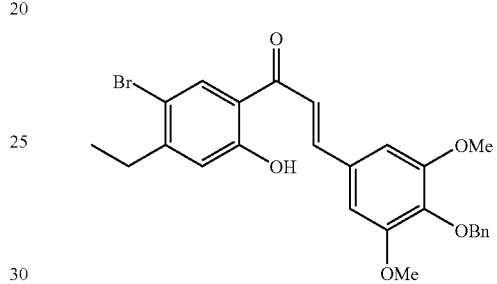

¹H nmr (400 MHz, CDCl₃) 1.26 (t, 3H, 7.5 Hz) 2.76 (q, 2H, 7.5 Hz) 3.92 (s, 6H) 5.10 (s, 2H) 6.88 (s, 2H) 6.94 (s, 1H) 7.28-7.42 (m, 3H) 7.48 (dd, 1H, 1.4+6.7 Hz) 7.85 (d, 1H, 15 Hz) 8.03 (s, 1H) 12.78 (s, 1H). ¹³C nmr (100 MHz, CDCl₃) 13.89 (CH₃), 30.25 (CH₂), 56.74 (CH₃) 75.53 (CH₂) 106.61 (CH) 113.24 (Q) 119.01 (CH) 119.54 (CH) 119.89 (Q) 128.41 (CH) 128.61 (CH) 128.86 (CH) 130.38 (Q) 133.16 (CH) 137.81 (Q) 140.31 (Q) 146.77 (CH) 152.75 (Q) 154.25 (Q) 163.24 (Q) 192.47 (Q). EI+ 496(+498) (18%, M⁺) 405(+407) (35%, [M−Bn]⁺) 91.1 (100%, Bn⁺) C₂₆H₂₅BrO₅ calc. 496.0855+498.0869 found 496.0884+498.0863.

6-Bromo-7-ethyl-3-hydroxy-2-(4-benzyloxy-3,5-dimethoxy-phenyl)-chromen-4-one (57)

To a stirring solution of 1-(S-bromo-4-ethyl-2-hydroxy-phenyl)-3-(4-benzyloxy-3,5-dimethoxy-phenyl)-propenone 55 (0.238 g, 0.5 mmol) in methanol (10 ml) and 16% aqueous sodium hydroxide solution (0.6 ml, 2.4 mmol, 5 equ) at 0° C. was added 15% aqueous hydrogen peroxide (0.6 ml, 2.6 mmol, 5.5 equ) dropwise. The solution was stirred at 0° C. for ten minutes then sealed and placed in a refrigerator for 115 hours. The reaction was then acidified (2 M HCl) and extracted into dichloromethane (2×). The organic layer was then washed with brine, dried (MgSO₄) and concentrated to give a yellow foam. Recrystallisation (ethanol) yielded 6-bromo-7-ethyl-3-hydroxy-2-(4-benzyloxy-3,5-dimethoxy-phenyl)-chromen-4-one 57 (0.097 g, 40%) as a yellow solid.

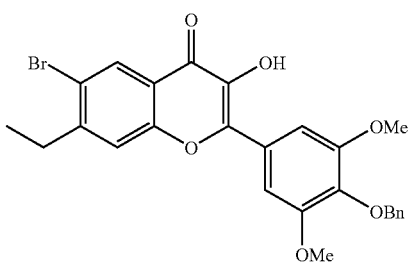

¹H nmr (400 MHz, CDCl₃) 1.34 (t, 3H, 7.5 Hz) 2.90 (q, 2H, 7.5 Hz) 3.94 (s, 6H) 5.12 (s, 2H) 6.99 (s, 1H) 6.99 (s, 1H) 7.25-7.38 (m, 4H) 7.46-7.52 (m, 4H) 8.40 (s, 1H) ¹³C nmr (100 MHz, CDCl₃) 14.03 (CH₃), 30.23 (CH₂), 56.70 (CH₃) 75.47 (CH₂) 105.82 (CH) 118.60 (CH) 120.19 (Q) 120.92 (Q) 126.50 (Q) 128.36 (CH) 128.60 (CH) 129.08 (CH) 137.95 (Q) 138.52 (Q) 139.35 (Q) 145.20 (Q) 150.03 (Q) 153.88 (Q) 154.66 (Q) 172.32 (Q).

7-Ethyl-3-hydroxy-6-octyl-2-(4-benzyloxy-3,5-dimethoxy-phenyl)-chromen-4-one (59)

To a stirring solution of 1-octene (0.032 g, 0.3 mmol, 1.4 eq) in tetrahydrofuran (1 ml) under argon at 0° C. was added 9-BBN in tetrahydrofuran (0.5M, 0.6 ml, 0.3 mmol, 1.5 eq). The reaction was stirred for 7 hours then 6-bromo-7-ethyl-3-hydroxy-2-(4-benzyloxy-3,5-dimethoxy-phenyl)-chromen-4-one 57 (0.102 g, 0.2 mmol) in tetrahydrofuran (4 ml), 3M NaOH solution (0.2 ml) and dichloropalladium(dppf) (0.005 g, 0.006 mmol, 0.03 eq) were added and the reaction heated to reflux for 15 hours. The reaction was then quenched with water and diethyl ether and acidified (6 M HCl). The organic layer was collected and the aqueous layer extracted with dichloromethane. The combined organic layers were washed with brine, dried (MgSO₄) and concentrated in vacuo to give a red oil.

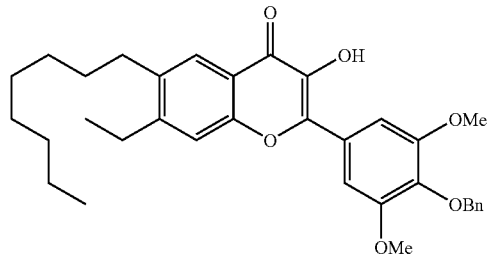

7-Ethyl-3-hydroxy-6-octyl-2-(3,4,5-trihydroxy-phenyl)-chromen-4-one (12)

To a stirring solution of 7-ethyl-3-hydroxy-6-octyl-2-(4-benzyloxy-3,5-dimethoxy-phenyl)-chromen-4-one 59 (0.125 g, 0.2 mmol) in dichloromethane (10 ml) under Ar at 0° C. was added boron tribromide in dichloromethane (1.0M, 1.2 ml, 1.2 mmol, 5.2 equ). The mixture was warmed to room temperature and then stirred for 21 hours. Methanol (5 ml) was then added. The reaction was heated to reflux for 2 hours, then concentrated in vacuo to give a brown solid. Water (10 ml) was added then extracted into ethyl acetate (3×). The organic layer was washed with brine then dried (MgSO₄) and concentrated in vacuo to give 12 (0.088 g, 100% over 2 steps) as a green solid.

The substituted flavonol 12 was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried (MgSO₄) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 12 as a fine yellow precipitate that was collected by filtration or extraction into ethyl acetate.

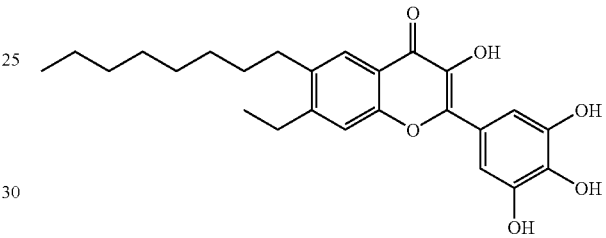

¹H nmr (400 MHz, CD₃SOCD₃) 0.91 (m, 3H) 1.29-1.40 (m, 13H) 1.61-1.65 (m, 2H) 2.75-2.88 (m, 4H) 7.35 (s, 2H) 7.49 (s, 1H) 7.86 (s, 1H) 8.81 (s, 1H) 9.16-9.30 (m, 3H). ¹³C nmr (100 MHz, D₃CSOCD₃) 14.30 (CH₃) 14.70 (CH₃) 22.43 (CH₂) 25.33 (CH₂) 29.00 (CH₂) 29.18 (CH₂) 29.34 (CH₂) 30.71 (CH₂) 31.62 (CH₂) 31.69 (CH₂) 108.53 (CH) 116.80 (CH) 119.40 (Q) 121.66 (Q) 123.96 (CH) 135.91 (Q) 137.42 (Q) 138.14 (Q) 146.06 (Q) 146.06 (Q) 148.83 (Q) 153.38 (Q) 172.52 (Q). FAB+ 447.4 (100%, ([M+H]⁺) C₂₅H₃₁O₆ calc. 427.2121 found 427.2125.

The reaction can be summarised in the following scheme:

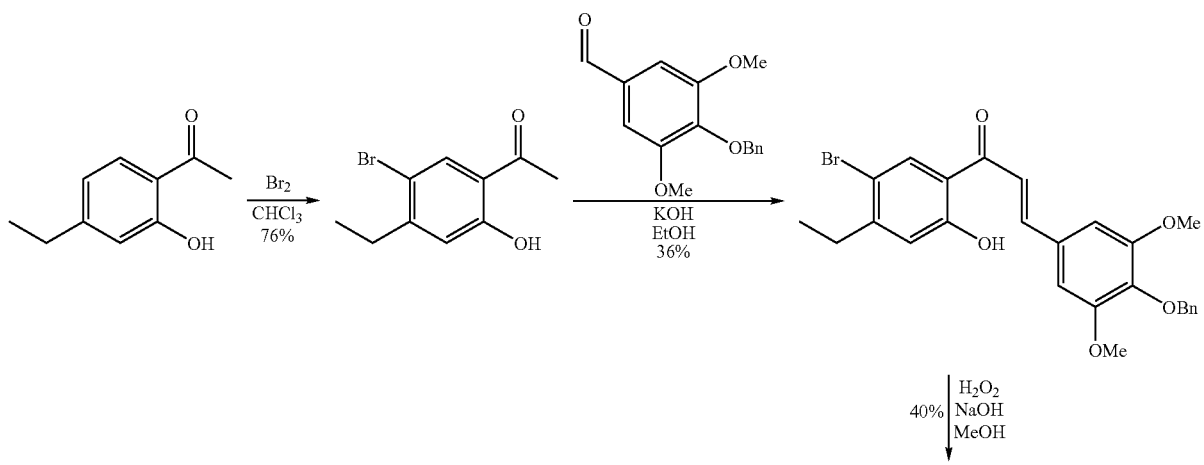

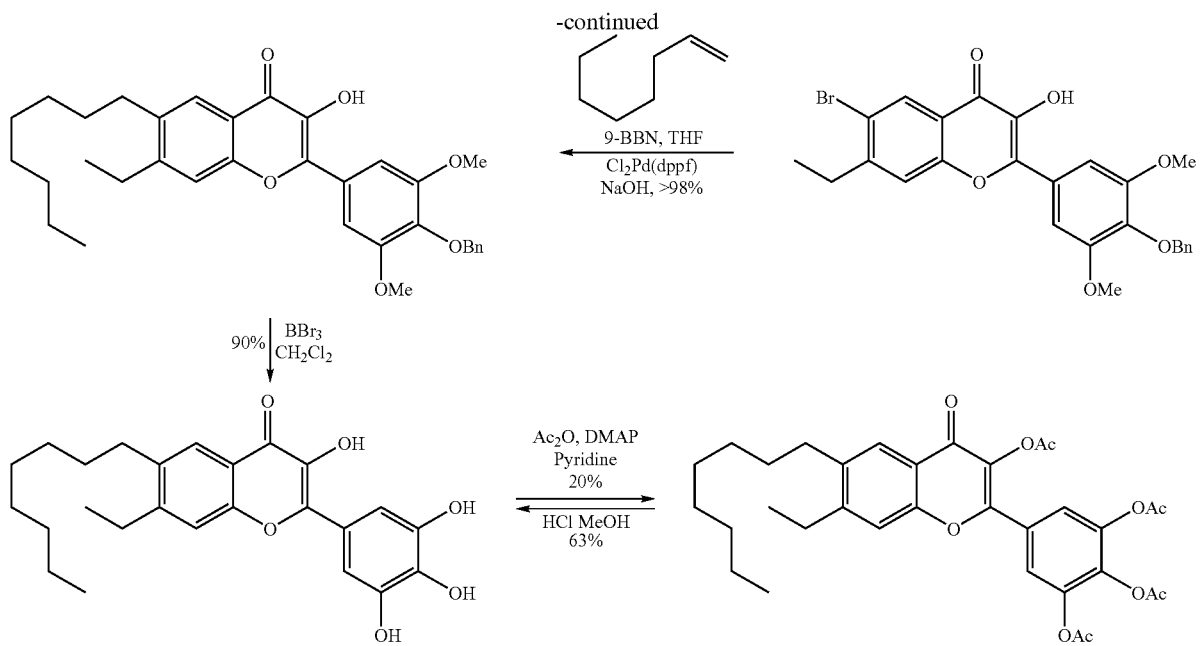
An alternative scheme was employed to produce 7-alkyl-flavonols. Briefly, the alkyl chain was introduced by Suzuki cross-coupling prior to the construction of the flavonoid by Baker-Venkataraman rearrangement.
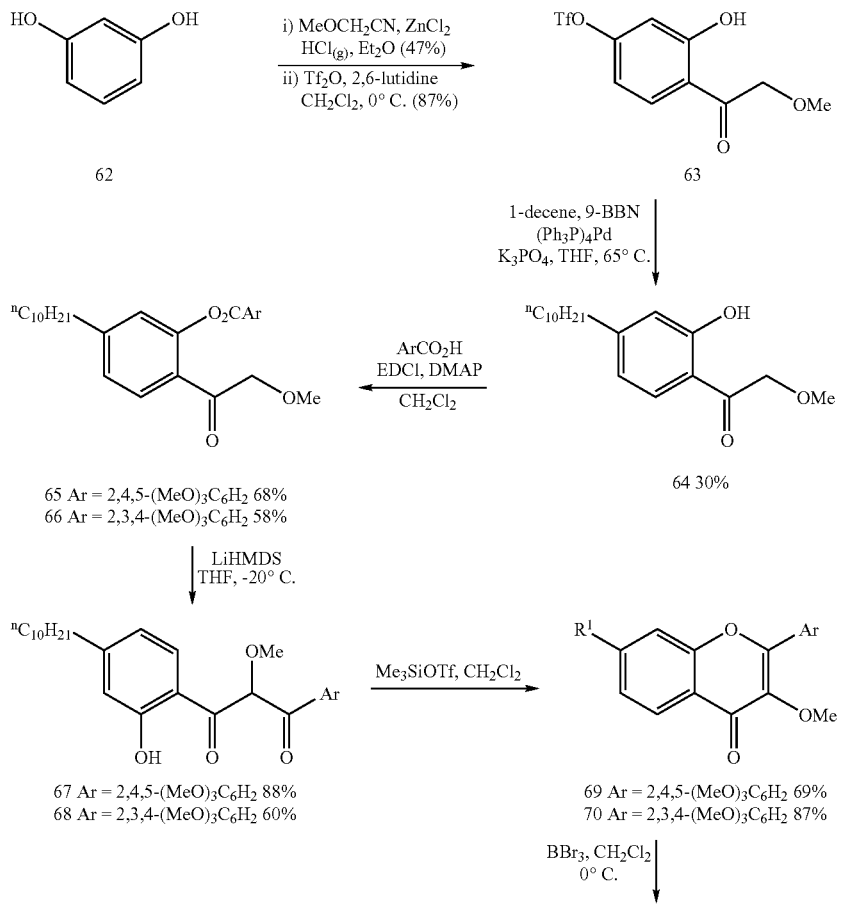

-continued

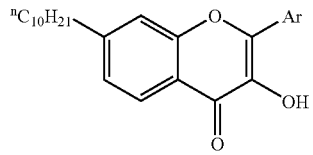

13g Ar = 2,4,5-(HO)$_3$C$_6$H$_2$ 98%
15g Ar = 2,3,4-(HO)$_3$C$_6$H$_2$ 98%

EXAMPLE 13

1-(2',4'-dihydroxy)-phenyl-2-methoxy ethanone

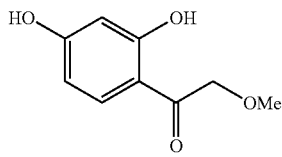

Resorcinol 62 (1.78 g, 16.14 mmol, 1.2 eq), methoxyacetonitrile (1.00 ml, 13.44 mmol) and zinc chloride (366 mg, 2.69 mmol, 0.2 eq) were placed in a three necked round bottomed flask and dissolved in dry diethyl ether (10 ml) under argon. The solution was cooled to 0° C. and the argon inlet replaced with a calcium chloride drying tube. Dry hydrochloric acid was bubbled through the solution for 2 hours. The resulting precipitate was filtered off and washed with ether (10 ml). The hydrochloride salt was dissolved in water (10 ml) and heated under reflux for 30 minites After cooling the resulting solid was filtered off and washed with water (10 ml.) and dried under vacuum to give the acetophenone (1.16 g, 47%). m.p. 108-110° C.

$\delta_H$ (400 MHz: D-6 DMSO): 3.35 (3H, s, OCH$_3$), 4.66 (2H, s, OCH$_2$), 6.29 (1H, d, J 2.3 Hz, H-3'), 6.36 (1H, dd, J 2.3 Hz and 8.8 Hz, H-5'), 7.68 (1H, d, J 8.8 Hz, H-6'), 10.59 (1H, s, OH), 11.92 (1H, s, OH). $\delta_C$ (100 MHz: D-6 DMSO): 58.89 (CH$_3$), 74.68 (CH$_2$), 102.80 (CH), 108.55 (CH), 111.99 (C), 132.26 (CH), 163.77 (C), 164.95 (C), 199.52 (C). m/z (EI): 182.1 (M$^+$, 10%), 137.0 (100). Found: 182.0581 C$_9$H$_{10}$O$_4$ requires (M$^+$) 182.0579. Found: C, 59.43%; H, 5.50%. C$_9$H$_{10}$O$_4$ requires C, 59.34%; H 5.53%. $\upsilon_{max}$ (golden gate)/cm$^{-1}$: 3361 (OH), 1633 (C=O). R$_f$ silica EtOAc 0.56

1-(2'-hydroxy-4'-trifluoromethanesulfonyloxy)-phenyl-2-methoxy ethanone (63)

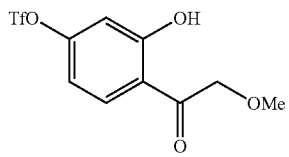

Trifluoromethanesulfonic anhydride (2.55 ml, 15.54 mmol, 1.0 eq) was added slowly to a solution of 1-(2',4'-dihydroxy)-phenyl-2-methoxy ethanone (2.83 g, 15.54 mmol) and 2,6-lutidine (1.81 ml, 15.54 mmol, 1.05 eq) in dry dichloromethane (50 ml) cooled to 0° C. and under an atmosphere of argon. After 1 hour the solution was diluted with dichloromethane (100 ml) and washed with 1 M hydrochloric acid (100 ml). The organic layer was re-extracted with dichloromethane (50 ml) and the combined organics washed with 1 M hydrochloric acid (100 ml). The organics were then dried over magnesium sulfate and concentrated under vacuum to give the triflate as a purple oil suitably pure for the next step (4.31 g, 87%). The product was contaminated with some ditriflate.

$\delta_H$ (400 MHz: CDCl$_3$): 3.53 (3H, s, OCH$_3$), 4.68 (2H, s, CH$_2$), 6.84 (1H, dd, J 2.5 and 8.9 Hz, H-5), 6.94 (1H, d, J 2.5 Hz, H-3), 7.85 (1H, d, J 8.9 Hz, H-6), 12.14 (1H, s, OH).

1-(2'-hydroxy-4'-decyl)-phenyl-2-methoxy ethanone (64)

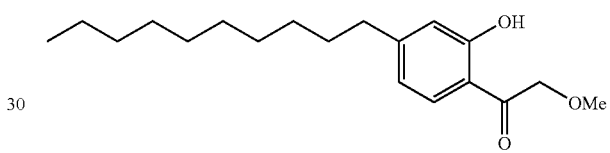

9-BBN (0.5 M solution in THF, 152.6 ml, 76.29 mmol, 1.05 eq) was added to decene (14.44 ml, 76.29 mmol, 1.05 eq) at room teperature under argon. The solution was then stirred at room temperature for 6 h. After this time K$_3$PO$_4$ (23.19 g, 108.99 mmol, 1.5 eq), Pd(Ph$_3$P)$_4$ (2.10 g, 1.81 mmol, 0.025 eq) were added followed by a solution of 63 (22.81 g, 72.66 mmol) in dry THF (100 ml). The reaction mixture was then heated to 65° C. under argon overnight. After cooling the solution was acidified to pH 1 and extracted into EtOAc (300 ml). The aqueous layer was re-extracted with EtOAc (200 ml) and the combined organics washed with H$_2$O (2×500 ml) and brine (500 ml). The organic layer was dried over magnesium sulphate and concentrated under vacuum. The resulting residue was purified by column chromatography on silica eluting dichloromethane to give the acetophenone as a pale yellow solid (6.79 g, 30%). m.p. <25° C.

$\delta_H$ (400 MHz: CDCl$_3$): 0.88 (3H, t, J 6.7 Hz, CH$_2$CH$_3$), 1.22-1.31 (14H, m, 7×CH$_2$), 1.57-1.65 (2H, m, ArCH$_2$CH$_2$), 2.61 (2H, t, J 7.5 Hz, ArCH$_2$CH$_2$), 3.53 (3H, s, OCH$_3$), 4.71 (2H, s, OCH$_2$), 6.73 (1H, dd, J 1.6 Hz and 8.2 Hz, H-5), 6.83 (1H, d, J 1.4 Hz, H-3), 7.58 (1H, d, J 8.0 Hz, H-5), 11.98 (1H, s, OH). $\delta_C$ (100 MHz: CDCl$_3$): 14.05 (CH$_3$), 22.61 (CH$_2$), 29.16 (CH$_2$), 29.25 (CH$_2$), 29.37 (CH$_2$), 29.47 (CH$_2$), 29.53 (CH$_2$), 30.53 (CH$_2$), 31.83 (CH$_2$), 36.20 (CH$_2$), 59.48 (CH$_3$), 74.19 (CH$_2$), 115.48 (C), 117.93 (CH), 119.69 (CH), 128.53 (CH), 153.33 (C), 162.52 (C), 200.78 (C). m/z (EI): 306.1 (M$^+$, 10%), 261.1 (100), 147.0 (25), 45.0 (30). Found: 306.2194 C$_{19}$H$_{30}$O$_3$ requires (M$^+$) 306.2195. Found: C, 74.74%; H, 10.03%. C$_{19}$H$_{30}$O$_3$ requires C, 74.47%; H, 9.87%. $\upsilon_{max}$ (thin film)/cm$^{-1}$: 3039 (OH), 2925 (CH$_2$), 1648 (C=O). R$_f$ Silica DCM 0.26

1-(2'-[2'',4'',5''-trimethoxy-benzoyloxy]-4'-decyl-phenyl)-2-methoxy-ethanone (65)

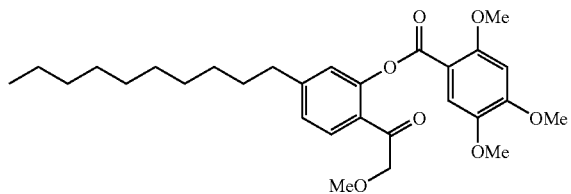

EDCI (860 mg, 4.49 mmol, 1.5 eq) was added to a solution of 64 (916 mg, 2.99 mmol, 1.0 eq), trimethoxybenzoic acid (634 mg, 2.99 mmol, 1.0 eq) and DMAP (36 mg, 0.30 mmol, 0.1 eq) in dry dichloromethane (10 ml) under argon at room temperature. The resulting solution was stirred overnight. The reaction mixture was then diluted with DCM (20 ml) and washed with brine (50 ml). The aqueous layer was re-extracted with DCM (20 ml) and the combined organics washed with brine (50 ml). The organic layer was then dried over magnesium sulfate and concentrated under vacuum. The resulting residue was purified by column chromatography on silica eluting EtOAc:Hexane 2:1 to give the ester as a pale yellow solid (1.01 g, 68%). m.p. 80-81° C.

$\delta_H$ (400 MHz: CDCl$_3$): 0.88 (3H, t, J 6.8 Hz, CH$_2$CH$_3$), 1.26-1.31 (14H, m, 7×CH$_2$), 1.60-1.67 (2H, m, ArCH$_2$CH$_2$), 2.66 (2H, t, J 7.6 Hz, ArCH$_2$CH$_2$), 3.38 (3H, s, OCH$_3$), 3.92 (3H, s, OCH$_3$), 3.94 (3H, s, OCH$_3$), 3.97 (3H, s, OCH$_3$), 4.56 (2H, s, OCH$_2$), 6.58 (1H, s, H-5''), 7.08 (1H, d, J 1.2 Hz, H-3'), 7.15 (1H, dd, J 1.2 Hz and 8.0 Hz, H-5'), 7.65 (1H, s, H-6''), 7.80 (1H, d, J 8.0 Hz, H-6'). $\delta_C$ (100 MHz: CDCl$_3$): 14.05 (CH$_3$), 22.61 (CH$_2$), 29.21 (CH$_2$), 29.24 (CH$_2$), 29.36 (CH$_2$), 29.47 (CH$_2$), 29.53 (CH$_2$), 30.75 (CH$_2$), 31.82 (CH$_2$), 35.74 (CH$_2$), 56.09 (CH$_3$), 56.41 (CH$_3$), 56.81 (CH$_3$), 59.19 (CH$_3$), 77.18 (CH$_2$), 97.35 (CH), 108.85 (C), 114.77 (CH), 123.79 (CH), 125.97 (CH), 126.53 (C), 129.69 (CH), 142.71 (C), 149.79 (2×C), 154.69 (C), 156.79 (C), 163.39 (C), 196.20 (C). m/z (EI): 500.3 (M$^+$, 5%), 261.1 (10), 195.1 (100). Found: 500.2776 C$_{29}$H$_{40}$O$_7$ requires (M$^+$) 500.2774. $\upsilon_{max}$ (golden gate)/cm$^{-1}$: 2913 (CH$_2$), 1747 (CO$_2$), 1685 (C=O). R$_f$ 0.31 silica (EtOAc:Hexane 2:1)

Synthesis of 1-(2'-hydroxy-4'-decylphenyl)-2-methoxy-3-(2'',4'',5''-trimethoxyphenyl)-propan-1,3-dione (67)

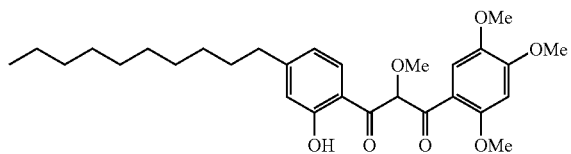

Lithium hexamethyldisilylazide (1.0 M solution in THF) (4.88 ml, 4.88 mmol, 3.0 eq) was added dropwise to a solution of 65 (814 mg, 1.63 mmol, 1.0 eq) in dry THF (6 ml) cooled to −20° C. and under argon. After 1 h. the reaction was quench with saturated NaHCO$_3$ solution (30 ml) and extracted in EtOAc (50 ml). The aqueous phase was re-extracted with EtOAc (20 ml) and the combined organics washed with brine (2×100 ml). The organic phase was then dried over magnesium sulfate and concentrated under vacuum to give the diketone as an off white solid suitably pure for the next step (717 mg, 88%). m.p. 99-101° C.

$\delta_H$ (400 MHz: CDCl$_3$): 0.88 (3H, t, J 6.8 Hz, CH$_2$CH$_3$), 1.26-1.31 (14H, m, 7×CH$_2$), 1.58-1.63 (2H, m, ArCH$_2$CH$_2$), 2.62 (2H, t, J 7.5 Hz, ArCH$_2$CH$_2$), 3.48 (3H, s, OCH$_3$), 3.62 (3H, s, OCH$_3$), 3.91 (3H, s, OCH$_3$), 3.92 (3H, s, OCH$_3$), 5.90 (1H, s, H-2), 6.37 (1H, s, H-3''), 6.80-6.82 (2H, m, H-3' and H-5'), 7.62 (1H, s, H-6''), 7.78 (1H, d, J 8.1 Hz, H-6'), 11.65 (1H, s, OH). $\delta_C$ (100 MHz: CDCl$_3$): 14.09 (CH$_3$), 22.65 (CH$_2$), 29.23 (CH$_2$), 29.29 (CH$_2$), 29.42 (CH$_2$), 29.52 (CH$_2$), 29.57 (CH$_2$), 30.55 (CH$_2$), 31.87 (CH$_2$), 36.26 (CH$_2$), 55.29 (CH$_3$), 56.14 (CH$_3$), 56.24 (CH$_3$), 58.89 (CH$_3$), 86.83 (CH), 95.70 (CH), 112.08 (C), 116.31 (C), 116.47 (C), 117.83 (CH), 119.94 (CH), 130.45 (CH), 138.10 (C), 143.68 (C), 153.29 (C), 154.92 (C), 163.15 (C), 191.92 (C), 198.68 (C). m/z (EI): 500.3 (M$^+$, 1%), 261.1 (10), 195.1 (100). Found: 500.2775 C$_{29}$H$_{40}$O$_7$ requires (M$^+$) 500.2774. $\upsilon_{max}$ (golden gate)/cm$^{-1}$: 2915 (CH$_2$), 1664 (C=O), 1631 (C=O). R$_f$ silica (EtOAc:Hexane 1:1) 0.41

Synthesis of 3,2',4',5'-tetramethoxy-7-decyl-flavone (69)

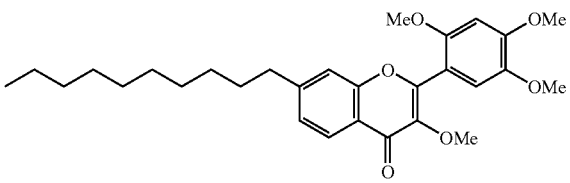

TMSOTf (0.245 ml, 1.35 mmol, 1.1 eq) was added slowly to a solution of 67 (614 mg, 1.23 mmol) in dry DCM (4 ml) at room temperature under argon. The yellow solution was then stirred for 1 h and then quenched with saturated NaHCO$_3$ solution (30 ml) and extracted into DCM (20 ml). The aqueous layer was re-extracted with DCM (20 ml) and the combined organics washed with brine (50 ml). The organic layer was then dried over magnesium sulfate and concentrated under vacuum. The residue was purified by column chromatography on silica eluting EtOAc:hexane 1:1 to give the flavone as a viscous yellow oil (409 mg, 69%).

$\delta_H$ (400 MHz: CDCl$_3$): 0.88 (3H, t, J 6.8 Hz, CH$_2$CH$_3$), 1.24-1.32 (14H, m, 7×CH$_2$), 1.63-1.70 (2H, m, ArCH$_2$CH$_2$), 2.72 (2H, t, J 7.5 Hz, ArCH$_2$CH$_2$), 3.82 (3H, s, OCH$_3$), 3.85 (3H, s, OCH$_3$), 3.87 (3H, s, OCH$_3$), 3.97 (3H, s, OCH$_3$), 6.64 (1H, s, H-3'), 7.00 (1H, s, H-6'), 7.21 (1H, dd, J 1.3 Hz and 8.2 Hz, H-6), 7.26 (1H, d, J 1.3 Hz, H-8), 8.18 (1H, d, J 8.2 Hz, H-5). $\delta_C$ (100 MHz: CDCl$_3$): 14.06 (CH$_3$), 22.63 (CH$_2$), 29.15 (CH$_2$), 29.26 (CH$_2$), 29.39 (CH$_2$), 29.49 (CH$_2$), 29.54 (CH$_2$), 30.87 (CH$_2$), 31.84 (CH$_2$), 35.98 (CH$_2$), 56.07 (CH$_3$), 56.56 (CH$_3$), 56.69 (CH$_3$), 60.28 (CH$_3$), 97.58 (CH), 111.42 (C), 113.62 (CH), 117.08 (CH), 122.29 (C), 125.39 (CH), 125.54 (CH), 141.73 (C), 142.93 (C), 149.39 (C), 151.68 (C), 152.38 (C), 155.41 (C), 155.86 (C), 174.75 (C). m/z (EI): 482.2 (M$^+$, 60%), 467.2 (75), 451.2 (100). Found: 482.2672 C$_{29}$H$_{38}$O$_6$ requires (M$^+$) 482.2668. $\upsilon_{max}$ (thin film)/cm$^{-1}$: 2927 (CH$_2$), 1644 (C=O). R$_f$ Silica (EtOAc:hexane 1:1) 0.31

Synthesis of 3,2',4',5'-tetrahydroxy-7-decyl-flavone (13g)

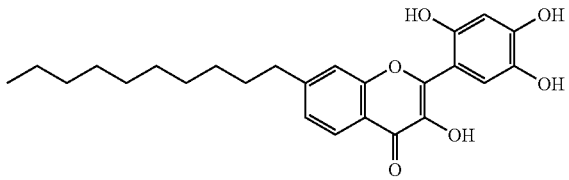

Boron tribromide (1.0 M solution in DCM) (4.0 ml, 4.06 mmol, 5.0 eq) was added slowly to a solution of 69 (392 mg, 0.81 mmol) in dry DCM (3 ml) at 0° C. under argon. The solution was then stirred overnight and then methanol (5 ml) added slowly. The solution was heated under reflux for 30 min. then concentrated under vacuum. Water (20 ml) was added to the residue and the flask placed in a sonic bath for 5 min. The resulting fine precipitate was filtered off and washed with water (10 ml) then freeze dried to give the flavonol as a red/brown amorphous solid (338 mg, 98%). m.p. decomp >90° C.

$\delta_H$ (400 MHz: D-6 DMSO): 0.84 (3H, t, J 6.7 Hz, CH$_2$CH$_3$), 1.22-1.28 (14H, m, 7×CH$_2$), 1.60-1.64 (2H, m, ArCH$_2$CH$_2$), 2.72 (2H, t, J 7.5 Hz, ArCH$_2$CH$_2$), 6.43 (1H, s, H-3'), 6.87 (1H, s, H-6'), 7.28 (1H, d, J 8.2 Hz, H-6), 7.39 (1H, 6, H-8), 8.00 (1H, d, J 8.2 Hz, H-5). $\delta_C$ (100 MHz: D-6 DMSO): 14.28 (CH$_3$), 22.42 (CH$_2$), 28.91 (CH$_2$), 29.01 (CH$_2$), 29.13 (CH$_2$), 29.30 (CH$_2$), 29.31 (CH$_2$), 30.70 (CH$_2$), 31.62 (CH$_2$), 35.37 (CH$_2$), 104.55 (CH), 108.65 (C), 116.77 (CH), 117.45 (CH), 120.26 (C), 124.94 (CH), 125.38 (CH), 138.07 (C), 138.28 (C), 148.14 (C), 148.90 (C), 149.05 (C), 149.10 (C), 155.43 (C), 172.59 (C). m/z (FAB): 427.4 ((M+H)$^+$, 100%). Found: 427.2120 C$_{25}$H$_{31}$O$_6$ requires ((M+H)$^+$) 427.2121. $\upsilon_{max}$ (golden gate)/cm$^{-1}$: 3226 (OH), 2919 (CH$_2$), 1558 (C=O).

EXAMPLE 14

1-(2'-[2",3",4"-trimethoxy-benzoyloxy]-4'-decyl-phenyl)-2-methoxy-ethanone 66

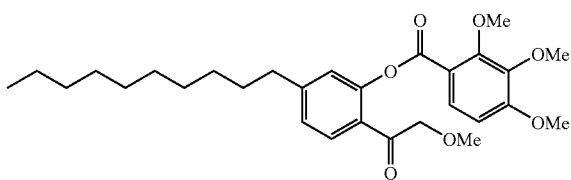

EDCI (914 mg, 4.77 mmol, 1.5 eq) was added to a solution of 64 (produced as described in Example 13) (973 mg, 3.18 mmol, 1.0 eq), trimethoxybenzoic acid (675 mg, 3.18 mmol, 1.0 eq) and DMAP (39 mg, 0.32 mmol, 0.1 eq) in dry dichloromethane (10 ml) under argon at room temperature. The resulting solution was stirred overnight. The reaction mixture was then diluted with DCM (20 ml) and washed with brine (50 ml). The aqueous layer was re-extracted with DCM (20 ml) and the combined organics washed with brine (50 ml). The organic layer was then dried overvmagnesium sulfate and concentrated under vacuum.

The resulting residue was purified by column chromatography on silica eluting EtOAc:Hexane 1:1 to give the ester as a colourless oil (927 mg, 58%).

$\delta_H$ (400 MHz: CDCl$_3$): 0.88 (3H, t, J 6.8 Hz, CH$_2$CH$_3$), 1.25-1.31 (14H, m, 7×CH$_2$), 1.60-1.68 (2H, m, ArCH$_2$CH$_2$), 2.67 (2H, t, J 7.6 Hz, ArCH$_2$CH$_2$), 3.39 (3H, s, OCH$_3$), 3.91 (3H, s, OCH$_3$), 3.95 (3H, s, OCH$_3$), 3.98 (3H, s, OCH$_3$), 4.55 (2H, s, OCH$_2$), 6.78 (1H, d, J 8.8 Hz, H-5"), 7.07 (1H, d, J 1.2 Hz, H-3'), 7.16 (1H, dd, J 1.2 Hz and 8.0 Hz, H-5'), 7.77 (1H, d, J 8.0 Hz, H-6'), 7.88 (1H, d, J 8.8 Hz, H-6"). $\delta_C$ (100 MHz: CDCl$_3$): 14.03 (CH$_3$), 22.59 (CH$_2$), 29.18 (CH$_2$), 29.23 (CH$_2$), 29.34 (CH$_2$), 29.45 (CH$_2$), 29.50 (CH$_2$), 30.70 (CH$_2$), 31.81 (CH$_2$), 35.70 (CH$_2$), 56.10 (CH$_3$), 59.17 (CH$_3$), 60.98 (CH$_3$), 61.84 (CH$_3$), 76.87 (CH$_2$), 107.06 (CH), 116.46 (C), 123.76 (CH), 126.03 (CH), 126.39 (CH), 127.83 (CH), 129.62 (CH), 143.06 (C), 149.61 (C), 149.92 (C), 155.50 (C), 158.00 (C), 163.25 (C), 196.00 (C). m/z (EI): 500.3 (M$^+$, 5%), 261.1 (15), 195.1 (100). Found: 500.2772 C$_{29}$H$_{40}$O$_7$ requires (M$^+$) 500.2774. $\upsilon_{max}$ (thin film)/cm$^{-1}$: 2927 (CH$_2$), 1743 (CO$_2$), 1702 (C=O). R$_f$ Silica (EtOAc:Hexane 1:1) 0.30

Synthesis of 1-(2'-hydroxy-4'-decylphenyl)-2-methoxy-3-(2",3",4"-trimethoxyphenyl)-propan-1,3-dione (68)

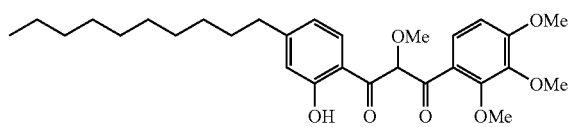

Lithium hexamethyldisilylazide (1.0 M solution in THF) (3.84 ml, 3.84 mmol, 3.0 eq) was added dropwise to a solution of 66 (641 mg, 1.28 mmol, 1.0 eq) in dry THF (5 ml) cooled to −20° C. and under argon. After 1 h. the reaction was quench with saturated NaHCO$_3$ solution (30 ml) and extracted in EtOAc (50 ml). The aqueous phase was re-extracted with EtOAc (20 ml) and the combined organics washed with brine (2×100 ml). The organic phase was then dried over magnesium sulfate and concentrated under vacuum. The resulting bright yellow oil was purified by column chromatography on silica eluting EtOAc:Hexane 1:2 to give the diketone as a yellow solid (387 mg, 60%). m.p. 60-62° C.

$\delta_H$ (400 MHz: CDCl$_3$): 0.88 (3H, t, J 6.8 Hz, CH$_2$CH$_3$), 1.26-1.31 (14H, m, 7×CH$_2$), 1.58-1.63 (2H, m, ArCH$_2$CH$_2$), 2.60 (2H, t, J 7.5 Hz, ArCH$_2$CH$_2$), 3.57 (3H, s, OCH$_3$), 3.79 (3H, s, OCH$_3$), 3.80 (3H, s, OCH$_3$), 3.91 (3H, s, OCH$_3$), 5.58 (1H, s, H-2), 6.73 (1H, d, J 8.8 Hz, H-5"), 6.76 (1H, dd, J 1.6 Hz and 8.4 Hz, H-5'), 6.80 (1H, d, J 1.6 Hz, H-3'), 7.66 (1H, d, J 8.8 Hz, H-6"), 7.81 (1H, d, J 8.4 Hz, H-6'), 11.72 (1H, s, OH). $\delta_C$ (100 MHz: CDCl$_3$): 14.08 (CH$_3$), 22.65 (CH$_2$), 29.24 (CH$_2$), 29.29 (CH$_2$), 29.41 (CH$_2$), 29.51 (CH$_2$), 29.56 (CH$_2$), 30.50 (CH$_2$), 31.86 (CH$_2$), 36.28 (CH$_2$), 56.13 (CH$_3$), 58.77 (CH$_3$), 60.80 (CH$_3$), 61.01 (CH$_3$), 88.19 (CH), 107.14 (CH), 116.20 (C), 117.76 (CH), 119.90 (CH), 123.04 (C), 126.21 (CH), 130.79 (CH), 141.29 (C), 153.59 (C), 153.66 (C), 158.36 (C), 163.28 (C), 193.54 (C), 198.84 (C). m/z (EI): 500.3 (M$^+$, 1%), 261.1 (5), 195.1 (100). Found: 500.2773 C$_{29}$H$_{40}$O$_7$ requires (M$^+$) 500.2774. $\upsilon_{max}$ (thin film)/cm$^{-1}$: 3403 (OH), 2927 (CH$_2$), 1685 (C=O), 1637 (C=O). R$_f$ silica (EtOAc:Hexane 1:2) 0.29

Synthesis of 3,2',3',4'-tetramethoxy-7-decyl-flavone (70)

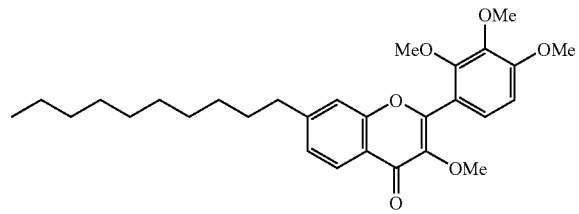

TMSOTf (0.12 ml, 0.66 mmol, 1.1 eq) was added slowly to a solution of 68 (299 mg, 0.59 mmol) in dry DCM (2 ml) at room temperature under argon. The yellow solution was then stirred for 1 h and then quenched with saturated NaHCO$_3$ solution (20 ml) and extracted into DCM (20 ml). The aqueous layer was re-extracted with DCM (20 ml) and the combined organics washed with brine (50 ml). The organic layer was then dried over magnesium sulfate and concentrated under vacuum to give the flavone as a viscous yellow oil (251 mg, 87%).

$\delta_H$ (400 MHz: CDCl$_3$): 0.88 (3H, t, J 6.8 Hz, CH$_2$CH$_3$), 1.26-1.31 (14H, m, 7×CH$_2$), 1.62-1.70 (2H, m, ArCH$_2$CH$_2$), 2.72 (2H, t, J 7.5 Hz, ArCH$_2$CH$_2$), 3.80 (3H, s, OCH$_3$), 3.93 (3H, s, OCH$_3$), 3.94 (3H, s, OCH$_3$), 3.95 (3H, S, OCH$_3$), 6.78 (1H, d, J 8.7 Hz, H-5'), 7.19-7.25 (3H, m, H-6, 8 and 6'), 8.18 (1H, d, J 8.2 Hz, H-5). $\delta_C$ (100 MHz: CDCl$_3$): 14.06 (CH$_3$), 22.63 (CH$_2$), 29.15 (CH$_2$), 29.39 (CH$_2$), 29.49 (CH$_2$), 29.54 (CH$_2$), 29.54 (CH$_2$), 30.89 (CH$_2$), 31.84 (CH$_2$), 35.99 (CH$_2$), 56.07 (CH$_3$), 60.40 (CH$_3$), 60.88 (CH$_3$), 61.48 (CH$_3$), 107.00 (CH), 117.03 (CH), 118.04 (C), 122.47 (C), 125.40 (CH), 125.46 (CH), 125.60 (CH), 141.69 (C), 142.37 (C), 149.55 (C), 152.36 (C), 155.61 (C), 155.75 (C), 155.61 (C), 174.76 (C). m/z (EI): 482.2 (M$^+$, 60%), 467.2 (75), 451.2 (100). Found: 482.2666 C$_{29}$H$_{38}$O$_6$ requires (M$^+$) 482.2669. $\upsilon_{max}$ (thin film)/cm$^{-1}$: 2929 (CH$_2$), 1621 (C=O). R$_f$ silica (EtOAc: Hexane 1:1) 0.44

EXAMPLE 15

1-(2-Allyloxy-phenyl)-ethanone

To a stirring suspension of 2-hydroxyacetophenone 72 (5 ml, 42 mmol) and potassium carbonate (6.516 g, 47 mmol, 1.1 equ) in acetone (30 ml) was added allyl bromide (4 ml, 46 mmol, 1.1 equ). The reaction was heated to reflux for 20 hours. The reaction was then concentrated in vacuo, taken up in water and extracted into ethyl acetate (2×). The organic layer was dried (MgSO$_4$) and concentrated in vacuo to give an yellow oil. This was taken up in diethyl ether, washed with 1M potassium hydroxide then dried (MgSO$_4$) and concentrated in vacuo to give 1-(2-allyloxy-phenyl)-ethanone (3.70 g, 51%) as a pale yellow oil.

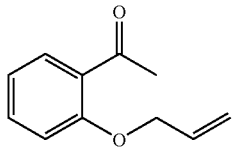

$^1$H nmr (400 MHz, CDCl$_3$) 2.64 (s, 3H) 4.65 (td, 2H, 1.5+5.3 Hz) 5.32 (ddd, 1H, 1.4+1.3+10.5 Hz) 5.44 (ddd, 1H, 1.5+1.6+17 Hz) .6.04-6.14 (m, 1H) 6.93-7.02 (m, 2H) 7.44 (td, 1H, 1.9+7.3 Hz) 7.73 (dd, 1H, 1.8+7.7 Hz). $^{13}$C nmr (100 MHz, CDCl$_3$) 32.38 (CH$_3$) 69.78 (CH$_2$) 113.15 (CH) 118.58 (CH$_2$) 121.17 (CH) 130.81 (CH) 133.02 (CH) 133.90 (CH) 158.29 (Q) 200.32 (Q). EI+ 176.1 (21%, M$^+$) 161.1 (100%, [M–Me]$^+$) 121.0 (100%, [M-(Allyl+Me)]$^+$) CLLH$_{12}$O$_2$ Calc. 176.0837 Found 176.0838.

1-(3-Allyl-2-hydroxy-phenyl)-ethanone (73)

1-(2-Allyloxy-phenyl)-ethanone (2.518 g, 14 mmol) was heated to 200° C. for 44 hours to give 1-(3-allyl-2-hydroxyphenyl)-ethanone 73 (2.518 g, 100%).

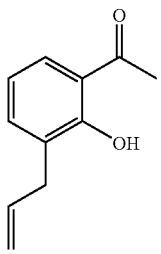

$^1$H nmr (400 MHz, CDCl$_3$) 2.63 (s, 3H) 3.43 (d, 2H, 6.6 Hz) 5.06-5.11 (m, 1H) 5.95-6.06 (m, 1H) 6.85 (t, 1H, 7.7 Hz) 7.36 (d, 1H, 7.2 Hz) 7.62 (dd, 1H, 1.4+8 Hz). $^{13}$C nmr (100 MHz, CDCl$_3$) 27.17 (CH$_3$) 33.80 (CH$_2$) 116.39 (CH$_2$) 118.81 (CH) 119.63 (Q) 129.20 (CH) 129.79 (Q) 136.49 (CH) 136.87 (CH) 160.81 (Q) 205.15 (Q). EI+ 176.1 (90%, M$^+$) 161.1 (100%, [M–Me]$^+$) C$_{11}$H$_{12}$O$_2$ Calc. 176.0837 Found 176.0837.

1-(2-Hydroxy-3-allyl-phenyl)-3-(2,4,5-trimethoxyphenyl)-propenone (74)

To a stirring suspension of 1-(3-allyl-2-hydroxy-phenyl)-ethanone 73 (1.779 g, 27 mmol) and 2,4,5-trimethoxy benzaldehyde (5.89 g, 30 mmol, 1.1 equ) in ethanol (50 ml) was added potassium hydroxide (3.23 g, 58 mmol, 2.1 equ). The reaction mixture was stirred for 191 hours then acidified (2 M HCl) and extracted with ethyl acetate (3×). The combined organic layers were then washed with water and brine then dried (MgSO$_4$) and concentrated in vacuo to give 1-(2-hydroxy-3-allyl-phenyl)-3-(2,4,5-trimethoxy-phenyl)-propenone 74 (11.165 g, 116%) as an orange solid.

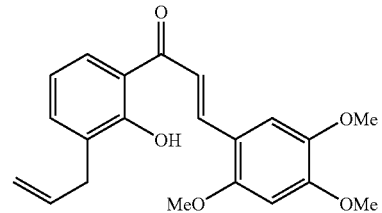

$^1$H nmr (400 MHz, CDCl$_3$) 3.47 (d, 2H, 6.6 Hz) 3.92 (s, 3H) 3.94 (s, 3H) 3.96 (s, 3H) 5.08-5.14 (m, 2H) 5.99-6.10 (m, 1H) 6.53 (s, 1H) 6.88 (t, 1H, 7.7 Hz) 7.13 (s, 1H) 7.36 (d, 1H, 6.5 Hz) 7.63 (d, 1H, 15.5 Hz) 7.82 (dd, 1H, 1.4+8.1 Hz) 8.21 (d, 1H, 15.5 Hz) 13.43 (s, 1H). $^{13}$C nmr (100 MHz, CDCl$_3$) 33.94 (CH$_2$) 56.49 (CH$_3$) 56.73 (CH$_3$) 57.08 (CH$_3$) 97.12 (CH) 112.20 (CH) 115.69 (Q) 116.31 (CH$_2$) 118.49 (CH) 118.57 (CH) 120.19 (Q) 128.04 (CH) 129.80 (Q) 136.29 (CH) 136.68 (CH) 138.51 (Q) 141.12 (CH) 143.71 (Q) 153.33 (Q) 155.46 (CH) 161.97 (Q) 194.66 (Q). EI+ 354.4 (69%, M$^+$) 323.3 (100%, [M–OMe]$^+$) C$_{21}$H$_{22}$O$_5$ Calc. 354.1467 Found 354.1468.

8-Allyl-3-hydroxy-2-(2,4,5-trimethoxy-phenyl)-chromen-4-one (75)

To a stirring solution of 1-(2-hydroxy-3-allyl-phenyl)-3-(2,4,5-trimethoxy-phenyl)-propenone 74 (11.15 g, 31 mmol) in methanol (300 ml) and 16% aqueous sodium hydroxide solution (37 ml, 148 mmol, 4.7 equ) at 0° C. was added 15% aqueous hydrogen peroxide (37 ml, 163 mmol, 5.2 equ) dropwise. The solution was stirred at 0° C. for ten minutes then sealed and placed in a refrigerator for 23 hours. The reaction was then acidified (2 M HCl) and extracted into chloroform (3×). The organic layer was then washed with brine, dried (MgSO$_4$) and concentrated to give an orange solid. This was taken up in methanol (300 ml) and 16% aqueous sodium hydroxide solution (37 ml, 148 mmol, 4.7 equ) at 0° C., then 15% aqueous hydrogen peroxide (37 ml, 163 mmol, 5.2 equ) was added and the solution stirred at 0° C. for the 5 minutes then sealed and place in a refrigerator for 18 hours. The reaction was then acidified (2 M HC1) and extracted into dichloromethane (3×). The organic layer was then dried (MgSO$_4$) and concentrated to give an orange solid. Recrystallisation (ethanol) yielded 8-allyl-3-hydroxy-2-(2,4,5-trimethoxy-phenyl)-chromen-4-one 75 (4.815 g, 42%) as a yellow solid.

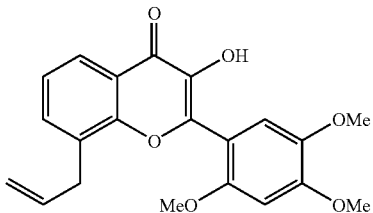

$^1$H nmr (400 MHz, CDCl$_3$) 3.66 (d, 2H, 6.5 Hz) 3.89 (s, 6H) 3.98 (s, 3H) 5.07-5.12 (m, 2H) 6.00-6.11 (m, 1H) 6.53 (brs, 1H) 6.67 (s, 1H) 7.19 (s, 1H) 7.34 (t, 1H, 7.7 Hz) 7.53 (dd, 1H, 1.4+7.1 Hz) 8.15 (dd, 1H, 1.6+8.0 Hz). $^{13}$C nmr (100 MHz, CDCl$_3$) 34.15 (CH$_2$) 56.51 (CH$_3$) 56.94 (CH$_3$) 57.14 (CH$_3$) 98.19 (CH) 111.37 (Q) 114.00 (CH) 116.98 (CH$_2$) 121.74 (Q) 124.05 (CH) 124.50 (CH) 130.13 (Q) 133.72 (CH) 135.97 (CH) 138.75 (Q) 143.49 (Q) 145.88 (Q) 152.32 (Q) 152.94 (Q) 154.26 (Q) 173.76 (Q). EI+ 368.4 (100%, M$^+$) 373.3 (87%, [M–OMe]$^+$) C$_{21}$H$_{20}$O$_6$ Calc. 368.1260 Found 368.1259.

Tetradec-7-ene

A mixture of 1-octene (7.15 g, 64 mmol) and Grubbs' catalyst (0.030 g, 0.04 mmol, 0.0006 equ) was stirred under a static vacuum for 15 hours, then passed through a plug of silica eluting with hexane. Concentration gave tetradec-7-ene (4.982 g, 80%) as a colourless liquid.

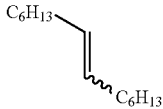

$^1$H nmr (400 MHz, CDCl$_3$) 0.86-0.90 (m, 6H) 1.21-1.41 (m, 16H) 1.94-2.04 (m, 4H) 5.31-5.43 (m, 2H). $^{13}$C nmr (100 MHz, CDCl$_3$) 14.48 (CH$_3$) 23.04 (CH$_2$) 27.60 (CH$_2$) 29.23 (CH$_2$) 29.38 (CH$_2$) 30.02 (CH$_2$) 30.13 (CH$_2$) 32.15 (CH$_2$) 32.17 (CH$_2$) 33.00 (CH$_2$) 130.28 (CH) 130.75 (CH). EI+ 196 (9%, M$^+$) C$_{14}$H$_{28}$ Calc. 196.2191 Found 196.2191.

3-Hydroxy-8-non-2-enyl-2-(2,4,5-trimethoxy-phenyl)-chromen-4-one (76)

To a stirring solution of tetradec-7-ene (0.539 g, 2.75 mmol, 2.1 equ) and Grubbs' first generation catalyst (0.029 g, 0.04 mmol, 0.03 equ) in dichloromethane (13.5 ml) under argon was added 8-allyl-3-hydroxy-2-(2,4,5-trimethoxy-phenyl)-chromen-4-one 75 (0.479 g, 1.3 mmol). The reaction was heated to reflux for 5.5 hours then concentrated in vacuo to give a brown solid. Recrystallisation (ethanol) yielded 3-hydroxy-8-non-2-enyl-2-(2,4,5-trimethoxy-phenyl)-chromen-4-one 76 (0.258 g, 26%) as an lilac solid.

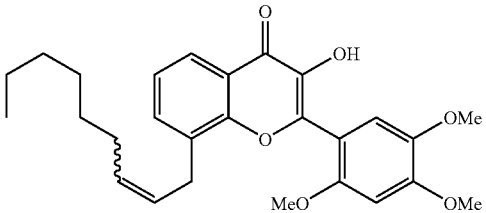

$^1$H nmr (400 MHz, CDCl$_3$) 0.84-0.90 (m, 3H) 1.21-1.47 (m, 8H) 1.97-2.02 (m, 2H) 3.58-3.71 (m, 2H) 3.75-4.07 (m, 11H) 5.37-5.40 (m, 0.25H) 5.49-5.66 (m, 1H) 5.75-5.78 (m, 0.75H) 6.50-6.54 (m, 2H) 6.64 (d, 1H, 19.2 Hz) 7.09 (s, 0.25H) 7.18 (d, 0.75H, 11Hz) 7;24-7.35 (m, 1H) 7.40-7.53 (m, 1H) 8.08-8.14 (m, 1H).

3-Hydroxy-8-nonyl-2-(2,4,5-trimethoxy-phenyl)-chromen-4-one (77)

A stirring suspension of 3-hydroxy-8-non-2-enyl-2-(2,4,5-trimethoxy-phenyl)-chromen-4-one 76 (0.258 g, 0.6 mmol) and 10% palladium on carbon (0.024 g) in ethyl acetate (30 ml) was placed under an atmosphere of hydrogen for 43 hours. The reaction was filtered through celite, the residue washed with ethyl acetate and the combined filtrates concentrated in vacuo to give a grey solid. Recrystallisation (petrol: ethyl acetate 2:1) yielded 3-hydroxy-8-nonyl-2-(2,4,5-trimethoxy-phenyl)-chromen-4-one 77 (0.212 g, 82%) as an off-white solid.

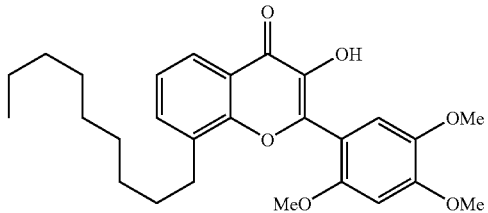

$^1$H nmr (400 MHz, CDCl$_3$) 0.87 (t, 3H, 6.7 Hz) 1.18-1.39 (m, 12H) 1.68-1.72 (m, 2H) 2.88 (t, 2H, 7.6 Hz) 3.88 (s, 3H) 3.89 (s, 3H) 3.98 (s, 3H) 6.53 (brs, 1H) 6.67 (s, 1H) 7.18 (s, 1H) 7.32 (t, 1H, 7.7 Hz) 7.50 (d, 1H, 6.2 Hz) 8.12 (d, 1H, 6.6 Hz)

8-Nonyl-3-hydroxy-2-(3,4,5-trihydroxy-phenyl)-chromen-4-one (14g)

To a stirring solution of 3-hydroxy-8-nonyl-2-(2,4,5-trimethoxy-phenyl)-chromen-4-one 77 (0.209 g, 0.5 tmol) in dichloromethane (15 ml) under Ar at 0° C. was added boron tribromide in dichloromethane (1.0M, 2.3 ml, 2.3 mmol, 5 equ). The mixture was warmed to room temperature and then stirred for 18 hours. Methanol (7 ml) was then added. The reaction was heated to reflux for 2 hours, then concentrated in vacuo to give a red oil. Water (25 ml) was added then extracted into ethyl acetate (3×). The organic layer was washed with brine then dried (MgSO$_4$) and concentrated in vacuo to give 14 g (0.203 g, 107%) as a brown solid.

The substituted flavonol 14g was further purified by treatment with acetic anhydride (6 eq.) and N,N-dimethyl-4-aminopyridine (0.05 eq.) in pyridine (60 eq.). When the reaction was complete, this was diluted with ethyl acetate and washed with dilute hydrochloric acid and saturated sodium bicarbonate solution. The organic solution was then dried (MgSO$_4$) and concentrated to give the crude tetraacetate derivative. Recrystallization from methanol gave the pure substituted tetraacetate, which was deprotected by heating in methanol (ca. 0.05M) containing catalytic concentrated hydrochloric acid for 1 hour. Dilution with water gave the substituted flavonol 14g as a fine yellow precipitate that was collected by filtration or extraction into ethyl acetate.

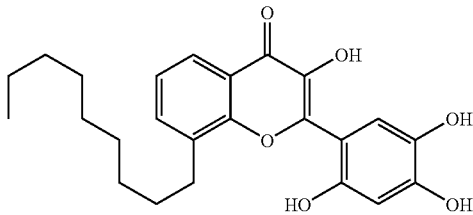
¹H nmr (400 MHz, CD₃SOCD₃) 0.83 (t, 3H, 6.7 Hz) 1.17-1.29 (m, 12H) 1.61-1.65 (m, 2H) 2.84 (t, 2H, 7.4 Hz) 7.01 (s, 1H) 7.37 (t, 1H, 1.6 Hz) 7.60 (d, 1H, 7.1 Hz) 7.96 (dd, 1H, 1.4+8.0 Hz) 9.45 (s, 1H) 9.65 (s, 1H). ¹³C nmr (100 MHz, D₃CSOCD₃) 14.31 (CH₃) 22.42 (CH₂) 28.94 (CH₂) 28.98 (CH₂) 29.02 (CH₂) 29.07 (CH₂) 29.26 (CH₂) 29.43 (CH₂) 31.61 (CH₂) 101.53 (Q) 109.72 (Q) 114.69 (CH) 122.27 (Q) 122.78 (CH) 124.31 (CH) 132.25 (Q) 133.39 (CH) 138.79 (Q) 146.10 (Q) 146.88 (Q) 153.54 (Q) 173.09 (Q). EI+ 491.3 (14%) 413.4 (1%, [M+H]⁺) 85.6 (100%).
The reactions are summarised in the following scheme:
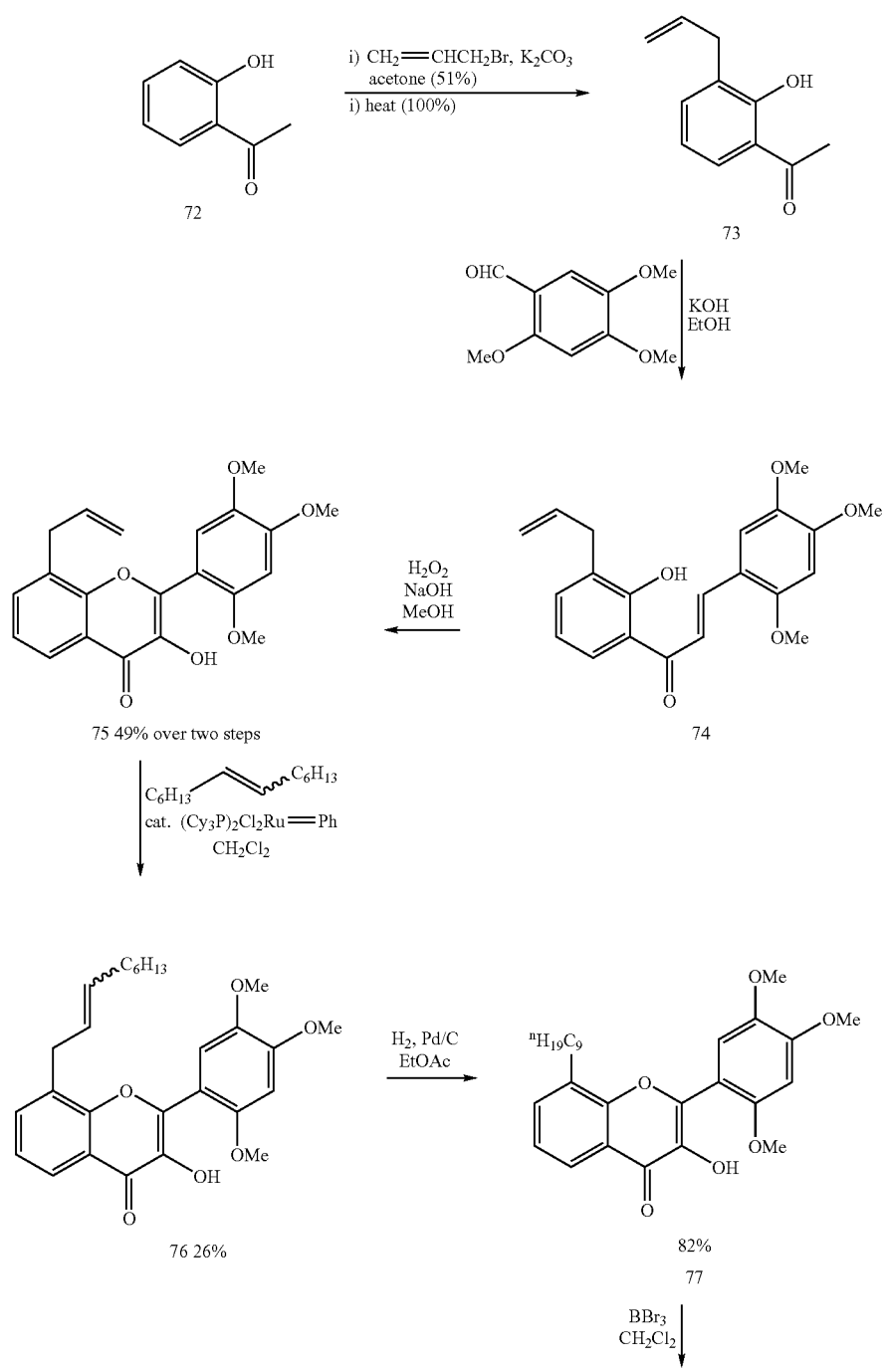

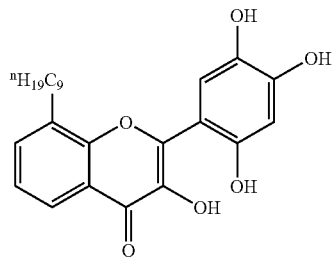
14g
EXAMPLE 15
A 9-C alkyl chain compound was prepared as described in Example 6. The reaction is summarised by the scheme given below:
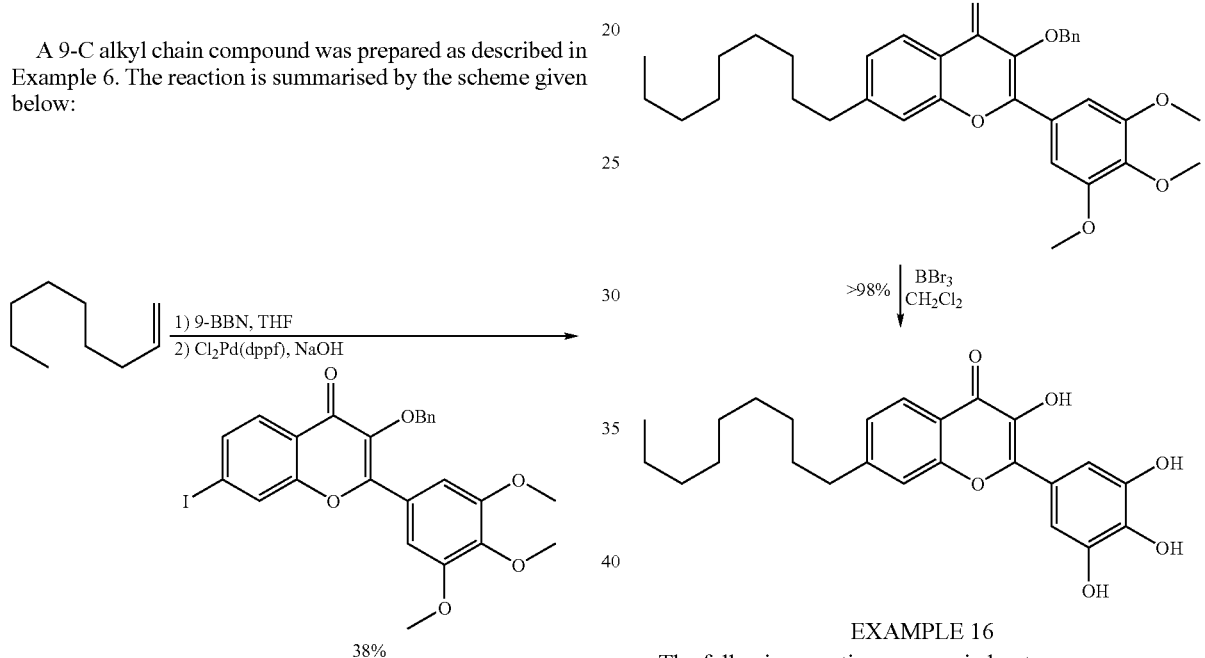
EXAMPLE 16
The following reaction was carried out.
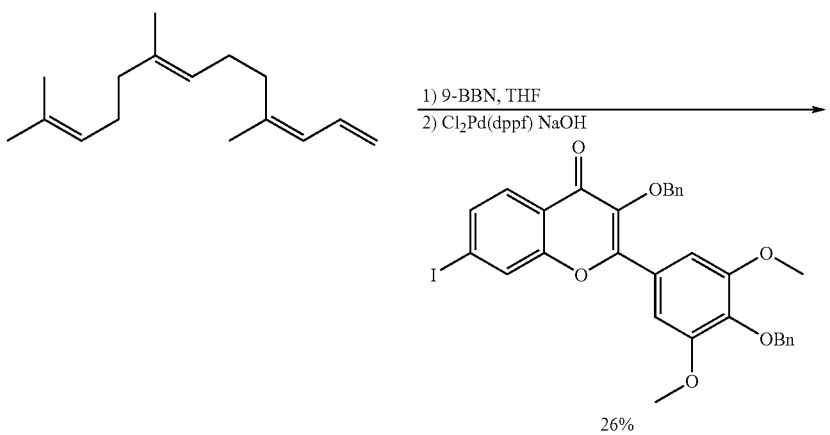

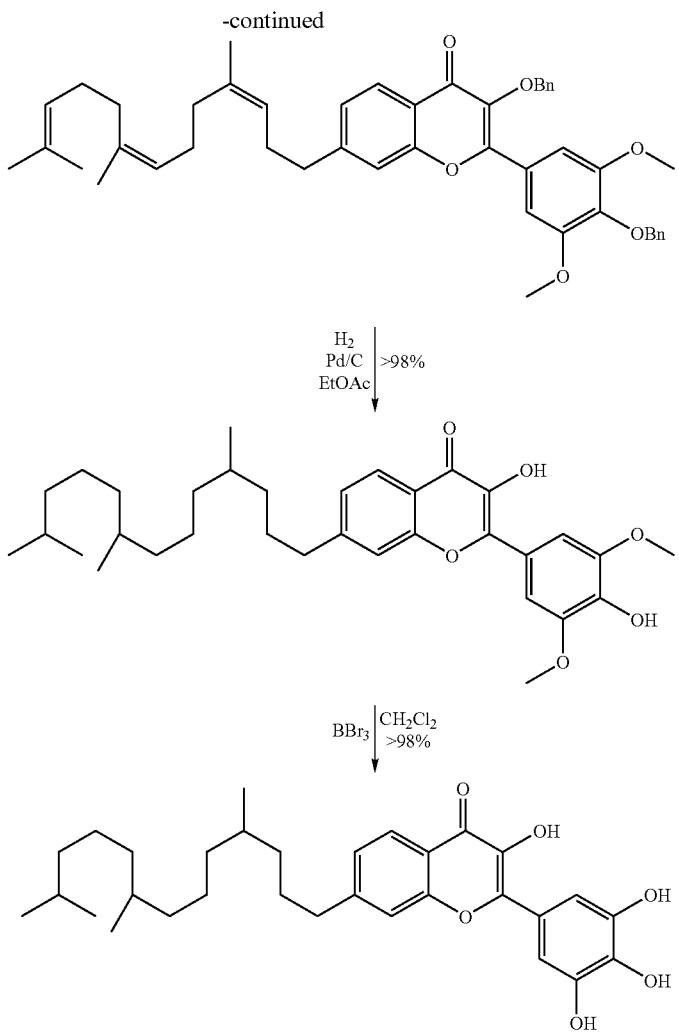

EXAMPLE 17

Within a biological system where a number of polyphenols may be present at similar concentrations, antioxidant efficacy may be predominantly governed by reaction kinetics rather than stoichiometry. Consequently, the antioxidant potential of thirteen flavonoids and vitamin E were assessed and their kinetic and stochiometric reduction of a synthetic radical using stopped-flow electron spin resonance (ESR) spectroscopy has been compared. The radical used was galvinoxyl (Galv-O°), (2,6-di-tert-butyl-α-(3,5-di-tert-butyl-4-oxo-2,5-cyclohexadien-1-ylidene)-p-tolyloxy) shown below:

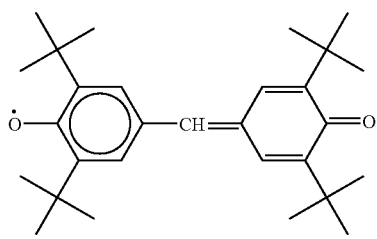

Galvinoxyl is resonance-stabilised and sterically-protected, and so displays little self-reactivity in solution, is reduced by H-atom transfer reactions in the presence of phenolic compounds.

Galv-O°+Phenol-OH⇌Galv-OH+phenol-O°

The process is governed by the O—H bond dissociation enthalpy of the donor. Galvinoxyl has a well-defined ESR spectrum and this property was used to calculate second order rate constants, as well as establishing stoichiometry, for the reaction with phenolic compounds.

Materials

Tamarixetin and myricetin-3',4',5'-trimethylether were purchased from Indofine Chemical Co. (Somerville, USA). The remaining flavonoids, d-α-tocopherol and galvinoxyl (2,6-di-tert-butyl-α-(3,5-di-tert-butyl-4-oxo-2,5-cyclohexadien-1-ylidene)-p-tolyloxy) were purchased from Sigma-Aldrich Chemical Co. (Poole, Dorset, UK) and ethanol (>99.7%) from BDH Laboratory Supplies (Poole, Dorset, UK). Reagents were used without further purification.

Methods

Kinetic Measurements

Ethanolic solutions of flavonoid (0.2 mM) and galvinoxyl (0.2 mM) were de-oxygenated under a stream of nitrogen gas.

Aliquots (6 ml) were transferred to Hamilton gas-tight syringes (10 ml) coupled to a pneumatic ram and connected to a two-stream ESR quartz flow-cell. In situ reaction at 20° C.±2° C. between the flavonoid and galvinoxyl was initiated by rapidly evacuating the syringes. Spectra and decay curves were obtained on a Bruker ECS 106 spectrometer operating at ca. 9.5 GHz (X-band) and equipped with a TMiio cavity. Decay curves were obtained by operating in timesweep mode with the static field set at the resonance maximum of the galvinoxyl signal.

Stoichiometric Measurements

Ethanolic solutions of flavonoids (0.1 mM) were prepared. Aliquots (3 ml) of an ethanolic galvinoxyl solution (0.5 mM) were mixed with an equal volume of flavonoid solution then transferred to an ESR quartz cell. The spectra and reaction stoichiometry were evaluated. In brief, the spectra of the unreacted galvinoxyl were obtained 5 minutes from mixing, by which time equilibration was complete. The galvinoxyl concentrations remaining were calculated by double integration of the signal and comparing with the control experiment where ethanol was added to the galvinoxyl solution instead of flavonoid solution.

Results

The ESR spectrum of galvinoxyl in an ethanolic solution consists of a doublet of quintets (FIG. 1) which arise from the interaction of the unpaired electron spin with the nuclear spins of the proton on the central carbon and the four equivalent aromatic ring protons. In the presence of a hydrogen donating compound, such as quercetin, the resonances decay as reduction of the radical proceeds. Data from all the decay curves gave a good linear fit to the second-order integrated rate expression, with the average correlation coefficient for each. set of replicates being greater than 0.970. However, there were marked differences between the flavonoids in the kinetics of the reduction of the galvinoxyl free radical. Myricetin and morin were, by far, the fastest toE react whereas hesperitin and apigenin showed little reactivity. Ranking of reaction rates as second order rate constants was: myricetin>morin>quercetin>fisetin≈catechin>kaempferol≈luteolin>rutin>taxifolin>tamarixetin>myricetin-3',4',5'-trimethylether>datiscetin>galangin>hesperitin≈apigenin. Reaction rates of eight of the flavonoids were greater than that for vitamin E.

The stoichiometry of the reaction of these compounds with the galvinoxyl free radical was determined by adding the flavonoid, or vitamin E, to an excess of the radical and allowing the reaction to proceed to the endpoint. This resulted in a ranking of antioxidant capacity which differed from the kinetic ranking i.e. myricetin>fisetin>quercetin≈luteolin>rutin>catechin>taxifolin>kaempferol≈morin>datiscetin>tamarixetin>myricetin-3',4',5'-trimethylether≈galangin>hesperitin>apigenin. In particular, the reaction of morin with galvinoxyl had the second fastest rate of all compounds, but was only ranked eighth equal in terms of the number of radicals reduced. Seven of the flavonoids had a greater reaction stoichiometry than vitamin E. Datiscetin, galangin, hesperitin and apigenin were the four lowest ranked of all the compounds in both the kinetic and stoichiometric measurements of antioxidant potential.

Discussion

A large number of natural phenolic compounds in fruit, vegetables, tea and wines have antioxidant activity due to their hydrogen donor activity and their ability to complex transition metal ions. In addition to the location and total number of hydroxyl groups, the solubility of the phenolics in the test medium may significantly affect their ability to act as antioxidants. For example, antioxidant activity of flavonoids in lard appears to be related to the number of ortho-dihydroxy groupings in the A and B-rings whereas a lack of conjugation between the B and C-rings is a major influence in aqueous media. The kinetic measurements in the present Application indicate that reactivity of the flavonoids with galvinoxyl in an organic medium is highly-dependent on the configuration of OH groups on the B and C-ring systems.

Galangin, which has no OH groups on the B-ring reacted only very slowly. However, addition of an OH group to the 4' position (position 12 in Formula 1) (kaempferol) increased the rate by a factor of about 70. The presence of an OH group on the C-ring was also important because the reaction with apigenin, which has the 4'-OH group (position 12 in Formula 1), but no OH at the 3-position on the C-ring, was slow, whereas the rate of reaction with kaempferol, which has both of these hydroxyl groups, was almost 250-fold greater.

The importance of further addition of hydroxyl groups to the B-ring was illustrated when comparing luteolin to apigenin. Luteolin is apigenin with an OH added ortho- to the 4'-OH (position 12 in Formula 1). The presence of this catechol function imparts significant activity in its own right as luteolin, which lacks the 3-OH, reacted with galvinoxyl at a rate similar to kaempferol. However, the ability of the 3-OH to enhance reactivity was demonstrated by the doubling of the rate constant in quercetin compared with luteolin. The difference in rate constant between quercetin and rutin also illustrated the influence that a group at the 3-position has on the kinetics of the reaction of flavonoids with galvinoxyl.

Substitution of the 3-OH of quercetin by an ether-linked sugar group (rutin) caused an approximate 3-fold decrease in the rate of reaction, although the rate constant was still greater than those for apigenin, hesperitin, galangin, datiscetin, taxifolin and vitamin E. By comparison with luteolin, the increased reaction rate of quercetin may be ascribed to electron donation by the 3-OH through the resonance effect, as the B- and C-rings of the flavonoids are linked by an extended, conjugated, π-electron system. In the case of rutin, despite the electron donating ability of the ether group, the rate is lower than that of luteolin. The importance of conjugation is further highlighted by the 7-fold diminution in rate observed when the C-ring 2,3 bond of quercetin is saturated (taxifolin). More difficult to explain is the activity retained by (+)-catechin which also lacks the 2,3 double bond. Catechin differs from taxifolin by the absence of the C-ring carbonyl group (and use of the single stereoisomer rather than racemic mixture). It may be that the hydrogen of the 3-OH is in close enough proximity to the B-ring to interact and increase the ability of the ring to sustain unpaired electron spin density. Thus a second mechanism to enhance reactivity may operate independent of resonance stabilisation through the 2,3 double bond. With taxifolin, intra-molecular hydrogen bonding of the 3-OH to the carbonyl would inhibit this mechanism and may account for the 5-fold reduction in rate compared with catechin.

Hydroxylation at the 4' position on the B-ring (position 12 in Formula 1) was an important feature of reactivity. Comparison of the kaempferol and datiscetin rate constants demonstrated a 56-fold reduction in activity on moving the hydroxyl from the 4' (position 12 in Formula 1) to the 2' position (position 10 in Formula 1). The presence of a 2'-OH (position 10 in Formula 1), however, substantially increases the reactivity of a hydroxyl on the 4' position (position 12 in Formula 1) as evidenced by the 8-fold increase in rate which morin displays relative to kaempferol. Methoxylation of the 4'-position (position 12 in Formula 1) of quercetin (tamarixetin) resulted in a 15-fold reduction in rate suggesting that the O—H bond dissociation enthalpy at the 4' position (position 12 in Formula 1) in quercetin is most favourable for H-atom transfer.

Of the fifteen flavonoids examined, eight had rate constants greater than that of vitamin E. Reaction stoichiometries show that many flavonoids can undergo multiple H-atom, or electron transfer, steps (see Table 1). Most effective in this respect was myricetin, in which each molecule could reduce four molecules of the radical. The non-integer values suggest that inter- or intra-molecular side reactions, involving partially-oxidised flavonoid intermediates, occur. The most important determinant of a high stoichiometric value was the presence of a catechol function on the B-ring. Of the fifteen compounds examined, eight were hydroxylated at the 3' position (position 11 in Formula 1) and 4' position (position 12 in Formula 1) and had reaction stoichiometries ranging from 2.8 (taxifolin) to 4.1 (myricetin). Without this functional group, the highest activity achieved was 1.8 (kaempferol and morin). The enhanced reductive capacity afforded by the catechol moiety is a possible consequence of a two-step oxidation to the ortho quinone. Morin, in which the second B-ring hydroxyl group is placed meta to the 4'-OH (position 12 in Formula 1), and consequently is unable to effect quinone formation, has a stoichiometric value of 1.8 compared with 3.3 for quercetin in which the second hydroxyl is placed ortho to the 4' position (position 12 in Formula 1). Activity was not a simple function of the number of hydroxyl groups present on the B- and C-rings. For example, datiscetin is morin with the 4'-OH (position 12 in Formula 1) removed, yet its reaction stoichiometry is essentially the same as that of morin. Rutin, which is quercetin with the 3-OH replaced by an ether-linked sugar moiety, retains similar activity.

A poor correlation (r=0.44) was found between the kinetic and stoichiometric parameters for the reduction of galvinoxyl by flavonoids. In particular, datiscetin, kaempferol and morin had almost identical reaction stoichiometries (ca 1.8), yet the reaction rates were 22, 1243 and 10134 mol$^{-1}$ dm$^3$ s$^{-1}$, respectively. These results highlight the importance of considering reaction kinetics, as well as stoichiometry, when assessing antioxidant capacity. Where two, or more, potential antioxidants are present, as may occur in complex cellular environments, kinetic factors may greatly over-ride reaction stoichiometry in determining which compound will afford greatest protection. Flavonoids, such as quercetin, may get absorbed from the diet into tissues. Consequently, kinetics and stoichiometry must both be considered in assessing the relevance of plant phenolics as nutritional antioxidants for disease prevention. This ESR method is a useful model to determine these two distinct aspects of antioxidant activity in a non-aqueous environment, as may be encountered in the lipid phase of cells. The galvinoxyl radical is insufficiently oxidising to indiscriminately abstract H-atoms from a wide range of substrates. Therefore, reactions are only likely to be significant with good H-donors, i.e. compounds which may fulfil an antioxidant role within a biological context.

EXAMPLE 18

Inhibition of TBARS production in rat liver microsomes from vitamin E-deficient rats by pre-incubation with target antioxidant and related compounds.

BACKGROUND

Microsomes are subcellular fractions containing membrane fragments. In vitamin E-deficient rats, microsomes are especially prone to oxidative free radical damage. This can be quantified in terms of the production of thiobarbituric acid reactive substances (TBARS) which result from radical-mediated destruction of the polyunsaturated fatty acid constituents. Consequently, this is a useful biological model to determine the efficacy of phytochemicals as antioxidant membrane protectants. Vitamin E-deficient microsomal suspensions were incubated for 30 minutes with one of myricetin, sample A, sample B, sample C (as shown below) or d-alpha-tocopherol, or with a compound 9c, 9d, 9e, 9e*, 9f, 9g, 9g*, 9h, 9i* or 9j (prepared as described above in Examples 1 to 10).

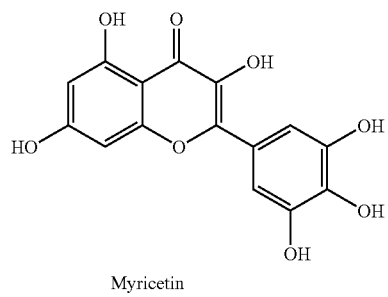

Myricetin

Control A

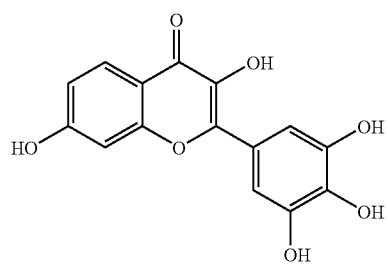

Control B

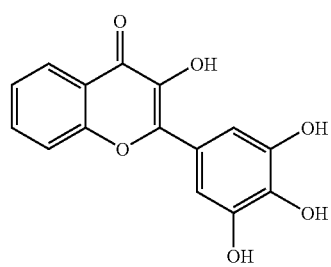

Control C

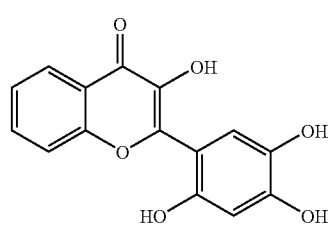

Control D

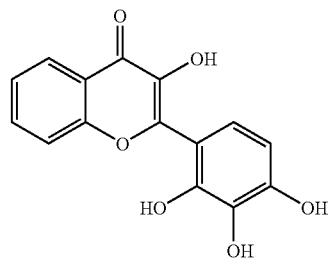

-continued

Control E

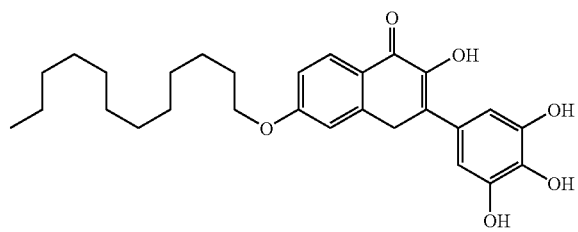

The microsomal suspension was then added to solutions containing Fe(II)-ADP/ascorbate to initiate free radical-mediated oxidation and incubated for a further 0, 5, 10, 15 or 20 minutes. TBARS production was then measured by HPLC.

In all the following examples and discussions, we will use the traditional numbering scheme for flavonoids rather than that defined in Formula 1 above. The traditional numbering is as shown below:

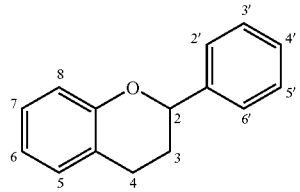

Results

In the absence of antioxidant protection (−E), TBARS production increases with time. Myricetin (M), although a potent antioxidant in chemical systems affords almost no protection. Control B, in which the two hydroxyls of myricetin have been removed to increase lipophilicity, is very soluble in octanol, and we have shown by ESR that it retains potent antioxidant activity. However, it does not give rise to significant membrane protective effects. Replacing the B ring hydroxy groups with methoxy produces a non-protective compound which has a lack of antioxidant activity in the ESR chemical medical system. Control E, which comprises an unbranched alkyl chain linked to the A-ring via oxygen and with a $C_{12}$ alkyl chain length, shows efficacy in the initial stages of microsomal oxidation. However, the protection is lost after 20 minutes. The target compounds according to the invention suppress oxidative damage throughout the 20 minute period and are comparable in effectiveness to dα-tocopherol (α).

Table 2 below gives the TBARs data obtained for compounds of varying chain length after 20 minutes incubation and normalised to a tocopherol reading of 20. The higher the reading the lower the protection provided. The TBARS data for membrane protection versus compound are presented as bar graphs in FIG. 2a and FIG. 2b. The same TBARS data for membrane protection plotted against compound lipophilicity are presented as scatter plots in FIG. 3a and FIG. 3b, respectively.

Table 3 summarises the TBARs data obtained after 20 minutes incubation and normalised to a tocopherol reading of 20, for compounds having different head groups and chain substitution sites.

Figure 2B:
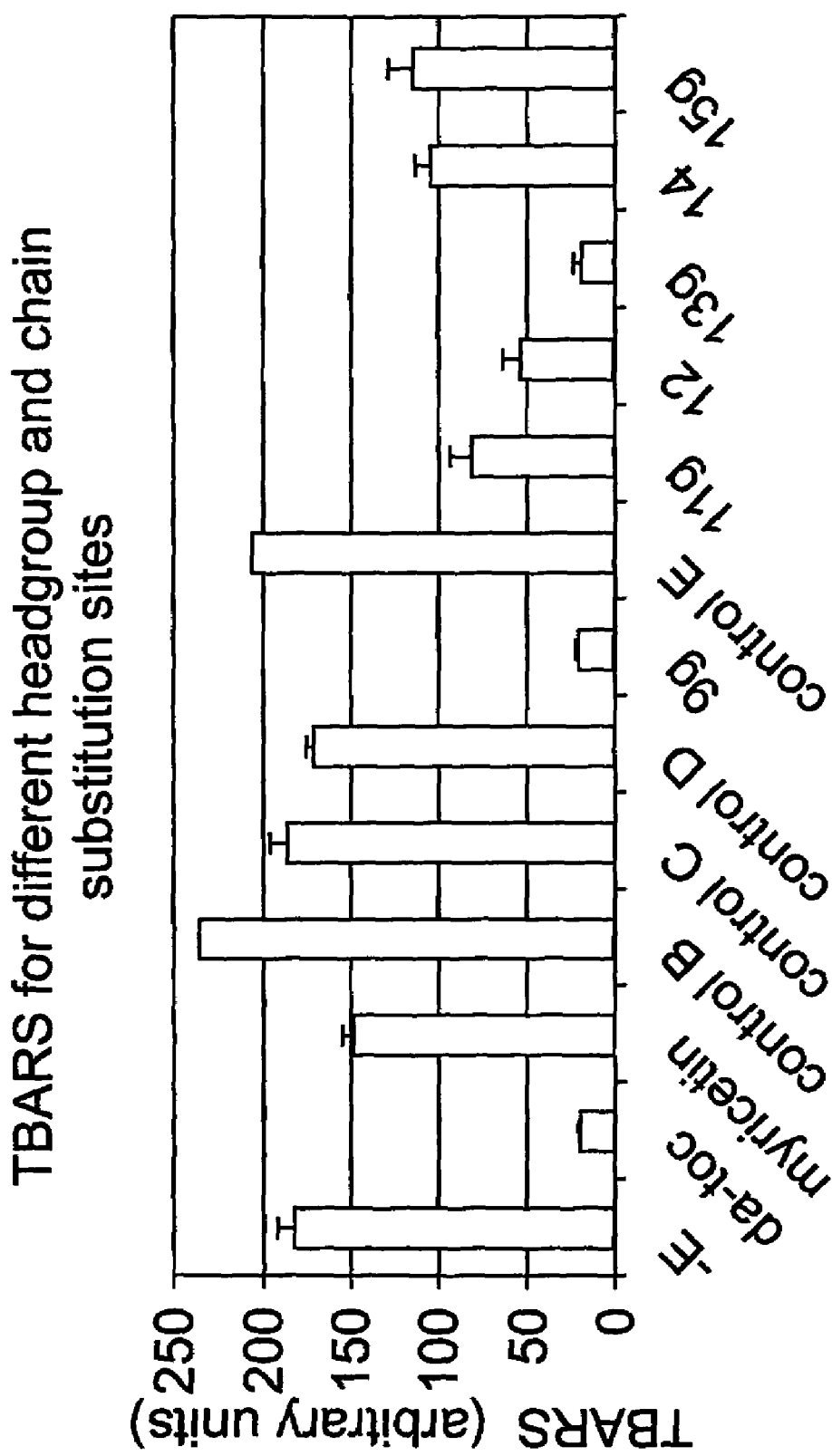
FIG. 2b shows the efficacy of target compounds of different head group and chain attachment at inhibiting lipid peroxidation by measuring their inhibition of TBARS production.
Figure 3A:
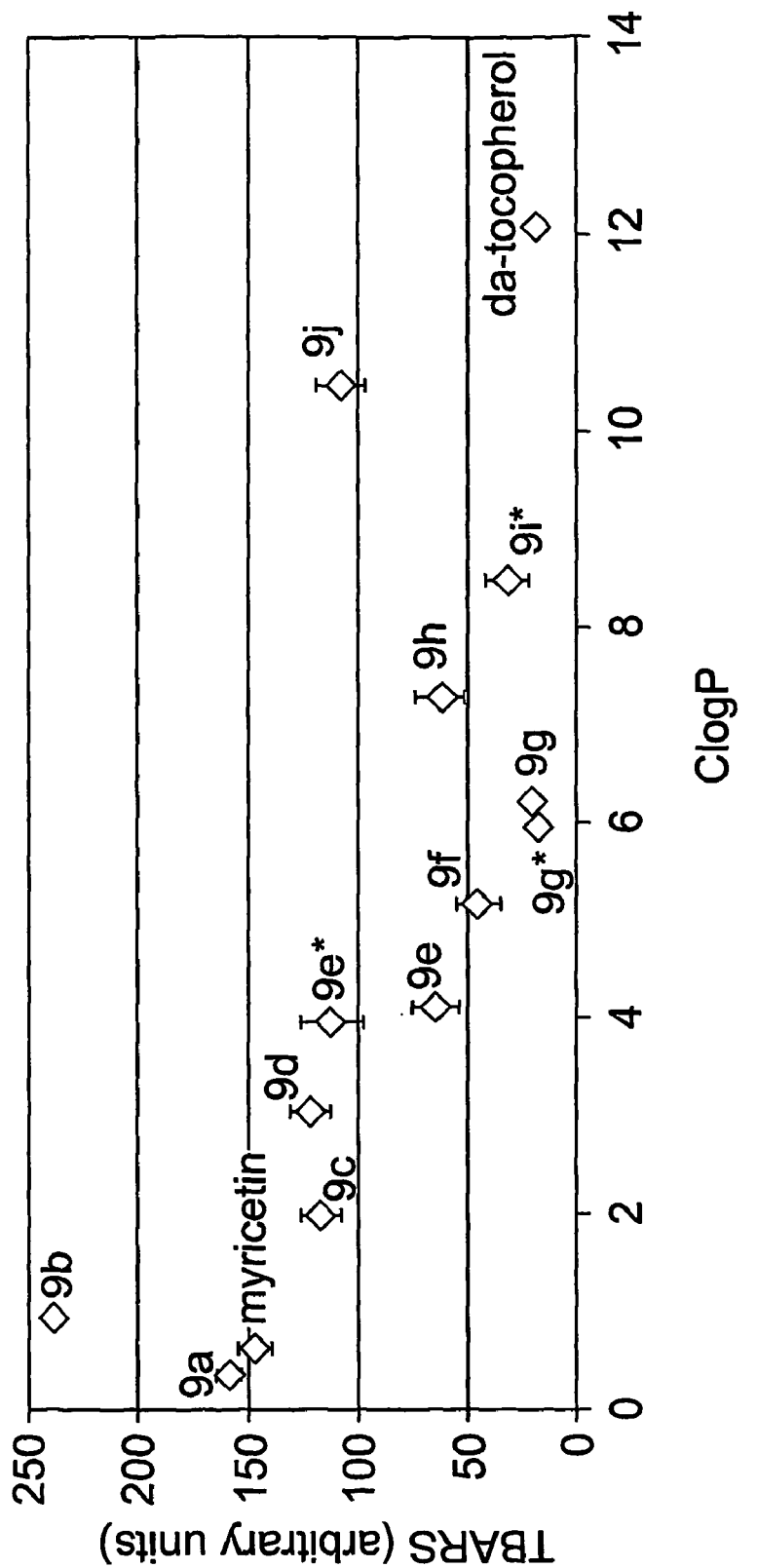
Figure 3B:
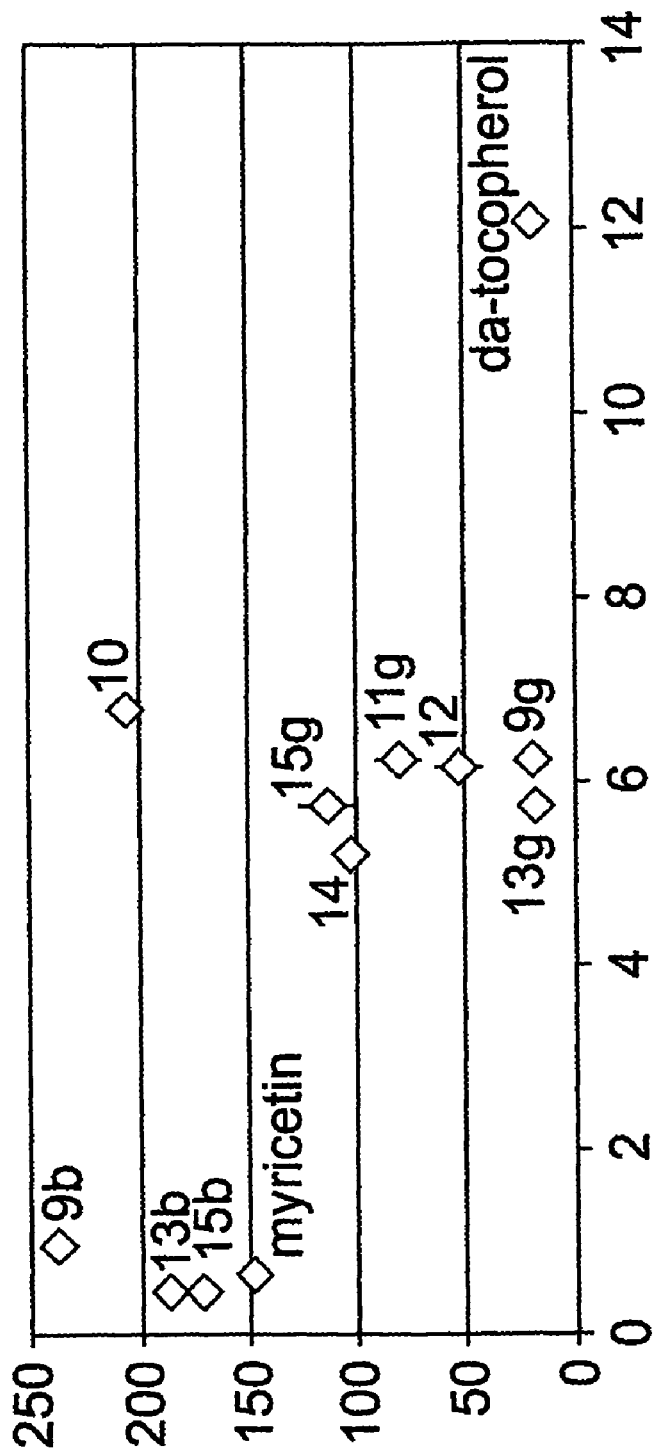
FIG. 3b is a scatter plot of the data shown in FIG. 2b.

The data in FIG. 2a shows that for a given head group and position of attachment of the chain, cell membrane protection depends strongly on the chain length. The optimum chain length for a chain attached at the 7-position is in the range C6 to C12. The data in FIG. 3a shows that for a given head group and position of attachment of the chain, cell membrane protection depends strongly on the lipophilicity as represented by calculated ClogP values. For compounds 9 bearing a chain attached to the 7-position good membrane protection is afforded by compounds with ClogP values in the range 4 to 10 (the compound with a ClogP value of 12 is α-d-tocopherol). The data in FIGS. 2b and 3b show the effect of varying the site at which the chain is attached, of varying the head group and of varying the nature of the atom linking the chain to the head group. Compounds 9g, 11g, and 12 have the same head group and almost identical lipophilicities (ClogP values) but different membrane protecting properties. Thus, we argue that there is an orientation effect that means that there is an optimum chain length for a particular site of attachment of the chain to a particular head group. Compounds 9g, 13g and 15g have the same chain length and site of attachment of the chain. They also have the same number of hydroxyl groups attached to the B and C rings. It is clear that the substitution pattern on the B-ring affects cell membrane protection. In particular a 3,3',4',5'-tetrahydroxy-flavone head group as in compound 9g and a 3,2',4',5'-tetrahydroxy-flavone head group as in compound 13g give good membrane protection. The poor membrane protection exhibited by compound 15g may be the result of poor orientation as this may be affected by the head group. Comparing the data for compound Control E and compound 9h shows that when the chain is attached to the head group by an oxygen atom rather than a carbon atom, membrane protection is less. This may also be an orientation effect.

The length of the $R_A$ chain also appears to have a major impact on activity (see compounds 9j, 9h, 9g and 9d). The order of activity is $C_{18} \approx C_2 < C_{12} < C_{10}$. This is also reflected in the two branched chain compounds (9i* and 9g*), where the compound having $C_8$ backbone has significantly higher inhibiting effects.

TABLE 1

| Compound | $k_2$ | Reaction Stoichiometry | Substitution Pattern | | | | | | | |
| --- | --- | --- | --- | --- | --- | --- | --- | --- | --- | --- |
| | | | 3 | 4 | 5 | 7 | 2' | 3' | 4' | 5' |
| Catechin | 1574 ± 79 | 2.96 ± 0.01 | —H, —OH | —H, —H | —OH | —OH | | —OH | —OH | |
| Taxifolin | 337 ± 32 | 2.82 ± 0.05 | —H, —OH | =O | —OH | —OH | | —OH | —OH | |
| Hesperitin | 6 ± 0.5 | 0.20 ± 0.02 | —H, —H | =O | —OH | —OH | | —OH | —OMe | |
| Apigenin | 5 ± 0.5 | 0.04 ± 0.02 | —H | =O | —OH | —OH | | | —OH | |
| Luteolin | 1212 ± 45 | 3.24 ± 0.01 | —H | =O | —OH | —OH | | —OH | —OH | |
| Galangin | 18 ± 1 | 1.01 ± 0.03 | —OH | =O | —OH | —OH | | | | |
| Fisetin | 1623 ± 199 | 3.68 ± 0.03 | —OH | =O | | —OH | | —OH | —OH | |
| Kaempferol | 1243 ± 99 | 1.84 ± 0.01 | —OH | =O | —OH | —OH | | | —OH | |
| Quercetin | 2383 ± 258 | 3.27 ± 0.04 | —OH | =O | —OH | —OH | | —OH | —OH | |

TABLE 1-continued

|  |  |  | Substitution Pattern | | | | | | | |
|---|---|---|---|---|---|---|---|---|---|---|
| Compound | $k_2$ | Reaction Stoichiometry | 3 | 4 | 5 | 7 | 2' | 3' | 4' | 5' |
| Tamarixetin | 165 ± 20 | 1.14 ± 0.03 | —OH | =O | —OH | —OH |  | —OH | —OMe |  |
| Rutin | 670 ± 41 | 3.18 ± 0.01 | —ORut* | =O | —OH | —OH |  | —OH | —OH |  |
| Myricetin | 14463 ± 1767 | 4.08 ± 0.01 | —OH | =O | —OH | —OH |  | —OH | —OH | —OH |
| Tri-Ome-Myricetin | 74 ± 14 | 1.06 ± 0.02 | —OH | =O | —OH | —OH |  | —OMe | —OMe | —OMe |
| Datiscetin | 22 ± 2 | 1.74 ± 0.02 | —OH | =O |  |  |  |  |  |  |
| Morin | 10134 ± 459 | 1.83 ± 0.01 | —OH | =O | —OH | —OH | —OH |  | —OH |  |
| Vitamin E | 524 ± 48 | 2.14 ± 0.12 |  |  | —OH | —OH | —OH |  |  |  |

Second order rate constants ($k_2$) and reaction stoichiometries for the reduciton of galvinoxyl radical by flavonoids and vitamin E.
*Rutin is quercetin-3-rutinoside. The compounds above the dotted line are based on the 2-H flavan system, while those below are Δ-2-flavan-4-ones.

TABLE 2

|  | –E | da-toc | myricetin | Control A | Control B | 9c | 9d | 9e |
|---|---|---|---|---|---|---|---|---|
| Mean | 182.783 | 19.9996 | 147.63062 | 158.348 | 236.525 | 117.461 | 121.743 | 65.5291 |
| SEM | 8.60267 | 0.86378 | 6.6099635 | 3.91252 |  | 9.51397 | 9.01775 | 10.0664 |
| ClogP |  | 12.048 | 0.637 | 0.378 | 0.956 | 1.984 | 3.042 | 4.1 |

|  | 9e* | 9f | 9g | 9g* | 9h | 9i* | 9j |
|---|---|---|---|---|---|---|---|
| Mean | 112.546 | 46.1879 | 21.6889 | 19.113 | 62.1021 | 32.9769 | 107.849 |
| SEM | 14.2328 | 9.97687 | 0.51033 | 1.76185 | 12.6367 | 9.48967 | 11.2272 |
| ClogP | 3.97 | 5.158 | 6.216 | 5.956 | 7.274 | 8.471 | 10.448 |

TABLE 3

|  | –E | da-toc | myricetin | Control B | Control C | Control D | 9g |
|---|---|---|---|---|---|---|---|
| Mean | 182.7825 | 19.99965 | 147.6306 | 236.5249 | 186.6221 | 172.0899 | 21.68894 |
| SEM | 8.602673 | 0.863783 | 6.609964 |  | 9.076549 | 2.393682 | 0.510328 |
| ClogP |  | 12.048 | 0.637 | 0.956 | 0.456 | 0.456 | 6.216 |

|  | Control E | 11g | 12 | 13g | 14 | 15g |
|---|---|---|---|---|---|---|
| Mean | 206.0328 | 81.81866 | 53.98257 | 20.1401 | 104.4307 | 114.1373 |
| SEM |  | 10.90688 | 10.01179 | 3.722299 | 8.686171 | 13.81451 |
| ClogP | 6.767 | 6.216 | 6.136 | 5.716 | 5.187 | 5.716 |

What is claimed is:

1. A compound of the following Formula 1:

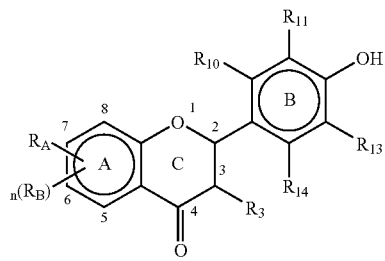

wherein
$R_A$ is a $C_2$ to $C_{30}$ saturated or unsaturated hydrocarbon chain;

$R_{10}$, $R_{11}$, $R_{13}$, $R_{14}$ and $R_3$ each independently represent H, OH, a $C_{1-6}$ ether, or a saturated or unsaturated hydrocarbon chain which may be substituted with one or more of nitro, halogen, amino, hydroxyl, ketone or aldehyde group, and wherein at least one of $R_{10}$, $R_{11}$ and $R_{13}$ represents OH;

optionally there is a double bond between $C_2$ and $C_3$ of the C ring;

n represents 0 or 1; and $R_B$ is a $C_2$ to $C_{15}$ saturated or unsaturated hydrocarbon chain, and where $R_B$ is present, $R_A$ and $R_B$ are both $C_2$ to $C_{12}$ aliphatic alkyl chains.

2. The compound of claim 1, wherein $R_{10}$ and/or $R_{11}$ represents OH.

3. The compound of claim 1, wherein $R_3$, $R_{11}$ and $R_{13}$ all represent OH.

4. The compound of claim 1, wherein $R_3$, $R_{10}$ and $R_{13}$ all represent OH.

5. The compound of claim 1, wherein there is a double bond between $C_2$ and $C_3$ of the C ring.

6. The compound of claim 1, wherein the backbone of $R_A$ has eight, nine or ten carbon atoms.

7. The compound of claim 1, wherein $R_A$ is attached to position 7 of the A ring of the flavonoid group.

8. The compound of claim 1, wherein $R_A$ has the following structure:

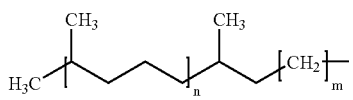

wherein
n is an integer from 1 to 7; and
m is an integer from 1 to 7.

9. The compound of claim 1, wherein $R_A$ has the following structure:

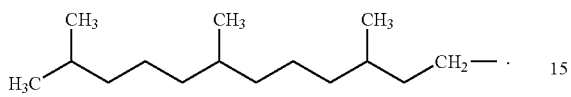

10. The compound of claim 1, wherein $R_A$ has the following structure:

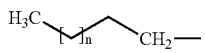

wherein n is an integer from 2 to 27.

11. The compound of claim 1, wherein $R_A$ has the following structure:

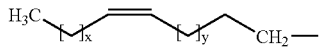

wherein
x is an integer from 1 to 25;
y is an integer from 1 to 25;
and wherein x+y=25 or less.

12. The compound of claim 1, wherein $R_A$ has the following structure:

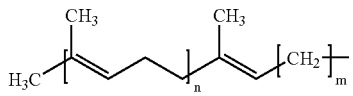

wherein
n is an integer from 1 to 7; and
m is an integer from 1 to 7.

13. The compound of claim 1, wherein the flavonoid group has one of the following structures:

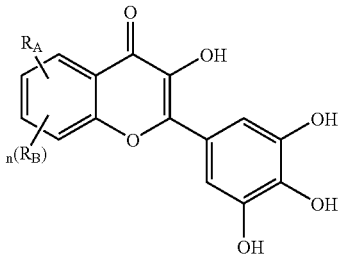

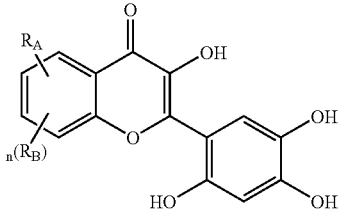

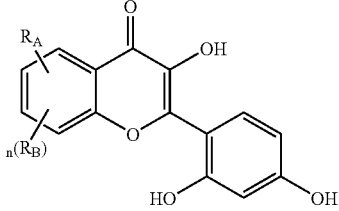

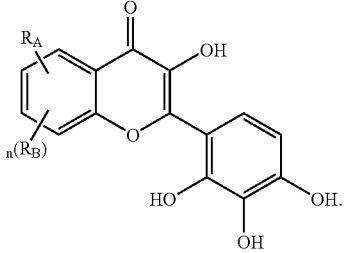

14. The compound of claim 1 having one of the following structures:

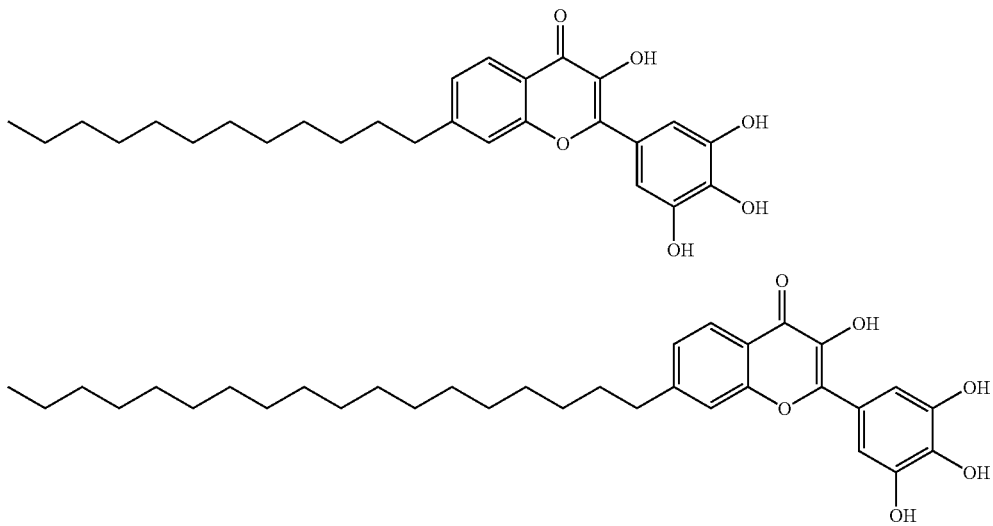

83 84
-continued
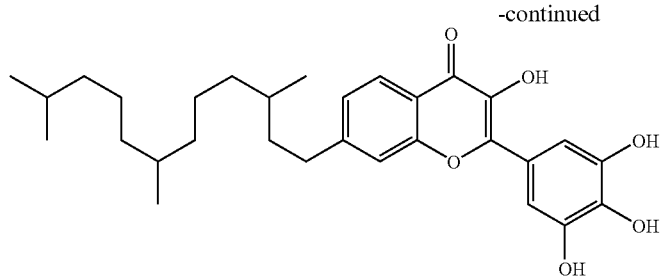 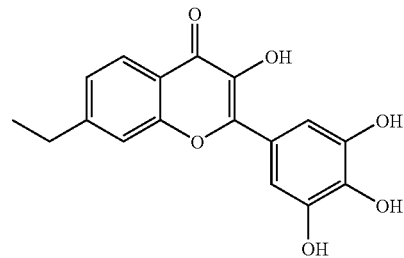
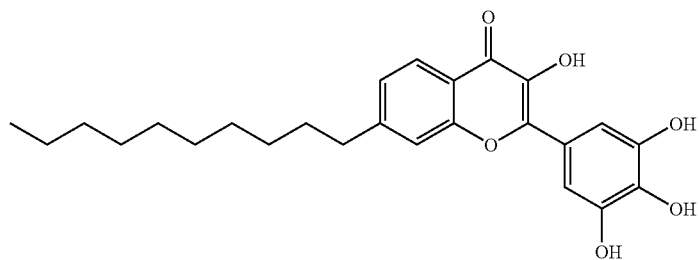
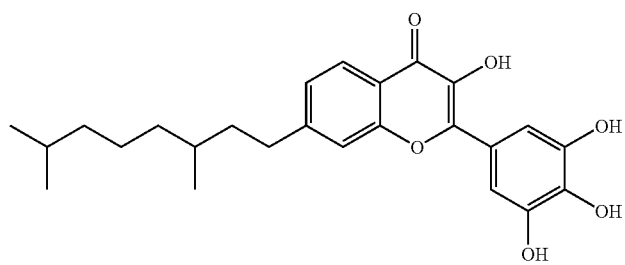
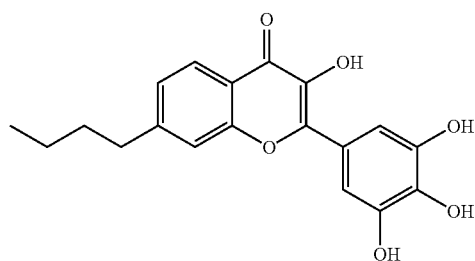 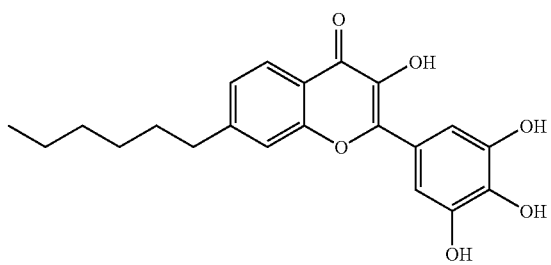
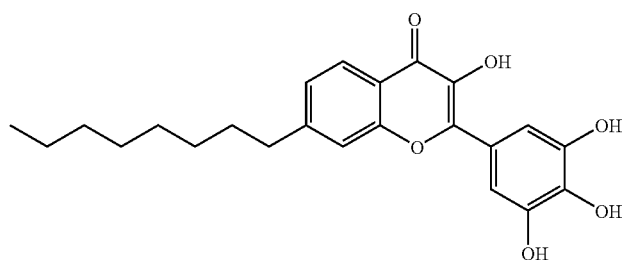
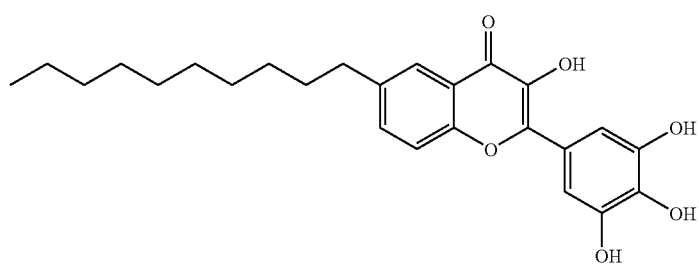

-continued

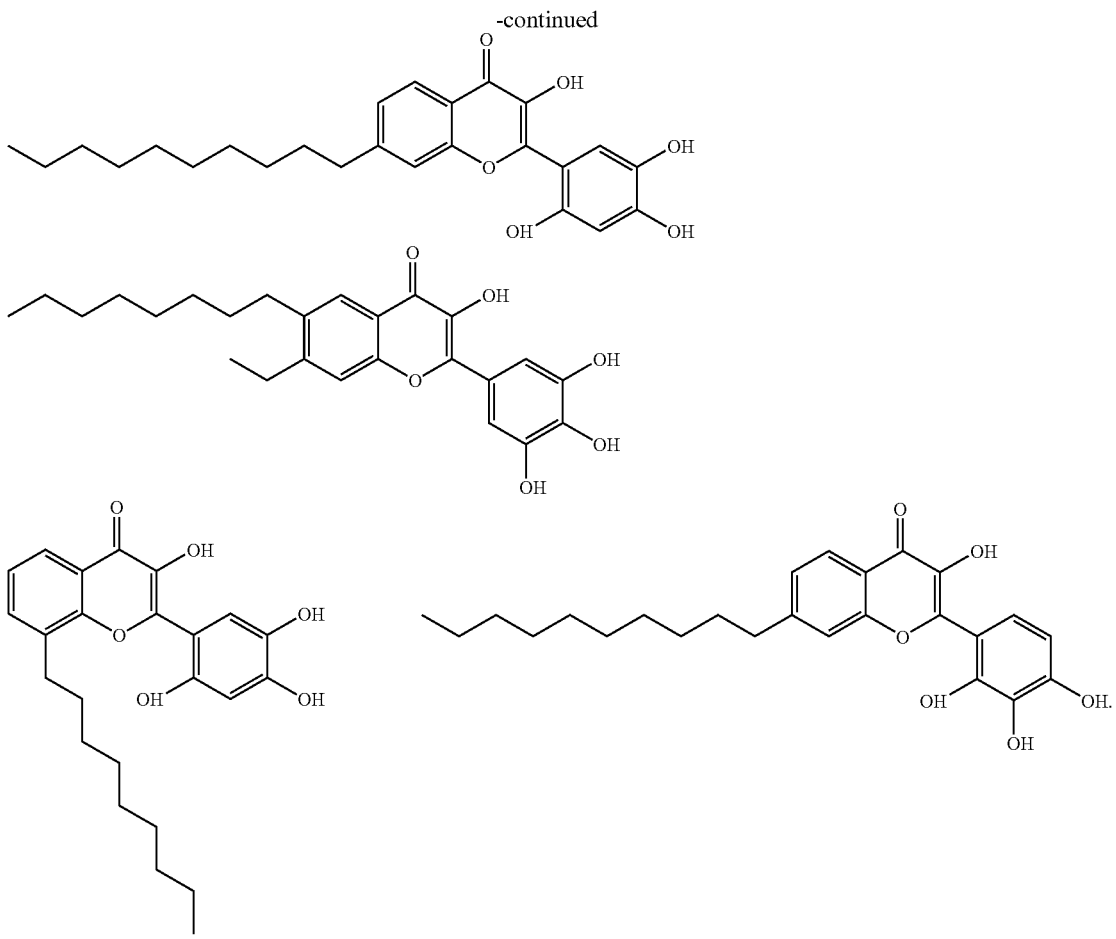

15. A composition comprising a compound of claim 1 and at least one pharmaceutical excipient or carrier.

16. The composition of claim 15 which is a sunscreen.

17. A method of preventing UV damage to the skin of a mammalian animal, said method comprising administering a therapeutically effective amount of the composition of claim 16 to said skin prior to UV exposure.

18. The method as claimed in claim 17 wherein said mammalian animal is a human.

19. The method of claim 17, wherein said composition is applied topically to said skin.

20. The composition of claim 15 which is a skincare composition.

21. The composition of claim 20, wherein said composition further comprises emollients and moisturisers.

22. A foodstuff stabiliser composition comprising a compound of claim 1.

23. The composition of claim 22, wherein said composition is in the form of an emulsion having a low fat:high water content.

24. A method of manufacturing a compound of Formula 1 as claimed in claim 1, said method comprising providing an intermediate compound A and an intermediate compound B, wherein intermediate compound A has the structure $R_4M$ wherein M is a metal or metalloid group where the metal is directly attached to $R_4$, and $R_4$ is a $C_2$ to $C_{30}$ saturated or unsaturated alkyl chain; and $R_4M$ is capable of participating in transition metal catalysed cross-coupling reactions;

and intermediate compound B has the following structure: wherein

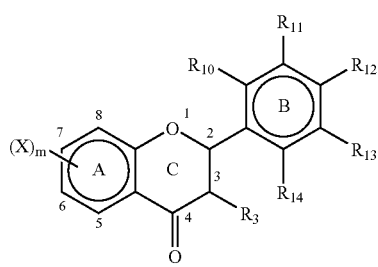

$R_{12}$ represents OH or an O-protecting group $R_3, R_{10}, R_{11}, R_{13}$, and $R_{14}$ each independently represent H, OH, $C_1$ to $C_4$ aliphatic alkyl group or an O-protecting group where required, and optionally there is a double bond between $C_2$ and $C_3$ of the C ring;

X is a halogen, O-trifluoromethane sulphonate or any other group used in cross-coupling reactions; and m=1 or 2, and reacting intermediate compound A with intermediate compound B by transition metal catalysed cross-coupling reactions and subsequently deprotecting at least one OH group.

25. The method of claim 24, wherein $R_4M$ is selected from the group consisting of an organomagnesium, organozinc, organoboron and an organotin compound.

26. The method of claim 24, wherein the catalyst is a palladium, nickel or iron complex.

27. A method of manufacturing a compound of Formula 1 as claimed in claim 1, said method comprising providing an intermediate Compound C and an intermediate Compound D, wherein said intermediate Compound C has the structure $R_A$CHCHR wherein $R_A$ is as defined in Formula 1, and wherein intermediate Compound D has a structure:

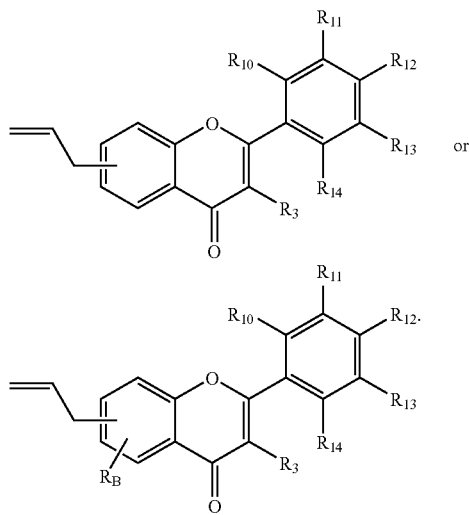

or

28. The method of claim 27, wherein the catalyst is:

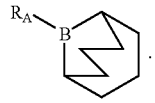

29. A method of manufacturing a compound of Formula 1 as claimed in claim 1, said method comprising providing an intermediate Compound E of formula:

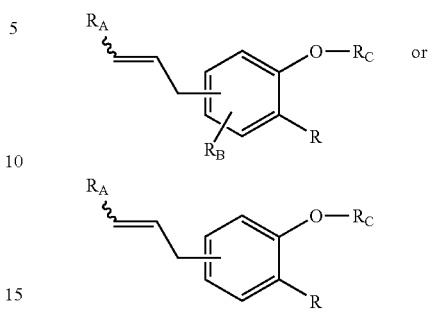

and constructing a flavonol core on said intermediate Compound E.

30. The method of claim 29, wherein said flavonol core is formed by Algar-Flynn-Oyamada (AFO) oxidation.

31. The method of claim 29, wherein said flavanol core is formed by Baker-Verkataraman rearrangement.

32. The method of claim 29, wherein said intermediate Compound E is formed by a transition metal catalysed cross-coupling reaction.

33. The method of claim 29, wherein said intermediate Compound E is formed by alkene cross-metathesis.

34. The compound of claim 1, wherein the backbone of $R_A$ has from 6 to 15 carbon atoms.

* * * * *